US008003627B2

(12) United States Patent
Augustyns et al.

(10) Patent No.: US 8,003,627 B2
(45) Date of Patent: Aug. 23, 2011

(54) UROKINASE INHIBITORS

(75) Inventors: Koen Augustyns, Hoogstraten (BE); Jurgen Joossens, Zoersel (BE); Pieter Van Der Veken, Antwerpen (BE); Anne-Marie Virginie Renée Lambeir, Leuven (BE); Simon Scharpé, Wieze (BE); Achiel Haemers, Sint-Martens-Latem (BE)

(73) Assignee: Universiteit Antwerpen (BE)

( * ) Notice: Subject to any disclaimer, the term of this patent is extended or adjusted under 35 U.S.C. 154(b) by 377 days.

(21) Appl. No.: 12/090,984

(22) PCT Filed: Oct. 20, 2006

(86) PCT No.: PCT/EP2006/010147
§ 371 (c)(1),
(2), (4) Date: Aug. 14, 2008

(87) PCT Pub. No.: WO2007/045496
PCT Pub. Date: Apr. 26, 2007

(65) Prior Publication Data
US 2008/0312191 A1    Dec. 18, 2008

(30) Foreign Application Priority Data

Oct. 21, 2005 (WO) .................. PCT/EP2005/011341

(51) Int. Cl.
*A61K 31/66* (2006.01)
*C07F 9/02* (2006.01)
(52) U.S. Cl. ........................................ 514/119; 558/176
(58) Field of Classification Search .................. 514/119; 558/176
See application file for complete search history.

(56) References Cited

U.S. PATENT DOCUMENTS 5,952,307 A * 9/1999 Powers et al. .................... 514/19
7,786,098 B2 * 8/2010 Shen et al. ..................... 514/130

OTHER PUBLICATIONS

Cheruvallath et al., 2006, CAS: 144: 212913.*
El Sayed et al., 2005, CAS: 142:447258.*
Joossens et al., 2004, CAS: 141:7427.*
Senten et al., 2003, CAS: 138:287948.*
Hamilton et al., 1993, CAS: 120: 192271.*
Powers et al., 1997, CAS: 128:3887.*
Office Action for European Application No. EP 06 806 436.9, dated Jul. 30, 2009.
Joosens et al., "Development of Irreversible Diphenyl Phosphonate Inhibitors for Urokinase Plasminogen Activator," *J. Med. Chem.* 47(10):2411-2413 (2004).
Joosens et al., "Diphenyl Phosphonate Inhibitors for the Urokinase-type Plasminogen Activator: Optimization of the P4 Position," *J. Med. Chem.* 49(19):5785-5793 (2006).
Sienczyk and Oleksyszyn, "A Convenient Synthesis of New Alpha-Aminoalkylphosphonates, Aromatic Analogues of Arginine as Inhibitors of Trypsin-like Enzymes," *Tetrahedron Lett.* 45(39):7251-7254 (2004).
Sienczyk and Oleksyszyn, "Inhibition of Trypsin and Urokinase by Cbz-amino(4-guanidino-phenyl)methanephosphonate Aromatic Ester Derivatives: The Influence of the Ester Group on their Biological Activity," *Bioorg. Med. Chem. Lett.* 16(11):2886-2890 (2006).
International Preliminary Report on Patentability for International Application No. PCT/EP2006/010147, mailed Jan. 16, 2008.
International Search Report for International Application No. PCT/EP2006/010147, mailed Mar. 9, 2007.
Written Opinion of the International Searching Authority for International Application No. PCT/EP2006/010147, mailed Mar. 9, 2007.
Official Communication for European Patent Application No. 06 806 436.9, dated Feb. 2, 2010.
Dass et al., "Evolving Role of uPA/uPAR System in Human Cancers," *Cancer Treat. Rev.* 1-15 (2007).
Duffy et al., "The Urokinase Plasminogen Activator System: A Rich Source of Tumor Markers for the Individualised Management of Patients with Cancer," *Clin. Biochem.* 541-548 (2004).
EPO Communication inviting applicant to correct deficiencies found during examination of EP Application No. 06 806 436.9-2117 dated Jan. 18, 2011.
Hofmeister et al., "Anti-Cancer Therapies Targeting the Tumor Stroma," *Cancer Immunol. Immunother.* 1-17 (2008).

* cited by examiner

*Primary Examiner* — Rei-tsang Shiao
(74) *Attorney, Agent, or Firm* — Clark & Elbing LLP

(57) ABSTRACT

The present invention relates to novel compounds with inhibitory activity towards urokinase plasminogen activator (uPA); to methods for preparation of said uPA inhibitor compounds; to pharmaceutical compositions comprising said uPA inhibitor compounds; to the use of said uPA inhibitor compounds as a medicament and the use of said uPA inhibitor compounds for the preparation of a medicament for the treatment of conditions chosen from the group comprising cancer, tumour growth, tumour invasion, tumour metastasis, diabetic retinopathy, hemorrhagic atherosclerosis and inflammatory conditions, such as rheumatoid arthritis and psoriasis.

14 Claims, No Drawings

UROKINASE INHIBITORS

CROSS-REFERENCE TO RELATED APPLICATIONS

This application is the U.S. National Stage of International Application No. PCT/EP2006/010147, filed Oct. 20, 2006, which claims the benefit of PCT International Application No. PCT/EP2005/011341, filed Oct. 21, 2005.

The present invention relates to the medical field. In an aspect, the invention relates to novel compounds with inhibitory activity towards urokinase plasminogen activator (uPA). In another aspect, the present invention relates to a method for preparation of said uPA inhibitor compounds. In a further aspect, the invention relates to a pharmaceutical composition comprising an effective amount of said uPA inhibitor compounds. In yet further aspect, the invention concerns the use of said uPA inhibitor compounds as a medicament and the use of said uPA inhibitor compounds for the preparation of a medicament for the treatment of a conditions chosen from the group comprising cancer, tumour growth, tumour invasion, tumour metastasis, diabetic retinopathy, hemorrhagic atherosclerosis and inflammatory conditions, such as rheumatoid arthritis and psoriasis.

The ability of solid tumors to spread and metastasize in surrounding tissue correlates with the degradation or transformation of the extracellular matrix (tumor stroma) in the vicinity of the tumor cell and/or with the ability of said tumors to penetrate the basement membrane. Although the (patho) biochemical connections have not been completely elucidated yet, the plasminogen activator urokinase (uPA) and the urokinase receptor (uPAR) play a central role. uPA mediates the proteolytic cleavage of plasminogen to give plasmin. Plasmin in turn is a protease which has a wide range of actions and is capable of directly breaking down components of the extracellular matrix such as fibrin, fibronectin, laminin and the protein skeleton of proteoglycans. In addition, plasmin can activate "latent" metalloproteases and the inactive proenzyme of uPA, pro-uPA.

Tumor cells and non-malignant cells of the tumor stroma synthesize and secrete the enzymatically inactive proenzyme pro-uPA. Proteases such as, for example, plasmin or the cathepsins B and L cleave pro-uPA by limited proteolysis to give the active serine protease HMW-uPA (HMW=high molecular weight). Pro-uPA and the active protease HMW-uPA bind to the cell surface receptor uPAR (CD87). Plasmin (ogen) likewise binds to specific receptors on the plasma membranes of tumor cells which leads to focused and amplified plasminogen activation in the immediate vicinity of the tumor cells. Invasive cells thus are able to break down the extracellular matrix without finding themselves deprived of the support necessary for directed movement because of proteolysis.

The use of synthetic uPA inhibitors makes it possible to suppress invasion and spreading of tumor cells. However, developing specific uPA inhibitors is difficult, since tissue plasminogen activator (tPA) has an identical specificity for cleaving the peptide bond Arg560/Val561 of plasminogen. In most cases therefore, low molecular weight uPA inhibitors also inhibit tPA and thus also tPA-mediated fibrinolysis. Despite these restrictions, some inhibitors are known.

Joossens et al. (J Med. Chem. 2004 May 6; 47(10):2411-3) disclosed the synthesis and biochemical evaluation of selective, irreversible diphenyl phosphonate inhibitors for urokinase plasminogen activator (uPA). A diphenyl phosphonate group was introduced on the substratelike peptide Z-d-Ser-Ala-Arg, and modification of the guanidine side chain was investigated. A guanylated benzyl group appeared the most promising side chain modification. A $k_{app}$ value in the $10^3$ $M^{-1}s^{-1}$ range for uPA was obtained, together with a selectivity index higher than 240 toward other trypsin-like proteases such as tPA, thrombin, plasmin, and FXa.

A skilled person would presuppose that the substratelike tripeptide Z-D-Ser-Ala-Arg was crucial for the uPA inhibitory activity of these compounds and their selectivity. Indeed, Z-D-Ser-Ala-Arginal itself has been known to be a uPA inhibitor with an $IC_{50}$ value of 19 nM and a selectivity ratio of more than 130 toward tPA (Tamura et al. Bioorg Med Chem. Lett. 2000 May 1; 10(9):983-7) and the study of Joossens et al. in fact attempted further optimisation of this inhibitor.

Therefore, it is surprising that, as demonstrated by the present inventors, compounds analogous to those described by Joossens et al., in which the Z-d-Ser-Ala-Arg is replaced by a non-peptidyl moiety, show similar or improved activity and selectivity profile as the tripeptide containing inhibitors. The present invention realizes that such compounds can be used as effective uPA inhibitors.

Hereby, the present invention provides for novel pharmaceutically useful uPA inhibitors. The said uPA inhibitors are simpler in structure than those described in Joossens et al., in particular they do not contain a tripeptidyl moiety, and their synthesis therefore requires less steps, which is advantageous. Moreover, due to their smaller size, the peptides may have more favourable biokinetic properties.

In an aspect, the present invention concerns urokinase inhibitor compounds having the formula (I)

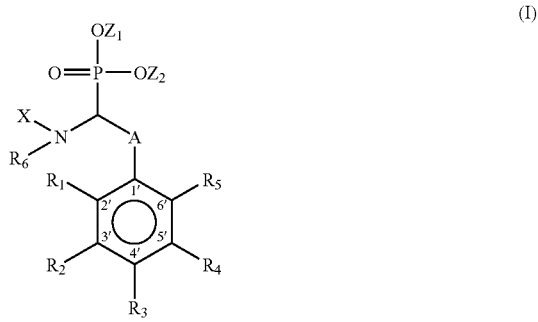

and N-oxides, stereoisomeric forms, racemic mixtures, prodrugs, esters, pharmaceutically acceptable salts and metabolites thereof, wherein at least one of the substituents $R^1$, $R^2$, $R^3$, $R^4$ and $R^5$ is independently chosen from the group comprising or consisting of: amidino; substituted amidino, such as monosubstituted amidino, disubstituted amidino and trisubstituted amidino, wherein the substituents in the substituted amidino are, each independently, chosen from $R^a$, preferably from $R^e$ and more preferably from $R^d$; guanidino; substituted guanidino, such as monosubstituted guanidino, disubstituted guanidino, trisubstituted guanidino and tetrasubstituted guanidino, wherein the substituents in the substituted guanidino are, each independently, chosen from $R^a$, preferably from $R^e$ and more preferably from $R^d$;

wherein the remaining substituents of the substituents $R^1$, $R^2$, $R^3$, $R^4$ and $R^5$ are, each independently, chosen from the group comprising or consisting of: hydrogen, halogen, perhaloalkyl, and $R^7$; wherein $R^7$ comprises: alkyl, alkenyl, alkynyl, cycloalkyl, cycloalkylalkyl, cycloalkylalkenyl, aryl, aralkyl, arylalkenyl, Het$^1$, Het$^1$alkyl, Het$^1$alkenyl, Het$^1$cycloalkyl, Het$^1$cycloalkylalkyl, Het$^1$alkylcycloalkyl, Het¹alkylcycloalkylalkyl, Het¹aryl, Het¹aralkyl, Het¹alkylaryl, Het¹alkylaralkyl, Het², Het²alkyl, Het²alkenyl, Het²cycloalkyl, Het²cycloalkylalkyl, Het²alkylcycloalkyl, Het²alkylcycloalkylalkyl, Het²aryl, Het²aralkyl, Het²alkylaryl Het²alkylaralkyl, arylaminoalkyl, hydroxyl and substituted hydroxyl, wherein the substituent in the substituted hydroxyl is chosen from $R^a$, preferably from $R^e$ and more preferably from $R^d$; etherified hydroxyl including alkoxy, aryloxy, aralkoxy, Het¹oxy, Het¹alkoxy, Het¹aryloxy, Het²oxy, Het²alkoxy and Het²aryloxy; mercapto and substituted mercapto, wherein the substituent in the substituted mercapto is chosen from $R^a$, preferably from $R^e$ and more preferably from $R^d$; etherified mercapto including alkylthio, arylthio, aralkylthio, Het¹thio, Het¹alkylthio, Het¹arylthio, Het²thio, Het²alkylthio and Het²arylthio; formyl, acyl including alkanoyl, cycloalkylcarbonyl, aroyl, aralkanoyl, Het¹carbonyl, Het¹alkanoyl, Het¹aroyl, Het²carbonyl, Het²alkanoyl, Het²aroyl; hydroxyalkanoyl, alkoxyalkanoyl, oxoalkanoyl, aminoalkanoyl, aryloxyalkanoyl, thioformyl, thioacyl including alkylthiocarbonyl, arylthiocarbonyl, aralkylthiocarbonyl, Het¹thiocarbonyl, Het¹alkylthiocarbonyl, Het¹arylthiocarbonyl, Het²thiocarbonyl, Het²alkylthiocarbonyl and Het²arylthiocarbonyl; formyloxy, acyloxy including alkanoyloxy, cycloalkylcarbonyloxy, aroyloxy, aralkanoyloxy, Het¹carbonyloxy, Het¹alkanoyloxy, Het²carbonyloxy and Het²alkanoyloxy; formylthio, acylthio including alkanoylthio, aroylthio, aralkanoylthio, Het¹carbonylthio, Het¹alkanoylthio, Het²carbonylthio and Het²alkanoylthio; thioformyloxy, thioacyloxy including alkylthiocarbonyloxy, arylthiocarbonyloxy, aralkylthiocarbonyloxy, Het¹thiocarbonyloxy, Het¹alkylthiocarbonyloxy, Het²thiocarbonyloxy and Het²alkylthiocarbonyloxy; thioformylthio, thioacylthio including alkylthiocarbonylthio, arylthiocarbonylthio, aralkylthiocarbonylthio, Het¹thiocarbonylthio, Het¹alkylthiocarbonylthio, Het²thiocarbonylthio and Het²alkylthiocarbonylthio; carboxyl, substituted carboxyl, esterified carboxyl including alkoxycarbonyl, cycloalkylalkoxycarbonyl, aryloxycarbonyl, aralkoxycarbonyl, Het¹oxycarbonyl, Het¹alkoxycarbonyl, Het¹aryloxycarbonyl, Het²oxycarbonyl, Het²alkoxycarbonyl and Het²aryloxycarbonyl; thiocarboxyl, substituted thiocarboxyl, esterified thiocarboxyl including alkoxythiocarbonyl, aryloxythiocarbonyl, aralkoxythiocarbonyl, Het¹oxythiocarbonyl, Het¹alkoxythiocarbonyl, Het¹aryloxythiocarbonyl, Het²oxythiocarbonyl, Het²alkoxythiocarbonyl, Het²aryloxythiocarbonyl, (alkylthio)carbonyl, (arylthio)carbonyl, (aralkylthio)carbonyl, (Het¹thio)carbonyl, (Het¹alkylthio)carbonyl, (Het¹arylthio)carbonyl, (Het²thio)carbonyl, (Het²alkylthio)carbonyl, (Het²arylthio)carbonyl, (alkylthio)thiocarbonyl, (arylthio)thiocarbonyl, (aralkylthio)thiocarbonyl, (Het¹thio)thiocarbonyl, (Het¹alkylthio)thiocarbonyl, (Het¹arylthio)thiocarbonyl, (Het²thio)thiocarbonyl, (Het²alkylthio)thiocarbonyl and (Het²arylthio)thiocarbonyl; carbamoyl and substituted carbamoyl, such as monosubstituted carbamoyl and disubstituted carbamoyl, wherein the substituents in the substituted carbamoyl are, each independently, chosen from $R^a$, preferably from $R^e$ and more preferably from $R^d$, including alkylcarbamoyl, cycloalkylcarbamoyl, arylcarbamoyl, aralkylcarbamoyl, Het¹carbamoyl, Het¹alkylcarbamoyl, Het¹arylcarbamoyl, Het²carbamoyl, Het²alkylcarbamoyl, Het²arylcarbamoyl; thiocarbamoyl and substituted thiocarbamoyl, such as monosubstituted thiocarbamoyl and disubstituted thiocarbamoyl, wherein the substituents in the substituted thiocarbamoyl are, each independently, chosen from $R^a$, preferably from $R^e$ and more preferably from $R^d$; sulfinyl, sulfonyl, aminosulfinyl, aminosulfonyl, sulfeno and substituted sulfeno, sulfino and substituted sulfino, sulfo and substituted sulfo, and $R^7$ further comprises all of the above listed $R^7$ groups when optionally substituted with one or more substituents independently chosen from the group comprising or consisting of: halogen, perhaloalkyl, nitro, cyano, alkyl, aryl, aralkyl, Het¹alkyl, Het²alkyl, hydroxyl, alkoxy, aryloxy, aralkoxy, —OC(=NR')R'', mercapto, alkylthio, arylthio, aralkylthio, —SC(=NR')R'', formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, Het¹carbonylamino, Het¹alkanoylamino, Het²carbonylamino, Het²alkanoylamino, sulfo and substituted sulfo, sulfonyl, aminosulfonyl, imino, —C(=NR')OH, —C(=NR')OR'', —C(=NR')SH, —C(=NR')SR'', oxo, primary amino, secondary amino, and tertiary amino, wherein the substituents in the secondary and tertiary amino are, each independently, chosen from $R^e$ and preferably $R^d$, alkylamino, arylamino, aralkylamino, Het¹amino, Het¹alkylamino, Het²amino and Het²alkylamino, —NR'C(=O)OR'', —NR'C(O)NR''R''', —NR'C(S)NR''R''', —N(OH)C(=O)OR', —NR'C(=O)SR'', —N(OH)C(=O)NR'R'', —N(OH)C(S)NR'R''', —NR'C(O)N(OH)R'', —NR'C(S)N(OH)R'', —NR'S(=O)₂R'', —NHS(=O)₂NR'R'', —NR'S(=O)₂NHR'', and —P(=O)(OR'')(OR'''), wherein R', R'' and R''' are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino;

wherein A is chosen from the group comprising or consisting of a direct bond, alkylene and alkenylene, preferably A is chosen from the group comprising or consisting of a direct bond and $C_{1-6}$alkylene, more preferably A is chosen from the group comprising or consisting of a direct bond, methylene and ethylene, wherein the said alkylene, alkenylene, $C_{1-6}$alkylene, methylene or ethylene is optionally substituted by one or more substituents independently chosen from the group comprising or consisting of halogen, perhaloalkyl, nitro, cyano, alkyl, aryl, aralkyl, hydroxyl, alkoxy, aryloxy, aralkoxy, formyl, alkanoyl, aroyl, aralkanoyl, formyloxy, alkanoyloxy, aroyloxy, aralkanoyloxy, alkoxycarbonyl, aryloxycarbonyl, aralkoxycarbonyl, primary amino, secondary amino, and tertiary amino, wherein the substituents in the secondary and tertiary amino are, each independently, chosen from $R^e$ and preferably from $R^d$, even more preferably from the group comprising or consisting of alkyl, aryl, aralkyl, Het¹, Het¹alkyl, Het², Het²alkyl, alkanoyl and aralkanoyl;

wherein $R^6$ is chosen from the group comprising or consisting of hydrogen, alkyl and aralkyl, preferably $R^6$ is chosen from the group comprising or consisting of hydrogen, $C_{1-6}$alkyl and aryl$C_{1-6}$alkyl, more preferably $R^6$ is chosen from the group comprising or consisting of hydrogen and $C_{1-6}$alkyl, wherein the said alkyl, $C_{1-6}$alkyl, aralkyl and aryl$C_{1-6}$alkyl is optionally substituted by one or more substituents independently chosen from the group comprising or consisting of halogen, hydroxyl, alkoxy, aryloxy, aralkoxy, alkanoyl, aroyl, aralkanoyl, formyloxy, alkanoyloxy, aroyloxy, aralkanoyloxy, alkoxycarbonyl, aryloxycarbonyl, aralkoxycarbonyl, primary amino, secondary amino, and tertiary amino, wherein the substituents in the secondary and tertiary amino are, each independently, chosen from $R^e$ and preferably from $R^d$, even more preferably from the group comprising or consisting of alkyl, aralkyl, alkanoyl and aralkanoyl;

wherein, with the proviso that X is not peptidyl, X is chosen from the group comprising or consisting of: hydrogen, alkyl, alkenyl, alkynyl, cycloalkyl, cycloalkylalkyl, cycloalkylalkenyl, aryl, aralkyl, arylalkenyl, $Het^1$, $Het^1$alkyl, $Het^1$alkenyl, $Het^1$cycloalkyl, $Het^1$cycloalkylalkyl, $Het^1$alkylcycloalkyl, $Het^1$alkylcycloalkylalkyl, $Het^1$aryl, $Het^1$aralkyl, $Het^1$alkylaryl, $Het^1$alkylaralkyl, $Het^2$, $Het^2$alkyl, $Het^2$alkenyl, $Het^2$cycloalkyl, $Het^2$cycloalkylalkyl, $Het^2$alkylcycloalkyl, $Het^2$alkylcycloalkylalkyl, $Het^2$aryl, $Het^2$aralkyl, $Het^2$alkylaryl $Het^2$alkylaralkyl, perhaloalkyl, formyl, acyl including alkanoyl, cycloalkylcarbonyl, aroyl, aralkanoyl, $Het^1$carbonyl, $Het^1$alkanoyl, $Het^1$aroyl, $Het^2$carbonyl, $Het^2$alkanoyl, $Het^2$aroyl; hydroxyalkanoyl, alkoxyalkanoyl, oxoalkanoyl, aminoalkanoyl, aryloxyalkanoyl, thioformyl, thioacyl including alkylthiocarbonyl, arylthiocarbonyl, aralkylthiocarbonyl, $Het^1$thiocarbonyl, $Het^1$alkylthiocarbonyl, $Het^1$arylthiocarbonyl, $Het^2$thiocarbonyl, $Het^2$alkylthiocarbonyl and $Het^2$arylthiocarbonyl; carboxyl, substituted carboxyl, esterified carboxyl including alkoxycarbonyl, cycloalkylalkoxycarbonyl, aryloxycarbonyl, aralkoxycarbonyl, $Het^1$oxycarbonyl, $Het^1$alkoxycarbonyl, $Het^1$aryloxycarbonyl, $Het^2$oxycarbonyl, $Het^2$alkoxycarbonyl and $Het^2$aryloxycarbonyl; thiocarboxyl, substituted thiocarboxyl, esterified thiocarboxyl including alkoxythiocarbonyl, aryloxythiocarbonyl, aralkoxythiocarbonyl, $Het^1$oxythiocarbonyl, $Het^1$alkoxythiocarbonyl, $Het^1$aryloxythiocarbonyl, $Het^2$oxythiocarbonyl, $Het^2$alkoxythiocarbonyl, $Het^2$aryloxythiocarbonyl, (alkylthio)carbonyl, (arylthio)carbonyl, (aralkylthio)carbonyl, ($Het^1$thio)carbonyl, ($Het^1$alkylthio)carbonyl, ($Het^1$arylthio)carbonyl, ($Het^2$thio)carbonyl, ($Het^2$alkylthio)carbonyl, ($Het^2$arylthio)carbonyl, (alkylthio)thiocarbonyl, (arylthio)thiocarbonyl, (aralkylthio)thiocarbonyl, ($Het^1$thio)thiocarbonyl, ($Het^1$alkylthio)thiocarbonyl, ($Het^1$arylthio)thiocarbonyl, ($Het^2$thio)thiocarbonyl, ($Het^2$alkylthio)thiocarbonyl, ($Het^2$arylthio)thiocarbonyl; carbamoyl and substituted carbamoyl, such as monosubstituted carbamoyl and disubstituted carbamoyl, wherein the substituents in the substituted carbamoyl are, each independently, chosen from $R^a$, preferably from $R^e$ and more preferably from $R^d$, including alkylcarbamoyl, cycloalkylcarbamoyl, arylcarbamoyl, aralkylcarbamoyl, $Het^1$carbamoyl, $Het^1$alkylcarbamoyl, $Het^1$arylcarbamoyl, $Het^2$carbamoyl, $Het^2$alkylcarbamoyl, $Het^2$arylcarbamoyl; thiocarbamoyl and substituted thiocarbamoyl, such as monosubstituted thiocarbamoyl and disubstituted thiocarbamoyl, wherein the substituents in the substituted thiocarbamoyl are, each independently, chosen from $R^a$, preferably from $R^e$ and more preferably from $R^d$; sulfinyl including alkylsulfinyl, arysulfinyl, aralkylsulfinyl, $Het^1$sulfinyl, $Het^1$alkylsulfinyl, $Het^1$arylsulfinyl, $Het^2$sulfinyl, $Het^2$alkylsulfinyl and $Het^2$arylsulfinyl; sulfonyl including alkylsulfonyl, arysulfonyl, aralkylsulfonyl, $Het^1$sulfonyl, $Het^1$alkylsulfonyl, $Het^1$arylsulfonyl, $Het^2$sulfonyl, $Het^2$alkylsulfonyl and $Het^2$arylsulfonyl; aminosulfinyl, aminosulfonyl, wherein any of the above listed X groups is optionally substituted with one or more substituents independently chosen from the group comprising or consisting of: halogen, perhaloalkyl, nitro, cyano, alkyl, aryl, aralkyl, $Het^1$alkyl, $Het^2$alkyl, hydroxyl, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, $Het^1$carbonylamino, $Het^1$alkanoylamino, $Het^2$carbonylamino, $Het^2$alkanoylamino, sulfo and substituted sulfo, sulfonyl, aminosulfonyl, imino, —C(=NR')OH, —C(=NR')OR", —C(=NR')SH, —C(=NR')SR", oxo, primary amino, secondary amino, and tertiary amino, wherein the substituents in the secondary and tertiary amino are, each independently, chosen from $R^e$ and preferably $R^d$, alkylamino, dialkylamino, arylamino, aralkylamino, $Het^1$amino, $Het^1$alkylamino, $Het^2$amino and $Het^2$alkylamino, —NR'C(=O)OR", —NR'C(O)NR"R"' —NR'C(S)NR"R"', —N(OH)C(=O)OR', —NR'C(=O)SR", —N(OH)C(=O)NR'R", —N(OH)C(S)NR'R", —NR'C(O)N(OH)R", —NR'C(S)N(OH)R", —NR'S(=O)$_2$R", —NHS(=O)$_2$NR'R", —NR'S(=O)$_2$NHR", and —P(=O)(OR')(OR"), wherein R', R" and R"' are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino;

wherein $Z^1$ and $Z^2$ is, each independently, chosen from the group comprising or consisting of: hydrogen, alkyl, alkenyl, alkynyl, cycloalkyl, cycloalkylalkyl, cycloalkylalkenyl, aryl, aralkyl, arylalkenyl, $Het^1$, $Het^1$alkyl, $Het^1$alkenyl, $Het^1$cycloalkyl, $Het^1$cycloalkylalkyl, $Het^1$alkylcycloalkyl, $Het^1$alkylcycloalkylalkyl, $Het^1$aryl, $Het^1$aralkyl, $Het^1$alkylaryl, $Het^1$alkylaralkyl, $Het^2$, $Het^2$alkyl, $Het^2$alkenyl, $Het^2$cycloalkyl, $Het^2$cycloalkylalkyl, $Het^2$alkylcycloalkyl, $Het^2$alkylcycloalkylalkyl, $Het^2$aryl, $Het^2$aralkyl, $Het^2$alkylaryl $Het^2$alkylaralkyl, perhaloalkyl, wherein any of the above listed $Z^1$ and $Z^2$ groups is, each independently, optionally substituted with one or more substituents independently chosen from the group comprising or consisting of: halogen, perhaloalkyl, nitro, cyano, alkyl, aryl, aralkyl, $Het^1$alkyl, $Het^2$alkyl, hydroxyl, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, $Het^1$carbonylamino, $Het^1$alkanoylamino, $Het^2$carbonylamino, $Het^2$alkanoylamino, sulfo and substituted sulfo, sulfonyl, aminosulfonyl, imino, —C(=NR')OH, —C(=NR')OR", —C(=NR')SH, —C(=NR')SR", oxo, primary amino, secondary amino, and tertiary amino, wherein the substituents in the secondary and tertiary amino are, each independently, chosen from $R^e$ and preferably $R^d$, alkylamino, dialkylamino, arylamino, aralkylamino, $Het^1$amino, $Het^1$alkylamino, $Het^2$amino and $Het^2$alkylamino, —NR'C(=O)OR", —NR'C(O)NR"R"', —NR'C(S)NR"R"', —N(OH)C(=O)OR", —NR'C(=O)SR", —N(OH)C(=O)NR'R", —N(OH)C(S)NR'R", —NR'C(O)N(OH)R", —NR'C(S)N(OH)R", —NR'S(=O)$_2$R", —NHS(=O)$_2$NR'R", —NR'S(=O)$_2$NHR", and —P(=O)(OR')(OR"), wherein R', R" and R"' are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino.

DEFINITIONS

Throughout the present specification, articles for a singular form (e.g., "a", "an", "the", etc. in English; "ein", "der", "das", "die", etc. and their inflections in German; "un", "une", "la", "le", etc. in French; articles, adjectives, etc. in other languages) include the concept of their plurality unless otherwise mentioned. It should be also understood that the terms as used herein have definitions typically used in the art unless otherwise mentioned.

The term "comprising" as used herein is synonymous with "including" or "containing", and is inclusive or open-ended and does not exclude additional, unrecited members, elements or method steps.

The terms "specifically", "more specifically", "even more specifically", and the like, when used herein to specify lower members (e.g., subgenera and/or species) of a genus, do not indicate that an exhaustive listing of all such lower members would be provided. Accordingly, the use of these terms does not exclude additional, unrecited members of the genus.

Whenever the term "substituted" is used in the present invention, it is meant to indicate that one or more hydrogens on the atom (typically a C-, N-, O- or S-atom, usually a C-atom) indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "one or more" covers the possibility of all the available atoms, where appropriate, to be substituted, preferably, one, two or three. When any variable, e.g. halogen or alkyl, occurs more than one time in any constituent, each definition is independent.

As used herein, "—" when in between two atoms, indicates a singe bond between the said atoms; "=" when in between two atoms, indicates a double bond between the said atoms; "≡" when in between two atoms, indicates a triple bond between the said atoms.

As used herein, "—" when projecting from an atom of a substituting radical, indicates point(s) of attachment of the said substituting radical to the atom being substituted with the said radical.

As used herein, $R^a$ is hydrocarbyl, substituted hydrocarbyl or a heteroatom-linked radical, as defined herein.

As used herein, $R^e$ defines a group comprising or consisting of halogen, perhaloalkyl, haloformyl, nitro, nitroso, azido, cyano, cyanato, isocyanato, thiocyanato, isothiocyanato, alkyl, alkenyl, alkynyl, cycloalkyl, cycloalkylalkyl, cycloalkylalkenyl, aryl, aralkyl, arylalkenyl, $Het^1$, $Het^1$alkyl, $Het^1$alkenyl, $Het^1$cycloalkyl, $Het^1$cycloalkylalkyl, $Het^1$alkylcycloalkyl, $Het^1$alkylcycloalkylalkyl, $Het^1$aryl, $Het^1$aralkyl, $Het^1$alkylaryl, $Het^1$alkylaralkyl, $Het^2$, $Het^2$alkyl, $Het^2$alkenyl, $Het^2$cycloalkyl, $Het^2$cycloalkylalkyl, $Het^2$alkylcycloalkyl, $Het^2$alkylcycloalkylalkyl, $Het^2$aryl, $Het^2$aralkyl, $Het^2$alkylaryl $Het^2$alkylaralkyl, arylaminoalkyl, hydroxyl, alkoxy, aryloxy, aralkoxy, $Het^1$oxy, $Het^1$alkoxy, $Het^1$aryloxy, $Het^2$oxy, $Het^2$alkoxy and $Het^2$aryloxy, mercapto, alkylthio, arylthio, aralkylthio, $Het^1$thio, $Het^1$alkylthio, $Het^1$arylthio, $Het^2$thio, $Het^2$alkylthio, formyl, alkanoyl, cycloalkylcarbonyl, aroyl, aralkanoyl, $Het^1$carbonyl, $Het^1$alkanoyl, $Het^1$aroyl, $Het^2$carbonyl, $Het^2$alkanoyl, $Het^2$aroyl; hydroxyalkanoyl, alkoxyalkanoyl, oxoalkanoyl, aminoalkanoyl, aryloxyalkanoyl, thioformyl, alkylthiocarbonyl, arylthiocarbonyl, aralkylthiocarbonyl, $Het^1$thiocarbonyl, $Het^1$alkylthiocarbonyl, $Het^1$arylthiocarbonyl, $Het^2$thiocarbonyl, $Het^2$alkylthiocarbonyl, $Het^2$arylthiocarbonyl, formyloxy, alkanoyloxy, cycloalkylcarbonyloxy, aroyloxy, aralkanoyloxy, $Het^1$carbonyloxy, $Het^1$alkanoyloxy, $Het^2$carbonyloxy, $Het^2$alkanoyloxy, formylthio, acylthio alkanoylthio, aroylthio, aralkanoylthio, $Het^1$carbonylthio, $Het^1$alkanoylthio, $Het^2$carbonylthio and $Het^2$alkanoylthio, thioformyloxy; thioacyloxy, alkylthiocarbonyloxy, arylthiocarbonyloxy, aralkylthiocarbonyloxy, $Het^1$thiocarbonyloxy, $Het^1$alkylthiocarbonyloxy, $Het^2$thiocarbonyloxy, $Het^2$alkylthiocarbonyloxy, thioformylthio, alkylthiocarbonylthio, arylthiocarbonylthio, aralkylthiocarbonylthio, $Het^1$thiocarbonylthio, $Het^1$alkylthiocarbonylthio, $Het^2$thiocarbonylthio, $Het^2$alkylthiocarbonylthio, carboxyl, alkoxycarbonyl, cycloalkylalkoxycarbonyl, aryloxycarbonyl, aralkoxycarbonyl, $Het^1$oxycarbonyl, $Het^1$alkoxycarbonyl, $Het^1$aryloxycarbonyl, $Het^2$oxycarbonyl, $Het^2$alkoxycarbonyl, $Het^2$aryloxycarbonyl, thiocarboxyl, alkoxythiocarbonyl, aryloxythiocarbonyl, aralkoxythiocarbonyl, $Het^1$oxythiocarbonyl, $Het^1$alkoxythiocarbonyl, $Het^1$aryloxythiocarbonyl, $Het^2$oxythiocarbonyl, $Het^2$alkoxythiocarbonyl, $Het^2$aryloxythiocarbonyl, (alkylthio)carbonyl, (arylthio)carbonyl, (aralkylthio)carbonyl, ($Het^1$thio)carbonyl, ($Het^1$alkylthio)carbonyl, ($Het^1$arylthio)carbonyl, ($Het^2$thio)carbonyl, ($Het^2$alkylthio)carbonyl, ($Het^2$arylthio)carbonyl, (alkylthio)thiocarbonyl, (arylthio)thiocarbonyl, (aralkylthio)thiocarbonyl, ($Het^1$thio)thiocarbonyl, ($Het^1$alkylthio)thiocarbonyl, ($Het^1$arylthio)thiocarbonyl, ($Het^2$thio)thiocarbonyl, ($Het^2$alkylthio)thiocarbonyl, ($Het^2$arylthio)thiocarbonyl, carbamoyl, alkylcarbamoyl, cycloalkylcarbamoyl, arylcarbamoyl, aralkylcarbamoyl, $Het^1$carbamoyl, $Het^1$alkylcarbamoyl, $Het^1$arylcarbamoyl, $Het^2$carbamoyl, $Het^2$alkylcarbamoyl, $Het^2$arylcarbamoyl, thiocarbamoyl, sulfinyl; sulfonyl; aminosulfinyl; aminosulfonyl; sulfeno, sulfino, sulfo, amidino, guanidino, biguanidino, diaminomethyleneamino, ureido, thioureido, isoureido, isothioureido, amino, primary amino, secondary amino and tertiary amino, hydroxylamino, formylamino, acylamino, alkanoylamino, cycloalkylcarbonylamino, aroylamino, aralkanoylamino, $Het^1$carbonylamino, $Het^1$alkanoylamino, $Het^2$carbonylamino, $Het^2$alkanoylamino; thioformylamino; thioacylamino, alkylthiocarbonylamino, cycloalkylthiocarbonylamino, arylthiocarbonylamino, aralkylthiocarbonylamino, $Het^1$thiocarbonylamino, $Het^1$alkylthiocarbonylamino, $Het^2$thiocarbonylamino, $Het^2$alkylthiocarbonylamino, iminomethylamino, sulfinylamino and sulfonylamino radicals, as defined herein, and $R^e$ further comprises all of the above listed $R^e$ groups when optionally substituted with one or more substituents independently chosen from the group comprising or consisting of: halogen, perhaloalkyl, nitro, cyano, alkyl, aryl, aralkyl, $Het^1$alkyl, $Het^2$alkyl, hydroxyl, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, $Het^1$carbonylamino, $Het^1$alkanoylamino, $Het^2$carbonylamino, $Het^2$alkanoylamino, sulfo and substituted sulfo, sulfonyl, aminosulfonyl, imino, —C(=NR')OH, —C(=NR')OR", —C(=NR')SH, —C(=NR')SR", oxo, primary amino, secondary amino, and tertiary amino, wherein the substituents in the secondary and tertiary amino are, each independently, chosen from $R^e$ and preferably $R^d$, alkylamino, arylamino, aralkylamino, Het$^1$amino, Het$^1$alkylamino, Het$^2$amino and Het$^2$alkylamino, —NR'C(=O)OR", —NR'C(O)NR"R''', —NR'C(S)NR"R''', —N(OH)C(=O)OR", —NR'C(=O)SR", —N(OH)C(=O)NR'R", —N(OH)C(S)NR'R", —NR'C(O)N(OH)R", —NR'C(S)N(OH)R", —NR'S(=O)$_2$R", —NHS(=O)$_2$NR'R", —NR'S(=O)$_2$NHR", and —P(=O)(OR')(OR"), wherein R", R" and R''' are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino, as defined herein.

As used herein, R$^d$ defines a group comprising or consisting of hydrocarbyl and substituted hydrocarbyl radicals including perhaloalkyl, haloformyl, cyano, alkyl, alkenyl, alkynyl, cycloalkyl, cycloalkylalkyl, cycloalkylalkenyl, aryl, aralkyl, arylalkenyl, Het$^1$, Het$^1$alkyl, Het$^1$alkenyl, Het$^1$cycloalkyl, Het$^1$cycloalkylalkyl, Het$^1$alkylcycloalkyl, Het$^1$alkylcycloalkylalkyl, Het$^1$aryl, Het$^1$aralkyl, Het$^1$alkylaryl, Het$^1$alkylaralkyl, Het$^2$, Het$^2$alkyl, Het$^2$alkenyl, Het$^2$cycloalkyl, Het$^2$cycloalkylalkyl, Het$^2$alkylcycloalkyl, Het$^2$alkylcycloalkylalkyl, Het$^2$aryl, Het$^2$aralkyl, Het$^2$alkylaryl Het$^2$alkylaralkyl, arylaminoalkyl, formyl, alkanoyl, cycloalkylcarbonyl, aroyl, aralkanoyl, Het$^1$carbonyl, Het$^1$alkanoyl, Het$^1$aroyl, Het$^2$carbonyl, Het$^2$alkanoyl, Het$^2$aroyl; hydroxyalkanoyl, alkoxyalkanoyl, oxoalkanoyl, aminoalkanoyl, aryloxyalkanoyl, thioformyl, alkylthiocarbonyl, arylthiocarbonyl, aralkylthiocarbonyl, Het$^1$thiocarbonyl, Het$^1$alkylthiocarbonyl, Het$^1$arylthiocarbonyl, Het$^2$thiocarbonyl, Het$^2$alkylthiocarbonyl, Het$^2$arylthiocarbonyl, carboxyl, alkoxycarbonyl, cycloalkylalkoxycarbonyl, aryloxycarbonyl, aralkoxycarbonyl, Het$^1$oxycarbonyl, Het$^1$alkoxycarbonyl, Het$^1$aryloxycarbonyl, Het$^2$oxycarbonyl, Het$^2$alkoxycarbonyl, Het$^2$aryloxycarbonyl, thiocarboxyl, alkoxythiocarbonyl, aryloxythiocarbonyl, aralkoxythiocarbonyl, Het$^1$oxythiocarbonyl, Het$^1$alkoxythiocarbonyl, Het$^1$aryloxythiocarbonyl, Het$^2$oxythiocarbonyl, Het$^2$alkoxythiocarbonyl, Het$^2$aryloxythiocarbonyl, (alkylthio)carbonyl, (arylthio)carbonyl, (aralkylthio)carbonyl, (Het$^1$thio)carbonyl, (Het$^1$alkylthio)carbonyl, (Het$^1$arylthio)carbonyl, (Het$^2$thio)carbonyl, (Het$^2$alkylthio)carbonyl, (Het$^2$arylthio)carbonyl, (alkylthio)thiocarbonyl, (arylthio)thiocarbonyl, (aralkylthio)thiocarbonyl, (Het$^1$thio)thiocarbonyl, (Het$^1$alkylthio)thiocarbonyl, (Het$^1$arylthio)thiocarbonyl, (Het$^2$thio)thiocarbonyl, (Het$^2$alkylthio)thiocarbonyl, (Het$^2$arylthio)thiocarbonyl, carbamoyl, alkylcarbamoyl, cycloalkylcarbamoyl, arylcarbamoyl, aralkylcarbamoyl, Het$^1$carbamoyl, Het$^1$alkylcarbamoyl, Het$^1$arylcarbamoyl, Het$^2$carbamoyl, Het$^2$alkylcarbamoyl, Het$^2$arylcarbamoyl thiocarbamoyl as defined herein, and R$^d$ preferably defines a group comprising or consisting of perhaloalkyl, alkyl, alkenyl, cycloalkyl, cycloalkylalkyl, aryl, aralkyl, Het$^1$, Het$^1$alkyl, Het$^2$, Het$^2$alkyl, formyl, alkanoyl, aroyl, aralkanoyl, carboxyl, alkoxycarbonyl, aryloxycarbonyl, aralkoxycarbonyl, carbamoyl, alkylcarbamoyl, arylcarbamoyl and aralkylcarbamoyl radicals as defined herein, and R$^d$ further comprises all of the above listed R$^d$ groups when substituted with one or more substituents independently chosen from the group comprising or consisting of: halogen, perhaloalkyl, nitro, cyano, alkyl, aryl, aralkyl, Het$^1$alkyl, Het$^2$alkyl, hydroxy, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, Het$^1$carbonylamino, Het$^1$alkanoylamino, Het$^2$carbonylamino, Het$^2$alkanoylamino, sulfo and substituted sulfo, sulfonyl, aminosulfonyl, imino, —C(=NR')OH, —C(=NR')OR", —C(=NR')SH, —C(=NR')SR", oxo, primary amino, secondary amino, and tertiary amino, alkylamino, arylamino, aralkylamino, Het$^1$amino, Het$^1$alkylamino, Het$^2$amino and Het$^2$alkylamino, —NR'C(=O)OR", —NR'C(O)NR"R''', —NR'C(S)NR"R''', —N(OH)C(=O)OR', —NR'C(=O)SR", —N(OH)C(=O)NR'R", —N(OH)C(S)NR'R", —NR'C(O)N(OH)R", —NR'C(S)N(OH)R", —NR'S(=O)$_2$R", —NHS(=O)$_2$NR'R", —NR'S(=O)$_2$NHR", and —P(=O)(OR')(OR"), wherein R', R" and R''' are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino.

The terms "hydrocarbon" and "hydrocarbyl" as used herein describe organic compounds or moieties (radicals) consisting exclusively of the elements carbon and hydrogen. Hydrocarbyl moieties include alkyl, alkenyl, alkynyl, cycloalkyl and aryl radicals. Hydrocarbyl moieties also include alkyl, alkenyl, alkynyl, cycloalkyl, and aryl radicals substituted with other aliphatic, cyclic, or aromatic hydrocarbon groups, such as, e.g., alkylaryl, aralkyl, alkenaryl, arylalkenyl, alkylcycloalkyl, cycloalkylalkyl, and the like. Unless otherwise indicated, these moieties preferably comprise 1 to 20 carbon atoms.

The term "substituted hydrocarbyl" as used herein refers to hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. Examples of such substituents include halogen, Het$^1$, Het$^2$, alkoxy, alkenoxy, alkenoxy, aryloxy, hydroxy, protected hydroxy, keto, acyl, acyloxy, nitro, amino, amido, nitro, cyano, thiol, ketals, acetals, esters, ethers, and the like.

The term "heteroatom" means atoms other than carbon and hydrogen. A "heteroatom-linked radical" is one that binds to a substituted atom via a heteroatom present in the radical.

The term "alkyl", alone or as part of another group, means straight and branched chained saturated hydrocarbon radicals containing from 1 to 10 carbon atoms, preferably from 1 to 8 carbon atoms, more preferably 1 to 6 carbon atoms. Examples of such radicals include methyl, ethyl, n-propyl, isopropyl, n-butyl, isobutyl, sec-butyl, tert-butyl, 2-methylbutyl, pentyl, iso-amyl, hexyl, 3-methylpentyl, octyl and the like. The term "C$_{1-6}$alkyl", alone or as part of another group, means an alkyl as defined herein having from 1 to 6 carbon atoms such as, for example, methyl, ethyl, propyl, butyl and 2-methyl-propyl, pentyl, hexyl, 2-methylbutyl, 3-methylpentyl and the like.

The term "alkenyl", alone or as part of another group, defines straight and branched chained hydrocarbon radicals containing from 2 to about 20 carbon atoms, preferably from 2 to 8 carbon atoms, more preferably 2 to 6 carbon atoms containing at least one double bond such as, for example, ethenyl, propenyl, butenyl, pentenyl, hexenyl and the like.

The term "alkynyl", alone or as part of another group, defines straight and branched chained hydrocarbon radicals having from 2 to about 10 carbon atoms containing at least one triple bond, more preferably from 2 to about 6 carbon atoms. Examples of alkynyl radicals include ethynyl, propynyl, (propargyl), butynyl, pentynyl, hexynyl and the like.

The term "cycloalkyl", alone or as part of another group, means a saturated or partially saturated monocyclic, bicyclic or polycyclic alkyl radical wherein each cyclic moiety contains from about 3 to about 8 carbon atoms, more preferably from about 3 to about 7 carbon atoms. Examples of monocyclic cycloalkyl radicals include cyclopropyl, cyclobutyl, cyclopentyl, cyclohexyl, cycloheptyl, cyclooctyl and the like. Examples of polycyclic cycloalkyl radicals include decahydronaphthyl, bicyclo[5.4.0]undecyl, adamantyl, and the like. The term "$C_{3-7}$cycloalkyl", alone or as part of another group, means a cycloalkyl as defined herein having from 3 to 7 carbon atoms.

The term "cycloalkylalkyl", alone or as part of another group, means an alkyl radical as defined herein, in which at least one hydrogen atom on the alkyl radical is replaced by a cycloalkyl radical as defined herein. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "cycloalkylalkenyl", alone or as part of another group, means an alkenyl radical as defined herein, in which at least one hydrogen atom on the alkenyl radical is replaced by a cycloalkyl radical as defined herein. Examples of such cycloalkenylalkyl radicals include 1-cyclopentylethenyl, 1-cyclohexylethenyl, 2-cyclopentylethenyl, 2-cyclohexylethenyl, cyclobutylpropenyl, cyclopentylpropenyl, cyclopentylbutenyl, cyclohexylbutenyl and the like.

The term "alkylene", alone or as part of another group, means a bifunctional (bivalent) saturated branched or unbranched hydrocarbon radical containing from 1 to 24 carbon atoms, preferably 1 to 10 carbon atoms, more preferable 1 to 8 carbon atoms, even more preferably 1 to 6 carbon atoms. Examples of alkylene include methylene (—$CH_2$—), ethylene (—$CH_2CH_2$—), propylene (—$CH_2CH_2CH_2$—), 2-methylpropylene (—$CH_2CH(CH_3)CH_2$—), hexylene ((—$CH_2$)$_6$—), and the like. The term "$C_{1-6}$alkylene", alone or as part of another group, means an alkylene as defined herein having from 1 to 6 carbon atoms such as, for example, methylene (—$CH_2$—), ethylene (—$CH_2CH_2$—), propylene (—$CH_2CH_2CH_2$—), and the like.

The term "alkenylene", alone or as part of another group, means a bifunctional (bivalent) branched or unbranched hydrocarbon radical containing from 2 to 24 carbon atoms, preferably 2 to 8 carbon atoms, more preferably 2 to 6 carbon atoms, and at least one double bond, e.g., from 1 to 6, and typically 1 or 2 double bonds. Examples of alkenylene include ethenylene (—CH=CH—), propenylene (—CH=CHCH$_2$—), and the like.

The term "alkynylene", alone or as part of another group, means a bifunctional (bivalent) branched or unbranched hydrocarbon radical containing from 2 to 24 carbon atoms, preferably 2 to 10 carbon atoms, more preferably 2 to 8 carbon atoms, even more preferably 2 to 6 carbon atoms, and at least one triple bond, e.g., from 1 to 6, and typically 1 or 2 triple bonds. Examples of alkynylene include ethynylene (—C≡C—), propynylene (—C≡CCH$_2$—), and the like.

The term "aryl", alone or as part of another group, is meant to include phenyl and naphtyl which both may be optionally substituted with one or more substituents independently selected from alkyl, alkoxy, halogen, hydroxy, amino, nitro, cyano, haloalkyl, carboxy, alkoxycarbonyl, cycloalkyl, Het$^1$, amido, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio and methylsulfonyl; whereby the optional substituents on any amino function are independently selected from alkyl, alkyloxy, Het$^1$, Het$^1$alkyl, Het$^1$alkyl, Het$^1$oxy, Het$^1$oxyalkyl, phenyl, phenyloxy, phenyloxyalkyl, phenylalkyl, alkyloxycarbonylamino, amino, and aminoalkyl whereby each of the amino groups may optionally be mono- or where possible di-substituted with alkyl. Examples of aryl includes phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl and the like.

The term "aralkyl", alone or as part of another group, means an alkyl as defined herein, wherein an alkyl hydrogen atom is replaced by an aryl as defined herein. Examples of aralkyl radicals include benzyl, phenethyl, dibenzylmethyl, methylphenylmethyl, 3-(2-naphthyl)-butyl, and the like.

The term "arylalkenyl", alone or as part of another group, means an alkenyl as defined herein, wherein an alkenyl hydrogen atom is replaced by an aryl as defined herein. Examples of arylalkenyl radicals include phenylethenyl, diphenylethenyl, dibenzylethenyl, methylphenylethenyl, 3-(2-naphthyl)-butenyl, and the like.

The term "Het$^1$", alone or as part of another group, is defined as a saturated or partially unsaturated monocyclic, bicyclic or polycyclic heterocycle having preferably 3 to 12 ring members, more preferably 5 to 10 ring members and more preferably 5 to 6 ring members, which contains one or more heteroatom ring members selected from nitrogen, oxygen or sulfur and which is optionally substituted on one or more carbon atoms by alkyl, alkyloxy, halogen, hydroxy, oxo, optionally mono- or disubstituted amino, nitro, cyano, haloalkyl, carboxyl, alkoxycarbonyl, cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are independently selected from alkyl, alkyloxy, Het$^2$, Het$^2$alkyl, Het$^2$oxy, Het$^2$oxyalkyl, aryl, aryloxy, aryloxyalkyl, aralkyl, alkyloxycarbonylamino, amino, and aminoalkyl whereby each of the amino groups may optionally be mono- or where possible di-substituted with alkyl.

The term "Het$^1$alkyl", alone or as part of another group, means an alkyl as defined herein, wherein an alkyl hydrogen atom is replaced by Het$^1$ as defined herein.

The term "Het$^1$alkenyl", alone or as part of another group, means an alkenyl as defined herein, wherein an alkenyl hydrogen atom is replaced by Het$^1$ as defined herein.

The term "Het$^1$cycloalkyl", alone or as part of another group, means a cycloalkyl as defined herein, wherein a cycloalkyl hydrogen atom is replaced by Het$^1$ as defined herein.

The term "Het¹cycloalkylalkyl", alone or as part of another group, means an alkyl as defined herein, wherein an alkyl hydrogen atom is replaced by Het¹cycloalkyl as defined herein.

The term "Het¹alkylcycloalkyl", alone or as part of another group, means a cycloalkyl as defined herein, wherein a cycloalkyl hydrogen atom is replaced by Het¹alkyl as defined herein.

The term "Het¹alkylcycloalkylalkyl", alone or as part of another group, means an alkyl as defined herein, wherein an alkyl hydrogen atom is replaced by Het¹alkylcycloalkyl as defined herein.

The term "Het¹aryl", alone or as part of another group, means an aryl as defined herein, wherein an aryl hydrogen atom is replaced by Het¹ as defined herein.

The term "Het¹aralkyl", alone or as part of another group, means an alkyl as defined herein, wherein an alkyl hydrogen atom is replaced by Het¹aryl as defined herein.

The term "Het¹alkylaryl", alone or as part of another group, means an aryl as defined herein, wherein an aryl hydrogen atom is replaced by Het¹alkyl as defined herein.

The term "Het¹alkylaralkyl", alone or as part of another group, means an alkyl as defined herein, wherein an alkyl hydrogen atom is replaced by Het¹alkylaryl as defined herein.

The term "Het²" as a group or part of a group is defined as an aromatic monocyclic, bicyclic or tricyclic heterocycle having preferably 3 to 12 ring members, more preferably 5 to 10 ring members and more preferably 5 to 6 ring members, which contains one or more heteroatom ring members selected from nitrogen, oxygen or sulfur and which is optionally substituted on one or more carbon atoms by alkyl, alkyloxy, halogen, hydroxy, optionally mono- or disubstituted amino, nitro, cyano, haloalkyl, carboxyl, alkoxycarbonyl, cycloalkyl, optionally mono- or disubstituted aminocarbonyl, methylthio, methylsulfonyl, aryl, Het¹ and an aromatic monocyclic, bicyclic or tricyclic heterocycle having 3 to 12 ring members; whereby the optional substituents on any amino function are independently selected from alkyl, alkyloxy, Het¹, Het¹alkyl, Het¹oxy, Het¹oxyalkyl, aryl, aryloxy, aryloxyalkyl, aralkyl, alkyloxycarbonylamino, amino, and aminoalkyl whereby each of the amino groups may optionally be mono- or where possible di-substituted with alkyl.

The term "Het²alkyl", alone or as part of another group, means an alkyl as defined herein, wherein an alkyl hydrogen atom is replaced by Het² as defined herein. Examples of Het²alkyl radicals include 2-pyridylmethyl, 3-(4-thiazolyl)-propyl, and the like.

The term "Het²alkenyl", alone or as part of another group, means an alkenyl as defined herein, wherein an alkenyl hydrogen atom is replaced by Het² as defined herein.

The term "Het²cycloalkyl", alone or as part of another group, means a cycloalkyl as defined herein, wherein a cycloalkyl hydrogen atom is replaced by Het² as defined herein.

The term "Het²cycloalkylalkyl", alone or as part of another group, means an alkyl as defined herein, wherein an alkyl hydrogen atom is replaced by Het²cycloalkyl as defined herein.

The term "Het²alkylcycloalkyl", alone or as part of another group, means a cycloalkyl as defined herein, wherein a cycloalkyl hydrogen atom is replaced by Het²alkyl as defined herein.

The term "Het²alkylcycloalkylalkyl", alone or as part of another group, means an alkyl as defined herein, wherein an alkyl hydrogen atom is replaced by Het²alkylcycloalkyl as defined herein.

The term "Het²aryl", alone or as part of another group, means an aryl as defined herein, wherein an aryl hydrogen atom is replaced by Het² as defined herein.

The term "Het²aralkyl", alone or as part of another group, means an alkyl as defined herein, wherein an alkyl hydrogen atom is replaced by Het²aryl as defined herein.

The term "Het²alkylaryl", alone or as part of another group, means an aryl as defined herein, wherein an aryl hydrogen atom is replaced by Het²alkyl as defined herein.

The term "Het²alkylaralkyl", alone or as part of another group, means an alkyl as defined herein, wherein an alkyl hydrogen atom is replaced by Het²alkylaryl as defined herein.

The term "hydroxyl", alone or as part of another group, means a radical of the formula —OH.

The term "substituted hydroxyl", alone or as part of another group, means a hydroxyl radical, wherein the hydrogen atom of the hydroxyl radical is replaced by hydrocarbyl or substituted hydrocarbyl or heteroatom-linked radical as defined herein.

The term "etherified hydroxyl", alone or as part of another group, means a hydroxyl radical, wherein the hydrogen atom of the hydroxyl radical is replaced by hydrocarbyl or substituted hydrocarbyl as defined herein. Specifically, the term includes radicals of the formula —OR$^d$, wherein R$^d$ is as defined herein; even more specifically, the term includes alkoxy, aryloxy, aralkoxy, Het¹oxy, Het¹alkoxy, Het¹aryloxy, Het²oxy, Het²alkoxy, and Het²aryloxy radicals, as defined below, and the like.

The term "alkoxy" or "alkyloxy", alone or as part of another group, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy, hexyloxy and the like.

The term "aryloxy", alone or as part of another group, means an aryl ether radical of the formula —O-aryl wherein the term aryl is as defined herein.

The term "aralkoxy", alone or as part of another group, means an alkyl ether radical wherein the term alkyl is as defined above, wherein an alkyl hydrogen atom is replaced by an aryl as defined herein. Examples of aralkoxy radicals include 2-phenylethoxy, 2-phenyl-1-propoxy, and the like.

The term "Het¹oxy", alone or as part of another group, means a Het¹ ether radical of the formula Het¹ wherein the term Het¹ is as defined herein.

The term "Het¹alkoxy", alone or as part of another group, means an alkyl ether radical wherein the term alkyl is as defined above, wherein an alkyl hydrogen atom is replaced by a Het¹ as defined herein.

The term "Het¹aryloxy", alone or as part of another group, means an aryl ether radical of the formula aryl wherein the term aryl is as defined herein, wherein an aryl hydrogen atom is replaced by a Het¹ as defined herein.

The term "Het²oxy", alone or as part of another group, means a Het² ether radical of the formula —O—Het² wherein the term Het² is as defined herein. Het²oxy radicals include, for example, 4-pyridyloxy, 5-quinolyloxy, and the like.

The term "Het²alkoxy", alone or as part of another group, means an alkyl ether radical wherein the term alkyl is as defined above, wherein an alkyl hydrogen atom is replaced by a Het² as defined herein. Examples of Het²alkoxy radicals include 2-pyridylmethoxy, 4-(1-imidazolyl)-butoxy, and the like.

The term "Het²aryloxy", alone or as part of another group, means an aryl ether radical of the formula aryl wherein the term aryl is as defined herein, wherein an aryl hydrogen atom is replaced by a Het² as defined herein.

The term "aryloxyalkyl" means alkyl as defined herein, wherein an alkyl hydrogen atom is replaced by an aryloxy as defined herein. Examples of aryloxyalkyl radicals include phenoxyethyl, 4-(3-aminophenoxy)-1-butyl, and the like.

The term "aryloxyalkoxy" means alkoxy as defined herein, wherein an alkyl hydrogen atom is replaced by an aryloxy as defined herein. Examples of (aryloxy) alkoxy radicals include 2-phenoxyethoxy, 4-(3-aminophenoxy)-1-butoxy, and the like.

The term "arylthioalkoxy" means alkoxy as defined herein, wherein an alkyl hydrogen atom is replaced by an arylthio as defined herein. Examples of arylthioalkoxy radicals include 2-(phenylthio)-ethoxy, and the like.

The term "arylaminoalkoxy" means alkoxy as defined herein, wherein an alkyl hydrogen atom is replaced by an arylamino as defined herein. Examples of arylaminoalkoxy radicals include 2-(phenylamino)-ethoxy, 2-(2-naphthylamino)-1-butoxy, and the like.

The term "sulfhydryl" or "mercapto", alone or as part of another group, means a radical of the formula —SH.

The term "substituted mercapto", alone or as part of another group, means a mercapto radical, wherein the hydrogen atom of the mercapto radical is replaced by hydrocarbyl or substituted hydrocarbyl or heteroatom-linked radical as defined herein.

The term "etherified mercapto", alone or as part of another group, means a mercapto radical, wherein the hydrogen atom of the mercapto radical is replaced by hydrocarbyl or substituted hydrocarbyl as defined herein. Specifically, the term includes radicals of the formula —$SR^d$, wherein $R^d$ is as defined herein; even more specifically, the term includes alkylthio, arylthio, aralkylthio, $Het^1$thio, $Het^1$alkylthio, $Het^1$arylthio, $Het^2$thio, $Het^2$alkylthio and $Het^2$arylthio, radicals, as defined below, and the like.

The term "alkylthio", alone or as part of another group, means an alkyl thioether radical wherein the term alkyl is as defined above. Examples of suitable alkyl thioether radicals include methylthio (—$SCH_3$), ethylthio (—$SCH_2CH_3$), n-propylthio, isopropylthio, n-butylthio, iso-butylthio, sec-butylthio, tert-butylthio, hexylthio and the like.

The term "arylthio", alone or as part of another group, means an aryl thioether radical of the formula —S-aryl wherein the term aryl is as defined herein.

The term "aralkylthio", alone or as part of another group, means an alkyl thioether radical wherein the term alkyl is as defined above, wherein an alkyl hydrogen atom is replaced by an aryl as defined herein. Examples of aralkylthio radicals include 3-phenyl-2-propylthio, 2-(2-naphthyl)-ethylthio, and the like.

The term "$Het^1$thio", alone or as part of another group, means a $Het^1$ thioether radical of the formula —S-$Het^1$ wherein the term $Het^1$ is as defined herein.

The term "$Het^1$alkylthio", alone or as part of another group, means an alkyl thioether radical wherein the term alkyl is as defined above, wherein an alkyl hydrogen atom is replaced by a $Het^1$ as defined herein.

The term "$Het^1$arylthio", alone or as part of another group, means an aryl thioether radical of the formula —S-aryl wherein the term aryl is as defined herein, wherein an aryl hydrogen atom is replaced by a $Het^1$ as defined herein.

The term "$Het^2$thio", alone or as part of another group, means a $Het^2$ thioether radical of the formula —S-$Het^2$ wherein the term $Het^2$ is as defined herein. $Het^2$thio radicals include, for example, 3-pyridylthio, 3-quinolylthio, 4-imidazolylthio, and the like.

The term "$Het^2$alkylthio", alone or as part of another group, means an alkyl thioether radical wherein the term alkyl is as defined above, wherein an alkyl hydrogen atom is replaced by a $Het^2$ as defined herein. Examples of $Het^2$alkylthio radicals include 3-pyridylmethylthio, 3 (4-thiazolyl)-propylthio, and the like.

The term "$Het^2$arylthio", alone or as part of another group, means an aryl thioether radical of the formula —S-aryl wherein the term aryl is as defined herein, wherein an aryl hydrogen atom is replaced by a $Het^2$ as defined herein.

The term "aryloxyalkylthio" means alkylthio as defined herein, wherein an alkyl hydrogen atom is replaced by an aryloxy as defined herein. Examples of aryloxyalkylthio radicals include 3-phenoxypropylthio, 4-(2-fluorophenoxy)-butylthio, and the like.

The term "arylthioalkylthio" means alkylthio as defined herein, wherein an alkyl hydrogen atom is replaced by an arylthio as defined herein. Examples of arylthioalkylthio radicals include 2-(naphthylthio)-ethylthio, 3-(phenylthio)-propylthio, and the like.

The term "arylaminoalkylthio" means alkylthio as defined herein, wherein an alkyl hydrogen atom is replaced by an arylamino as defined herein. Examples of arylaminoalkylthio radicals include 2-(phenylamino)-ethylthio, 3-(2-naphthylamino)-n-propylthio, and the like.

The term "oxo", alone or as part of another group, means a radical of the formula =O. By means of example, the term "oxoalkyl" means an alkyl as defined herein, wherein two hydrogens on an alkyl carbon atom are replaced by an oxo group as defined herein; the term "oxocycloalkyl" means a cycloalkyl as defined herein, wherein two hydrogens on a cyckloalkyl carbon atom are replaced by an oxo group as defined herein; the term "oxo$Het^1$" means a $Het^1$ as defined herein, wherein two hydrogens on a $Het^1$ carbon atom are replaced by an oxo group as defined herein.

The term "carbonyl", alone or as part of another group, means a radical of the formula —C(=O)—.

The term "formyl", alone or as part of another group, refers to is an aldehyde moiety of the formula —C(=O)H.

The term "acyl", alone or as part of another group, means a radical of the formula —C(=O)$R^a$, wherein $R^a$ is as defined herein; more specifically, the term includes a radical of the formula —C(=O)$R^d$, wherein $R^d$ is as defined herein; even more specifically, the term includes alkanoyl, cycloalkylcarbonyl, aroyl, aralkanoyl, $Het^1$carbonyl, $Het^1$alkanoyl, $Het^1$aroyl, $Het^2$carbonyl, $Het^2$alkanoyl, and $Het^2$aroyl radicals, as defined below, and the like.

The term "alkanoyl" or "alkylcarbonyl", alone or as part of another group, means an acyl radical derived from an alkanecarboxylic acid, examples of which include acetyl, propionyl, butyryl, valeryl, 4-methylvaleryl, and the like.

The term "cycloalkylcarbonyl" means an acyl group derived from a monocyclic or bridged cycloalkanecarboxylic acid such as cyclopropylcarbonyl, cyclohexylcarbonyl, adamantylcarbonyl, and the like, or from a benz-fused monocyclic cycloalkanecarboxylic acid which is optionally substituted by one or more substituents selected from alkyl, alkoxy, halogen, hydroxy, amino, nitro, cyano, haloalkyl, carboxy, alkoxycarbonyl, cycloalkyl, heterocycloalkyl, alkanoylamino, amido, mono and dialkyl substituted amino, mono and dialkyl substituted amido and the like, such as 1,2,3,4-tetrahydro-2-naphthoyl, 2-acetamido-1,2,3,4-tetrahydro-2-naphthoyl.

The term "aroyl", alone or as part of another group, means an acyl radical derived from an arylcarboxylic acid, aryl having the meaning given above. Examples of such arylcarboxylic acid radicals include substituted and unsubstituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamidol-2-naphthoyl, and the like.

The term "aralkanoyl", alone or as part of another group, means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like.

The term "$Het^1$carbonyl", alone or as part of another group, means an acyl radical of the formula $Het^1$—C(=O)—, wherein the term $Het^1$ is as defined herein.

The term "$Het^1$alkanoyl", alone or as part of another group, means an acyl radical derived from an alkanecarboxylic acid, wherein a hydrogen atom of the said acid is replaced by a $Het^1$ as defined herein.

The term "$Het^1$aroyl", alone or as part of another group, means an aroyl radical as defined herein, wherein an aryl hydrogen atom is replaced by a $Het^1$ as defined herein.

The term "$Het^2$carbonyl", alone or as part of another group, means an acyl radical of the formula $Het^2$—C(=O)—, wherein the term $Het^2$ is as defined herein.

The term "$Het^2$alkanoyl", alone or as part of another group, means an acyl radical derived from an alkanecarboxylic acid, wherein a hydrogen atom of the said acid is replaced by a $Het^2$ as defined herein.

The term "$Het^2$aroyl", alone or as part of another group, means an aroyl radical as defined herein, wherein an aryl hydrogen atom is replaced by a $Het^2$ as defined herein.

The term "hydroxyalkanoyl" means an acyl group derived from a hydroxyl-substituted alkylcarboxylic acid.

The term "alkoxyalkanoyl" means an acyl group derived from an alkoxy-substituted alkylcarboxylic acid.

The term "oxoalkanoyl" means an acyl group derived from an oxo-substituted alkylcarboxylic acid.

The term "aminoalkanoyl" means an acyl group derived from an amino-substituted alkylcarboxylic acid wherein the amino group can be a primary, secondary or tertiary amino group as defined herein, such as, e.g., a secondary or tertiary amino group containing substituents selected from alkyl, aryl, aralkyl, cycloalkyl, cycloalkylalkyl radicals and the like.

The term "aryloxyalkanoyl" means an acyl radical of the formula aryl-O-alkanoyl- wherein aryl and alkanoyl are as defined herein.

The term "thiocarbonyl", alone or as part of another group, means a radical of the formula —C(=S)—.

The term "thioformyl", alone or as part of another group, refers to is an aldehyde moiety means of the formula —C(=S)H.

The term "thioacyl", alone or as part of another group, means a radical of the formula —C(=S)$R^a$, wherein $R^a$ is as defined herein; more specifically, the term includes a radical of the formula —C(=S)$R^d$, wherein $R^d$ is as defined herein; even more specifically, the term includes radicals, as defined below, and the like; even more specifically, the term includes alkylthiocarbonyl, arylthiocarbonyl, aralkylthiocarbonyl, $Het^1$thiocarbonyl, $Het^1$alkylthiocarbonyl, $Het^1$arylthiocarbonyl, $Het^2$thiocarbonyl, $Het^2$alkylthiocarbonyl, and $Het^2$arylthiocarbonyl radicals, as defined below, and the like.

The term "alkylthiocarbonyl", alone or as part of another group, means a thioacyl radical of the formula alkyl-C(=S)—, wherein the term alkyl is as defined herein, examples of which include thioacetyl, ethylthiocarbonyl, propylthiocarbonyl, and the like.

The term "arylthiocarbonyl", alone or as part of another group, means a thioacyl radical of the formula aryl-C(=S)—, aryl having the meaning as defined herein.

The term "aralkylthiocarbonyl", alone or as part of another group, means a thioacyl radical of the formula alkyl-C(=S)—, wherein the term alkyl is as defined herein, wherein an alkyl hydrogen atom is replaced by aryl as defined herein.

The term "$Het^1$thiocarbonyl", alone or as part of another group, means a thioacyl radical of the formula $Het^1$—C(=S)—, wherein the term $Het^1$ is as defined herein.

The term "$Het^1$alkylthiocarbonyl", alone or as part of another group, means a thioacyl radical of the formula alkyl-C(=S)—, wherein an alkyl hydrogen atom is replaced by a $Het^1$ as defined herein.

The term "$Het^1$arylthiocarbonyl", alone or as part of another group, means an arylthiocarbonyl radical as defined herein, wherein an aryl hydrogen atom is replaced by a $Het^1$ as defined herein.

The term "$Het^2$thiocarbonyl", alone or as part of another group, means a thioacyl radical of the formula $Het^2$—C(=S)—, wherein the term $Het^2$ is as defined herein.

The term "$Het^2$alkylthiocarbonyl", alone or as part of another group, means a thioacyl radical of the formula alkyl-C(=S)—, wherein an alkyl hydrogen atom is replaced by a $Het^2$ as defined herein.

The term "$Het^2$arylthiocarbonyl", alone or as part of another group, means an arylthiocarbonyl radical as defined herein, wherein an aryl hydrogen atom is replaced by a $Het^2$ as defined herein.

As used herein, the term "formyloxy", alone or as part of another group, means a radical of the formula —OC(=O)H.

The term "acyloxy", alone or as part of another group, means a hydroxyl radical, wherein the hydrogen atom of the hydroxyl radical is replaced by acyl as defined herein. Specifically, the term includes radicals of the formula —OC(=O)$R^a$, wherein $R^a$ is as defined herein; more specifically, the term includes radicals of the formula —OC(=O)$R^d$, wherein $R^d$ is as defined herein; even more specifically, the term includes alkanoyloxy, cycloalkylcarbonyloxy, aroyloxy, aralkanoyloxy, $Het^1$carbonyloxy, $Het^1$alkanoyloxy, $Het^2$carbonyloxy, and $Het^2$alkanoyloxy radicals, as defined below, and the like.

The term "alkanoyloxy", alone or as part of another group, means a radical of the formula —O-alkanoyl, wherein alkanoyl is as defined herein.

The term "cycloalkylcarbonyloxy", alone or as part of another group, means a radical of the formula —O-cycloalkylcarbonyl, wherein cycloalkylcarbonyl is as defined herein.

The term "aroyloxy", alone or as part of another group, means a radical of the formula —O-aroyl, wherein aroyl is as defined herein.

The term "aralkanoyloxy", alone or as part of another group, means a radical of the formula —O-aralkanoyl, wherein aralkanoyl is as defined herein.

The term "$Het^1$carbonyloxy", alone or as part of another group, means a radical of the formula —O—$Het^1$carbonyl, wherein $Het^1$carbonyl is as defined herein.

The term "$Het^1$alkanoyloxy", alone or as part of another group, means a radical of the formula —O-$Het^1$alkanoyl, wherein $Het^1$alkanoyl is as defined herein.

The term "$Het^2$carbonyloxy", alone or as part of another group, means a radical of the formula $Het^2$carbonyl, wherein $Het^2$carbonyl is as defined herein.

The term "$Het^2$alkanoyloxy", alone or as part of another group, means a radical of the formula $Het^2$alkanoyl, wherein $Het^2$alkanoyl is as defined herein.

As used herein, the term "formylthio", alone or as part of another group, means a radical of the formula —SC(=O)H.

The term "acylthio", alone or as part of another group, means a mercapto radical, wherein the hydrogen atom of the mercapto radical is replaced by acyl as defined herein.

Specifically, the term includes radicals of the formula —SC(=O)$R^a$, wherein $R^a$ is as defined herein; more specifically, the term includes radicals of the formula —SC(=O)$R^d$, wherein $R^d$ is as defined herein; even more specifically, the term includes alkanoylthio, aroylthio, aralkanoylthio, $Het^1$carbonylthio, $Het^1$alkanoylthio, $Het^2$carbonylthio and $Het^2$alkanoylthio radicals, as defined below, and the like.

The term "alkanoylthio", alone or as part of another group, means a radical of the formula —S-alkanoyl, wherein alkanoyl is as defined herein.

The term "aroylthio", alone or as part of another group, means a radical of the formula —S-aroyl, wherein aroyl is as defined herein.

The term "aralkanoylthio", alone or as part of another group, means a radical of the formula —S-aralkanoyl, wherein aralkanoyl is as defined herein.

The term "$Het^1$carbonylthio", alone or as part of another group, means a radical of the formula —S-$Het^1$carbonyl, wherein $Het^1$carbonyl is as defined herein.

The term "$Het^1$alkanoylthio", alone or as part of another group, means a radical of the formula —S-$Het^1$alkanoyl, wherein $Het^1$alkanoyl is as defined herein.

The term "$Het^2$carbonylthio", alone or as part of another group, means a radical of the formula —S-$Het^2$carbonyl, wherein $Het^2$carbonyl is as defined herein.

The term "$Het^2$alkanoylthio", alone or as part of another group, means a radical of the formula —S-$Het^2$alkanoyl, wherein $Het^2$alkanoyl is as defined herein.

As used herein, the term "thioformyloxy", alone or as part of another group, means a radical of the formula —OC(=S)H.

The term "thioacyloxy", alone or as part of another group, means a hydroxyl radical, wherein the hydrogen atom of the hydroxyl radical is replaced by thioacyl as defined herein. Specifically, the term includes radicals of the formula —OC(=S)$R^a$, wherein $R^a$ is as defined herein; more specifically, the term includes radicals of the formula —OC(=S)$R^d$, wherein $R^d$ is as defined herein; even more specifically, the term includes alkylthiocarbonyloxy, arylthiocarbonyloxy, aralkylthiocarbonyloxy, $Het^1$thiocarbonyloxy, $Het^1$alkylthiocarbonyloxy, $Het^2$thiocarbonyloxy and $Het^2$alkylthiocarbonyloxy radicals, as defined below, and the like.

The term "alkylthiocarbonyloxy", alone or as part of another group, means a radical of the formula —O-alkylthiocarbonyl, wherein alkylthiocarbonyl radical is as defined herein.

The term "arylthiocarbonyloxy", alone or as part of another group, means a radical of the formula —O-arylthiocarbonyl, wherein arylthiocarbonyl radical is as defined herein.

The term "aralkylthiocarbonyloxy", alone or as part of another group, means a radical of the formula —O— aralkylthiocarbonyl, wherein aralkylthiocarbonyl radical is as defined herein.

The term "$Het^1$thiocarbonyloxy", alone or as part of another group, means a radical of the formula —O-$Het^1$thiocarbonyl, wherein $Het^1$thiocarbonyl radical is as defined herein.

The term "$Het^1$alkylthiocarbonyloxy", alone or as part of another group, means a radical of the formula —O-$Het^1$alkylthiocarbonyl, wherein $Het^1$alkylthiocarbonyl radical is as defined herein.

The term "$Het^2$thiocarbonyloxy", alone or as part of another group, means a radical of the formula —O-$Het^2$thiocarbonyl, wherein $Het^2$thiocarbonyl radical is as defined herein.

The term "$Het^2$alkylthiocarbonyloxy", alone or as part of another group, means a radical of the formula —O-$Het^2$alkylthiocarbonyl, wherein $Het^2$alkylthiocarbonyl radical is as defined herein.

As used herein, the term "thioformylthio", alone or as part of another group, means a radical of the formula —SC(=S)H.

The term "thioacylthio", alone or as part of another group, means a mercapto radical, wherein the hydrogen atom of the mercapto radical is replaced by thioacyl as defined herein. Specifically, the term includes radicals of the formula —SC(=S)$R^a$, wherein $R^a$ is as defined herein; more specifically, the term includes radicals of the formula SSC(=S)$R^d$, wherein $R^d$ is as defined herein; even more specifically, the term includes alkylthiocarbonylthio, arylthiocarbonylthio, aralkylthiocarbonylthio, $Het^1$thiocarbonylthio, $Het^1$alkylthiocarbonylthio, $Het^2$thiocarbonylthio and $Het^2$alkylthiocarbonylthio radicals, as defined below, and the like.

The term "alkylthiocarbonylthio", alone or as part of another group, means a radical of the formula —S-alkylthiocarbonyl, wherein alkylthiocarbonyl radical is as defined herein.

The term "arylthiocarbonylthio", alone or as part of another group, means a radical of the formula —S-arylthiocarbonyl, wherein arylthiocarbonyl radical is as defined herein.

The term "aralkylthiocarbonylthio", alone or as part of another group, means a radical of the formula —S-aralkylthiocarbonyl, wherein aralkylthiocarbonyl radical is as defined herein.

The term "$Het^1$thiocarbonylthio", alone or as part of another group, means a radical of the formula —S-$Het^1$thiocarbonyl, wherein $Het^1$thiocarbonyl radical is as defined herein.

The term "$Het^1$alkylthiocarbonylthio", alone or as part of another group, means a radical of the formula —S-$Het^1$alkylthiocarbonyl, wherein $Het^1$alkylthiocarbonyl radical is as defined herein.

The term "$Het^2$thiocarbonylthio", alone or as part of another group, means a radical of the formula —S-$Het^2$thiocarbonyl, wherein $Het^2$thiocarbonyl radical is as defined herein.

The term "$Het^2$alkylthiocarbonylthio", alone or as part of another group, means a radical of the formula —S-$Het^2$alkylthiocarbonyl, wherein $Het^2$alkylthiocarbonyl radical is as defined herein.

As used herein, the term "carboxyl", alone or as part of another group, refers to an acid moiety of the formula —C(=O)OH.

The term "substituted carboxyl", alone or as part of another group, means a carboxyl radical, wherein the hydrogen atom of the carboxyl radical is replaced by hydrocarbyl or substituted hydrocarbyl or heteroatom-linked radical as defined herein.

The term "esterified carboxyl", alone or as part of another group, means a carboxyl radical, wherein the hydrogen atom of the carboxyl radical is replaced by hydrocarbyl or substituted hydrocarbyl as defined herein. Specifically, the term includes a radical of the formula —C(=O)O—R$^d$, wherein R$^d$ is as defined herein; even more specifically, the term includes alkoxycarbonyl, cycloalkylalkoxycarbonyl, aryloxycarbonyl, aralkoxycarbonyl, Het$^1$oxycarbonyl, Het$^1$alkoxycarbonyl, Het$^1$aryloxycarbonyl, Het$^2$oxycarbonyl, Het$^2$alkoxycarbonyl, and Het$^2$aryloxycarbonyl radicals, as defined below, and the like.

The term "alkoxycarbonyl", alone or as part of another group, means a radical of the formula —C(=O)O-alkyl, wherein alkyl is as defined herein. Examples include methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl and the like.

The term "cycloalkylalkoxycarbonyl", alone or as part of another group, means a radical of the formula —C(=O)O-alkyl, wherein alkyl is as defined herein, wherein an alkyl hydrogen atom is replaced by cycloalkyl as defined herein.

The term "aryloxycarbonyl", alone or as part of another group, means a radical of the formula —C(=O)O-aryl, wherein aryl is as defined herein. Examples include phenyloxycarbonyl, naphtyloxycarbonyl, and the like.

The term "aralkoxycarbonyl", alone or as part of another group, means a radical of the formula —C(=O)O-alkyl, wherein alkyl is as defined herein, wherein an alkyl hydrogen atom is replaced by an aryl as defined herein. Examples include benzyloxycarbonyl and 4-methoxyphenylmethoxycarbonyl.

The term "Het$^1$oxycarbonyl", alone or as part of another group, means a radical of the formula —C(=O)O-Het$^1$, wherein Het$^1$ is as defined herein.

The term "Het$^1$alkoxycarbonyl", alone or as part of another group, means a radical of the formula —C(=O)O-alkyl, wherein alkyl is as defined herein, wherein an alkyl hydrogen atom is replaced by Het$^1$ as defined herein.

The term "Het$^1$aryloxycarbonyl", alone or as part of another group, means a radical of the formula —C(=O)O-aryl, wherein aryl is as defined herein, wherein an aryl hydrogen atom is replaced by Het$^1$ as defined herein.

The term "Het$^2$oxycarbonyl", alone or as part of another group, means a radical of the formula —C(=O)O-Het$^2$, wherein Het$^2$ is as defined herein.

The term "Het$^2$alkoxycarbonyl", alone or as part of another group, means a radical of the formula —C(=O)O-alkyl, wherein alkyl is as defined herein, wherein an alkyl hydrogen atom is replaced by Het$^2$ as defined herein.

The term "Het$^2$aryloxycarbonyl", alone or as part of another group, means a radical of the formula —C(=O)O-aryl, wherein aryl is as defined herein, wherein an aryl hydrogen atom is replaced by Het$^2$ as defined herein.

As used herein, the term "thiocarbonyl", alone or as part of another group, refers to a carboxyl group in which one or both oxygen atoms of the carboxyl group are substituted with a sulfur atom, and which is represented by the formula —C(=O)SH, C(=S)OH and —C(=S)SH.

The term "substituted thiocarboxyl", alone or as part of another group, means a thiocarboxyl radical, wherein the hydrogen atom of the thiocarboxyl radical is replaced by hydrocarbyl or substituted hydrocarbyl or heteroatom-linked radical as defined herein.

The term "esterified thiocarboxyl", alone or as part of another group, means a thiocarboxyl radical, wherein the hydrogen atom of the thiocarboxyl radical is replaced by hydrocarbyl or substituted hydrocarbyl as defined herein. Specifically, the term includes radicals of the formula —C(=O)SR$^d$, —C(=S)OR$^d$ and —C(=S)SR$^d$, wherein R$^d$ is as defined herein; even more specifically, the term includes alkoxythiocarbonyl, aryloxythiocarbonyl, aralkoxythiocarbonyl, Het$^1$oxythiocarbonyl, Het$^1$alkoxythiocarbonyl, Het$^1$aryloxythiocarbonyl, Het$^2$oxythiocarbonyl, Het$^2$alkoxythiocarbonyl, Het$^2$aryloxythiocarbonyl, (alkylthio)carbonyl, (arylthio)carbonyl, (aralkylthio)carbonyl, (Het$^1$thio)carbonyl, (Het$^1$alkylthio)carbonyl, (Het$^1$arylthio)carbonyl, (Het$^2$thio)carbonyl, (Het$^2$alkylthio)carbonyl, (Het$^2$arylthio)carbonyl, (alkylthio)thiocarbonyl, (arylthio)thiocarbonyl, (aralkylthio)thiocarbonyl, (Het$^1$thio)thiocarbonyl, (Het$^1$alkylthio)thiocarbonyl, (Het$^1$arylthio)thiocarbonyl, (Het$^2$thio)thiocarbonyl, (Het$^2$alkylthio)thiocarbonyl, and (Het$^2$arylthio)thiocarbonyl radicals, as defined below, and the like.

The term "alkoxythiocarbonyl", alone or as part of another group, means a radical of the formula —C(=S)O-alkyl, wherein alkyl is as defined herein. Examples include methoxythiocarbonyl, ethoxythiocarbonyl, and the like.

The term "aryloxythiocarbonyl", alone or as part of another group, means a radical of the formula —C(=S)O-aryl, wherein aryl is as defined herein. Examples include phenyloxythiocarbonyl, naphtyloxythiocarbonyl, and the like.

The term "aralkoxythiocarbonyl", alone or as part of another group, means a radical of the formula —C(=S)O-alkyl, wherein alkyl is as defined herein, wherein an alkyl hydrogen atom is replaced by an aryl as defined herein. Examples include benzyloxythiocarbonyl and 4-methoxyphenylmethoxythiocarbonyl.

The term "Hetloxythiocarbonyl", alone or as part of another group, means a radical of the formula —C(=S)O-Het$^1$, wherein Het$^1$ is as defined herein.

The term "Het$^1$alkoxythiocarbonyl", alone or as part of another group, means a radical of the formula —C(=S)O-alkyl, wherein alkyl is as defined herein, wherein an alkyl hydrogen atom is replaced by Het$^1$ as defined herein.

The term "Het$^1$aryloxythiocarbonyl", alone or as part of another group, means a radical of the formula —C(=S)O-aryl, wherein aryl is as defined herein, wherein an aryl hydrogen atom is replaced by Het$^1$ as defined herein.

The term "Het$^2$oxythiocarbonyl", alone or as part of another group, means a radical of the formula —C(=S)O-Het$^2$, wherein Het$^2$ is as defined herein.

The term "Het$^2$alkoxythiocarbonyl", alone or as part of another group, means a radical of the formula —C(=S)O-alkyl, wherein alkyl is as defined herein, wherein an alkyl hydrogen atom is replaced by Het$^2$ as defined herein.

The term "Het$^2$aryloxythiocarbonyl", alone or as part of another group, means a radical of the formula —C(=S)O-aryl, wherein aryl is as defined herein, wherein an aryl hydrogen atom is replaced by Het$^2$ as defined herein.

The term "(alkylthio)carbonyl", alone or as part of another group, means a radical of the formula —C(=O)S-alkyl, wherein alkyl is as defined herein. Examples include methylmercaptocarbonyl, ethylmercaptocarbonyl, and the like.

The term "(arylthio)carbonyl", alone or as part of another group, means a radical of the formula —C(=O)S-aryl, wherein aryl is as defined herein. Examples include phenylmercaptocarbonyl, naphtylmercaptocarbonyl, and the like.

The term "(aralkylthio)carbonyl", alone or as part of another group, means a radical of the formula —C(=O)S-alkyl, wherein alkyl is as defined herein, wherein an alkyl hydrogen atom is replaced by an aryl as defined herein.

The term "(Het$^1$thio)carbonyl", alone or as part of another group, means a radical of the formula —C(=O)S-Het$^1$, wherein Het$^1$ is as defined herein.

The term "(Het$^1$alkylthio)carbonyl", alone or as part of another group, means a radical of the formula —C(=O)S- alkyl, wherein alkyl is as defined herein, wherein an alkyl hydrogen atom is replaced by Het¹ as defined herein.

The term "(Het¹arylthio)carbonyl", alone or as part of another group, means a radical of the formula —C(=O)S-aryl, wherein aryl is as defined herein, wherein an aryl hydrogen atom is replaced by Het¹ as defined herein.

The term "(Het²thio)carbonyl", alone or as part of another group, means a radical of the formula —C(=O)S-Het², wherein Het² is as defined herein.

The term "(Het²alkylthio)carbonyl", alone or as part of another group, means a radical of the formula —C(=O)S-alkyl, wherein alkyl is as defined herein, wherein an alkyl hydrogen atom is replaced by Het² as defined herein.

The term "(Het²arylthio)carbonyl", alone or as part of another group, means a radical of the formula —C(=O)S-aryl, wherein aryl is as defined herein, wherein an aryl hydrogen atom is replaced by Het² as defined herein.

The term "(alkylthio)thiocarbonyl", alone or as part of another group, means a radical of the formula —C(=S)S-alkyl, wherein alkyl is as defined herein.

The term "(arylthio)thiocarbonyl", alone or as part of another group, means a radical of the formula —C(=S)S-aryl, wherein aryl is as defined herein.

The term "(aralkylthio)thiocarbonyl", alone or as part of another group, means a radical of the formula —C(=S)S-alkyl, wherein alkyl is as defined herein, wherein an alkyl hydrogen atom is replaced by an aryl as defined herein.

The term "(Het¹thio)thiocarbonyl", alone or as part of another group, means a radical of the formula —C(=S)S-Het¹, wherein Het¹ is as defined herein.

The term "(Het¹alkylthio)thiocarbonyl", alone or as part of another group, means a radical of the formula —C(=S)S-alkyl, wherein alkyl is as defined herein, wherein an alkyl hydrogen atom is replaced by Het¹ as defined herein.

The term "(Het¹arylthio)thiocarbonyl", alone or as part of another group, means a radical of the formula —C(=S)S-aryl, wherein aryl is as defined herein, wherein an aryl hydrogen atom is replaced by Het¹ as defined herein.

The term "(Het²thio)thiocarbonyl", alone or as part of another group, means a radical of the formula —C(=S)S-Het², wherein Het² is as defined herein.

The term "(Het²alkylthio)thiocarbonyl", alone or as part of another group, means a radical of the formula —C(=S)S-alkyl, wherein alkyl is as defined herein, wherein an alkyl hydrogen atom is replaced by Het² as defined herein.

The term "(Het²arylthio)thiocarbonyl", alone or as part of another group, means a radical of the formula —C(=S)S-aryl, wherein aryl is as defined herein, wherein an aryl hydrogen atom is replaced by Het² as defined herein.

The term "carbamoyl" or "aminocarbonyl", alone or as part of another group, refers to an amide moiety of the formula —C(=O)NH₂.

The term "substituted carbamoyl", alone or as part of another group, refers to "monosubstituted carbamoyl" radicals of the formula —C(=O)sec-amino and "disubstituted carbamoyl" radicals of the formula —C(=O)tert-amino, wherein sec-amino or tert-amino are, respectively, a secondary or a tertiary amino radical as defined herein. Specifically included are, each monosubstituted and disubstituted: alkylcarbamoyl or —C(=O)alkylamino, cycloalkylcarbamoyl or —C(=O)cycloalkylamino, arylcarbamoyl or —C(=O)arylamino, aralkylcarbamoyl or —C(=O)aralkylamino, Het¹carbamoyl or —C(=O)Het¹amino, Het¹alkylcarbamoyl or —C(=O)Het¹alkylamino, Het¹arylcarbamoyl or —C(=O)Het¹arylamino, Het²carbamoyl or —C(=O)Het²amino, Het²alkylcarbamoyl or —C(=O)Het²alkylamino and Het²arylcarbamoyl or —C(=O)Het¹arylamino radicals, and the like.

The term "thiocarbamoyl" or "aminothiocarbonyl", alone or as part of another group, refers to a thioamide moiety of the formula —C(=S)NH₂.

The term "substituted thiocarbamoyl", alone or as part of another group, refers to "monosubstituted thiocarbamoyl" radicals of the formula —C(=S)sec-amino and "disubstituted thiocarbamoyl" radicals of the formula —C(=S)tert-amino, wherein sec-amino or tert-amino are, respectively, a secondary or a tertiary amino radical as defined herein. Specifically included are, each monosubstituted and disubstituted: —C(=S)alkylamino, —C(=S)cycloalkylamino, —C(=S)arylamino, —C(=S)aralkylamino, —C(=S)Het¹amino, C(=S)Het¹alkylamino, —C(=S)Het¹arylamino, —C(=S)Het²amino, —C(=S)Het²alkylamino and —C(=S)Het¹arylamino radicals, and the like.

The term "imino", alone or as part of another group, means a divalent radical of the formula =NH.

The term "substituted imino", alone or as part of another group, means an imino radical in which the imino hydrogen is replaced by a group chosen from $R^a$ as defined herein; more specifically, the term includes radicals of the formula =NR$^e$, wherein R$^e$ is as defined herein; even more specifically, the term includes radicals of the formula =NR$^d$, wherein R$^d$ is as defined herein; yet more specifically, the term includes =Nalkyl, =Naryl, =Naralkyl, =NHet¹, =NHet¹alkyl, =NHet¹aryl, =NHet², =NHet²alkyl, and =NHet²aryl radicals, and the like. Examples include methylimino, ethylimino, and the like. Further, by means of example, the term "iminoalkyl" means an alkyl as defined herein, wherein two hydrogens on an alkyl carbon atom are replaced by an imino group or a substituted imino group as defined herein, such as, by a non-limiting example, iminomethyl and (methylimino)methyl; the term "iminocycloalkyl" means a cycloalkyl as defined herein, wherein two hydrogens on a cyckloalkyl carbon atom are replaced by an imino group or a substituted imino group as defined herein; the term "iminoHet¹" means a Het¹ as defined herein, wherein two hydrogens on a Het¹ carbon atom are replaced by an imino group or a substituted imino group as defined herein.

The term "amidino", alone or as part of another group, means a radical of the formula —C(=NH)NH₂.

The term "substituted amidino", alone or as part of another group, means an amidino radical in which an amidino hydrogen is replaced by a group chosen from $R^a$ as defined herein and specifically includes "N'-substituted amidino", meaning an amidino radical in which a hydrogen on the N¹ atom of the amidino radical is replaced by a group chosen from $R^a$ as defined herein and "N²-substituted amidino", meaning an amidino radical in which a hydrogen on the N² atom of the amidino radical is replaced by a group chosen from $R^a$ as defined herein; the "N¹" and "N²" locants denote amidino nitrogen atoms as shown in the formula C(=N$^{(2)}$H)N$^{(1)}$H₂. More specifically, the term includes "monosubstituted amidino" radicals of the formula —C(=NH)NHR$^a$ (N'-monosubstituted amidino) and —C(=NR$^a$)NH₂ (N²-monosubstituted amidino), "disubstituted amidino" radicals of the formula —C(=NH)NR$^{a1}$R$^{a2}$ (N',N'-disubstituted amidino) and —C(=NR$^{a1}$)NHR$^{a2}$ (N¹,N²-disubstituted amidino) and "trisubstituted amidino" radicals of the formula —C(=NR$^{a1}$)NR$^{a2}$R$^{a3}$, wherein R$^a$ is as defined herein and R$^{a1}$, R$^{a2}$ and R$^{a3}$ are, each independently, chosen from R$^a$ as defined herein. Even more specifically, the term includes monosubstituted amidino radicals of the formula —C(=NH)

NHR$^e$ and —C(=NR$^e$)NH$_2$, disubstituted amidino radicals of the formula —C(=NH)NR$^{e1}$R$^{e2}$ and —C(=NR$^e$)NHR$^{e2}$ and trisubstituted amidino radicals of the formula —C(=NR$^e$)NR$^{e2}$R$^{a3}$, wherein R$^e$ is as defined herein and R$^{e1}$, R$^{e2}$ and R$^{e3}$ are, each independently, chosen from R$^e$ as defined herein. Yet more specifically, the term includes monosubstituted amidino radicals of the formula —C(=NH)NHR$^d$ and —C(=NR$^d$)NH$_2$, disubstituted amidino radicals of the formula —C(=NH)NR$^{d1}$R$^{d2}$ and —C(=NR$^{d1}$)NHR$^{d2}$ and trisubstituted amidino radicals of the formula —C(=NR$^{d1}$)NR$^{d2}$R$^{d3}$, wherein R$^d$ is as defined herein and R$^{d1}$, R$^{d2}$ and R$^{d3}$ are, each independently, chosen from R$^d$ as defined herein. Examples of substituted amidino radicals include N$^1$-methylamidino or —C(=NH)NHCH$_3$, N$^1$-ethylamidino or —C(=NH)NHCH$_2$CH$_3$, N$^2$-methylamidino or —C(=NCH$_3$)NH$_2$, N$^1$-ethyl-N$^2$-methylamidino or —C(=NCH$_3$)NHCH$_2$CH$_3$, N$^2$-methyl-N$^1$,N$^1$-diphenylamidino or —C(=NCH$_3$)(C$_6$H$_5$)$_2$, and the like.

The term "cyano", alone or as part of another group, means a radical of the formula —C≡N.

The term "isocyano", alone or as part of another group, means a radical of the formula —N=CH$_2$.

The term "substituted isocyano", alone or as part of another group, means an isocyano radical in which an isocyano hydrogen is replaced by a group chosen from R$^a$ as defined herein, preferably R$^e$ as defined herein and more preferably R$^d$ as defined herein, such as, by example, alkyl, aryl and aralkyl.

The term "cyanato", alone or as part of another group, means a radical of the formula —OC≡N.

The term "isocyanato", alone or as part of another group, means a radical of the formula —N=C=O.

The term "thiocyanato", alone or as part of another group, means a radical of the formula —SC≡N.

The term "isothiocyanato", alone or as part of another group, means a radical of the formula —N=C=S.

The term "sulfinyl", alone or as part of another group, includes radicals of formula —S(=O)H and —S(=O)R$^a$, wherein R$^a$ is as defined herein. Specifically, the term includes radicals of the formula —S(=O)R$^d$, wherein R$^d$ is as defined herein; more specifically, the term includes alkylsulfinyl, arysulfinyl, aralkylsulfinyl, Het$^1$sulfinyl, Het$^1$alkylsulfinyl, Het$^1$arylsulfinyl, Het$^2$sulfinyl, Het$^2$alkylsulfinyl and Het$^2$arylsulfinyl radicals, and the like.

The term "sulfonyl", alone or as part of another group, includes radicals of formula —S(=O)$_2$H and —S(=O)$_2$R$^a$, wherein R$^a$ is as defined herein. Specifically, the term includes radicals of the formula —S(=O)$_2$R$^d$, wherein R$^d$ is as defined herein; more specifically, the term includes alkylsulfonyl, arysulfonyl, aralkylsulfonyl, Het$^1$sulfonyl, Het$^1$alkylsulfonyl, Het$^1$arylsulfonyl, Het$^2$sulfonyl, Het$^2$alkylsulfonyl and Het$^2$arylsulfonyl radicals, and the like.

The term "aminosulfonyl", alone or as part of another group, means a radical of formula —S(=O)amino, wherein amino is primary amino, mono-substituted (secondary) amino, or di-substituted (tertiary) amino, as defined herein. In particular, the term includes radicals of formula —S(=O)NH$_2$, —S(=O)NHR$^e$ and —S(=O)NR$^{e1}$R$^{e2}$, wherein R$^e$ is as defined herein and R$^{e1}$ and R$^{e2}$ are, each independently, chosen from R$^e$ as defined herein.

The term "aminosulfonyl", alone or as part of another group, means a radical of formula —S(=O)$_2$-amino, wherein amino may be primary amino, mono-substituted (secondary) amino, or di-substituted (tertiary) amino, as defined herein. In particular, the term includes radicals of formula —S(=O)$_2$NH$_2$, —S(=O)$_2$NHR$^e$ and —S(=O)$_2$NR$^{e1}$R$^{e2}$, wherein R$^e$ is as defined herein and R$^{e1}$ and R$^{e2}$ are, each independently, chosen from R$^e$ as defined herein.

The term "sulfinylamino", alone or as part of another group, includes a sec-amino radical of the formula —NH-sulfinyl and a tert-amino radical having at least one sulfinyl substituent, wherein sulfinyl is as defined herein.

The term "sulfonylamino", alone or as part of another group, includes a sec-amino radical of the formula —NH-sulfonyl and a tert-amino radical having at least one sulfonyl substituent, wherein sulfonyl is as defined herein.

The term "amino", alone or as part of another group, refers to "primary amino", "secondary amino" (also "mono-substituted amino" or "sec-amino") and "tertiary amino" (also "di-substituted amino" or "tert-amino") radicals of, respectively, the formula —NH$_2$, —NHR$^a$, and —NR$^{a1}$R$^{a2}$, wherein R$^a$ is as defined herein and R$^{a1}$ and R$^{a2}$ are, each independently, chosen from R$^a$ as defined herein. Specifically, the term encompasses radicals of formula —NH$_2$, —NHR$^e$ and —NR$^{e1}$R$^{e2}$, wherein R$^e$ is as defined herein and R$^{e1}$ and R$^{e2}$ are, each independently, chosen from R$^e$ as defined herein; more specifically, the term encompasses radicals of formula —NH$_2$, —NHR$^d$ and —NR$^{d1}$R$^{d2}$, wherein R$^d$ is as defined herein and R$^{d1}$ and R$^{d2}$ are, each independently, chosen from R$^d$ as defined herein; even more specifically, the term includes alkylamino, arylamino, aralkylamino, Het$^1$amino, Het$^1$alkylamino, Het$^2$amino and Het$^2$alkylamino radicals, as defined below, and the like. Specifically included are also secondary or tertiary amine nitrogens which are members of a Het$^1$ or Het$^2$ ring. For example, the nitrogen atom may participate in a ring having 4 to 8 atoms.

The term "alkylamino", alone or as part of another group, means a secondary or tertiary amino radical, wherein a hydrogen atom of the amino radical is replaced with an alkyl as defined herein. Specifically included are secondary alkylamino radicals of the formula —NHalkyl. Examples of secondary alkylamino radicals include methylamino (—NHCH$_3$), ethylamino (—NHCH$_2$CH$_3$), n-propylamino, isopropylamino, n-butylamino, isobutylamino, sec-butylamino, tert-butylamino, n-hexylamino, and the like. Specifically included are also tertiary alkylamino radicals, such as dialkylamino radicals of the formula —N(alkyl)(alkyl), wherein the alkyl moieties may be the same or different. Examples of dialkylamino radicals include dimethylamino (—N(CH$_3$)CH$_3$), methylethylamino (—N(CH$_2$CH$_3$)CH$_3$), and the like.

The term "arylamino", alone or as part of another group, means a secondary or tertiary amino radical, wherein a hydrogen atom of the amino radical is replaced with aryl as defined herein. Examples of arylamino radicals include phenylamino and naphtylamino, and the like.

The term "aralkylamino", alone or as part of another group, means a secondary or tertiary amino radical, wherein a hydrogen atom of the amino radical is replaced with aralkyl as defined herein. Examples of aralkylamino radicals include 2-phenylmethylamino, 2-phenyl-1-propylamino, 4-phenyl-n-butylamino, and the like.

The term "Het$^1$amino", alone or as part of another group, means a secondary or tertiary amino radical, wherein a hydrogen atom of the amino radical is replaced with Het$^1$ as defined herein.

The term "Het$^1$alkylamino", alone or as part of another group, means a secondary or tertiary amino radical, wherein a hydrogen atom of the amino radical is replaced with Het$^1$alkyl as defined herein.

The term "Het$^2$-amino", alone or as part of another group, means a secondary or tertiary amino radical, wherein a hydrogen atom of the amino radical is replaced with Het$^2$ as defined herein. Het²amino radicals include, for example, 4-thiazolylamino, 2-pyridylamino, and the like.

The term "Het²alkylamino", alone or as part of another group, means a secondary or tertiary amino radical, wherein a hydrogen atom of the amino radical is replaced with Het²alkyl as defined herein. Examples of Het²alkylamino radicals include 4-pyridylmethylamino, 3 (2-furanyl)-propylamino, and the like.

The term "arylaminoalkyl" means alkyl as defined herein, wherein an alkyl hydrogen atom is replaced by an arylamino as defined herein. Examples of arylaminoalkyl radicals include phenylaminoethyl, 4-(3-methoxyphenylamino)-1-butyl, and the like.

The term "arylaminoalkylamino" means alkylamino as defined herein, wherein an alkyl hydrogen atom is replaced by an arylamino as defined herein. Examples of arylamino alkylamino radicals include 3-(naphthylamino)-propylamino, 4-(phenylamino)-1-butylamino, and the like.

The term "aryloxyalkylamino" means alkylamino as defined herein, wherein an alkyl hydrogen atom is replaced by an aryloxy as defined herein. Examples of aryloxyalkylamino radicals include 3-phenoxy-n-propylamino, 4-phenoxybutylamino, and the like.

The term "arylthioalkylamino" means alkylamino as defined herein, wherein an alkyl hydrogen atom is replaced by an arylthio as defined herein. Examples of arylthio alkylamino radicals include 2-(phenylthio)-ethylamino, and the like.

As used herein, the term "formylamino", alone or as part of another group, means an amino radical as defined herein, wherein an amino hydrogen is replaced by formyl as defined herein. Specifically, the term includes radicals of the formula —NH(C=O)H and —NR$^a$(C=O)H, more specifically —NR$^e$(C=O)H and even more specifically —NR$^d$(C=O)H.

The term "acylamino" or "amido", alone or as part of another group, means an amino radical as defined herein, wherein an amino hydrogen is replaced by acyl as defined herein and specifically includes radicals of the formula —NHacyl and —NR$^a$acyl, wherein R$^a$ and acyl are as defined herein. More specifically, the term includes radicals of the formula —NR$^e$acyl, wherein R$^e$ and acyl are as defined herein; even more specifically, the term includes radicals of the formula —NR$^d$acyl, wherein R$^d$ and acyl are as defined herein; yet more specifically, the term includes alkanoylamino, cycloalkylcarbonylamino, aroylamino, aralkanoylamino, Het¹carbonylamino, Het¹alkanoylamino, Het²carbonylamino, and Het²alkanoylamino radicals, as defined below, and the like.

The term "alkanoylamino", alone or as part of another group, includes a sec-amino radical of the formula —NH-alkanoyl and a tert-amino radical having at least one alkanoyl substituent, wherein alkanoyl is as defined herein.

The term "cycloalkylcarbonylamino", alone or as part of another group, includes a sec-amino radical of the formula —NH-cycloalkylcarbonyl and a tert-amino radical having at least one cycloalkylcarbonyl substituent, wherein cycloalkylcarbonyl is as defined herein.

The term "aroylamino", alone or as part of another group, includes a sec-amino radical of the formula —NH-aroyl and a tert-amino radical having at least one aroyl substituent, wherein aroyl is as defined herein.

The term "aralkanoylamino", alone or as part of another group, includes a sec-amino radical of the formula —NH-aralkanoyl and a tert-amino radical having at least one aralkanoyl substituent, wherein aralkanoyl is as defined herein.

The term "Het¹carbonylamino", alone or as part of another group, includes a sec-amino radical of the formula —NH-Het¹-carbonyl and a tert-amino radical having at least one Het¹-carbonyl substituent, wherein Het¹carbonyl is as defined herein.

The term "Het¹alkanoylamino", alone or as part of another group, includes a sec-amino radical of the formula —NH-Het¹alkanoyl and a tert-amino radical having at least one Het¹alkanoyl substituent, wherein Het¹alkanoyl is as defined herein.

The term "Het²carbonylamino", alone or as part of another group, includes a sec-amino radical of the formula —NH-Het²carbonyl and a tert-amino radical having at least one Het²carbonyl substituent, wherein Het²carbonyl is as defined herein.

The term "Het²alkanoylamino", alone or as part of another group, includes a sec-amino radical of the formula —NH-Het²alkanoyl and a tert-amino radical having at least one Het²alkanoyl substituent, wherein Het²alkanoyl is as defined herein.

As used herein, the term "thioformylamino", alone or as part of another group, means an amino radical as defined herein, wherein an amino hydrogen is replaced by thioformyl as defined herein. Specifically, the term includes radicals of the formula —NH(C=S)H and —NR$^a$(C=S)H, more specifically —NR$^e$(C=S)H and even more specifically —NR$^d$(C=S)H.

The term "thioacylamino", alone or as part of another group, means an amino radical as defined herein, wherein an amino hydrogen is replaced by thioacyl as defined herein and specifically includes radicals of the formula —NHthioacyl and —NR$^a$thioacyl, wherein R$^a$ and thioacyl are as defined herein. More specifically, the term includes radicals of the formula —NR$^e$thioacyl, wherein R$^e$ and thioacyl are as defined herein; even more specifically, the term includes radicals of the formula —NR$^d$thioacyl, wherein R$^d$ and thioacyl are as defined herein; yet more specifically, the term includes alkylthiocarbonylamino, cycloalkylthiocarbonylamino, arylthiocarbonylamino, aralkylthiocarbonylamino, Het¹thiocarbonylamino, Het¹alkylthiocarbonylamino, Het²thiocarbonylamino and Het²alkylthiocarbonylamino radicals, and the like.

As used herein, the term "iminomethylamino", alone or as part of another group, means a radical of the formula —NH—CH(=NH).

As used herein, the term "hydroxylamino" means a radical of the formula —NHOH.

The term "urea" refers to organic compound of the formula NH$_2$C(=O)NH$_2$.

The term "ureido", alone or as part of another group, means a urea group of the formula —NHC(=O)NH$_2$.

The term "thiourea" refers to organic compound of the formula NH$_2$C(=S)NH$_2$.

The term "thioureido", alone or as part of another group, means a urea group of the formula —NHC(=S)NH$_2$.

The term "isourea" refers to organic compound of the formula NH$_2$C(=NH)OH.

The term "isoureido", alone or as part of another group, refers to an isourea group and specifically includes radicals of the formula —NHC(=NH)OH ("1-isoureido"), —OC(=NH)NH$_2$ ("2-isoureido") and —N=C(OH)—NH$_2$ ("3-isoureido").

The term "isothiourea" refers to organic compound of the formula NH$_2$C(=NH)SH.

The term "isothioureido", alone or as part of another group, refers to an isothiourea group and specifically includes radicals of the formula —NHC(=NH)SH ("1-isothioureido"), —SC(=NH)NH$_2$ ("2-isothioureido") and —N=C(SH)—NH$_2$ ("3-isothioureido").

The term "guanidine" refers to the imide of urea with the formula $NH_2C(=NH)NH_2$.

The term "guanidino", alone or as part of another group, means a guanidine group of the formula $-NHC(=NH)NH_2$.

The term "substituted guanidino", alone or as part of another group, means a guanidino radical in which a guanidino hydrogen is replaced by a group chosen from $R^a$ as defined herein and specifically includes "$N^1$-substituted guanidino", meaning a guanidino radical in which a hydrogen on the $N^1$ atom of the guanidino radical is replaced by a group chosen from $R^a$ as defined herein, "$N^2$-substituted guanidino", meaning a guanidino radical in which a hydrogen on the $N^2$ atom of the guanidino radical is replaced by a group chosen from $R^a$ as defined herein, and "$N^3$-substituted guanidino", meaning an guanidino radical in which a hydrogen on the $N^3$ atom of the guanidino radical is replaced by a group chosen from $R^a$ as defined herein; the "$N^1$", "$N^2$" and "$N^3$" locants denote guanidino nitrogen atoms as shown in the formula $-N^{(1)}HC(=N^{(2)}H)N^{(3)}H_2$. More specifically, the term includes "monosubstituted guanidino" radicals of the formula $-NR^aC(=NH)NH_2$ (N'-monosubstituted guanidino), $-NHC(=NR^a)NH_2$ ($N^2$-monosubstituted guanidino) and $-NHC(=NH)NHR^a$ ($N^3$-monosubstituted guanidino), "disubstituted guanidino" radicals of the formula $-NR^{a1}C(=NR^{a2})NH_2$ ($N^1,N^2$-disubstituted guanidino), $-NR^{a1}C(=NH)NHR^{a2}$ ($N^1,N^3$-disubstituted guanidino) and $-NHC(=NR^{a1})NHR^{a2}$ ($N^2,N^3$-disubstituted guanidino), "trisubstituted guanidino" radicals of the formula $-NR^{a1}C(=NR^{a2})NHR^{a3}$ ($N^1,N^2,N^3$-trisubstituted guanidino), $-NR^{a1}C(=NH)NR^{a2}R^{a3}$ (N',$N^3$,$N^3$-trisubstituted guanidino) and $-NHC(=NR^{a1})NR^{a2}R^{a3}$ ($N^2,N^3,N^3$-trisubstituted guanidino) and "tetrasubstituted guanidino" radicals of the formula $-NR^{a1}C(=NR^{a2})NR^{a3}R^{a4}$, wherein $R^a$ is as defined herein and $R^{a1}$, $R^{a2}$, $R^{a3}$ and $R^{a4}$ are, each independently, chosen from $R^a$ as defined herein. Even more specifically, the term includes monosubstituted guanidino radicals of the formula $-NR^eC(=NH)NH_2$, $-NHC(=NR^e)NH_2$ and $-NHC(=NH)NHR^e$, disubstituted guanidino radicals of the formula $-NR^{e1}C(=NR^{e2})NH_2$, $-NR^{e1}C(=NH)NHR^{e2}$ and $-NHC(=NR^{e1})NHR^{e2}$, trisubstituted guanidino radicals of the formula $-NR^{e1}C(=NR^{e2})NHR^{e3}$, $-NR^{e1}C(=NH)NR^{e2}R^{e3}$ and $-NHC(=NR^{e1})NR^{e2}R^{e3}$ and tetrasubstituted guanidino radicals of the formula $-NR^{e1}C(=NR^{e2})NR^{e3}R^{e4}$, wherein $R^e$ is as defined herein and $R^{e1}$, $R^{e2}$, $R^{e3}$ and $R^{e4}$ are, each independently, chosen from $R^e$ as defined herein. Even more specifically, the term includes monosubstituted guanidino radicals of the formula $-NR^dC(=NH)NH_2$, $-NHC(=NR^d)NH_2$ and $-NHC(=NH)NHR^d$, disubstituted guanidino radicals of the formula $-NR^{d1}C(=NR^{d2})NH_2$, $-NR^{d1}C(=NH)NHR^{d2}$ and $-NHC(=NR^{d1})NHR^{d2}$, trisubstituted guanidino radicals of the formula $-NR^{d1}C(=NR^{d2})NHR^{d3}$, $-NR^{d1}C(=NH)NR^{d2}R^{d3}$ and $-NHC(=N R^{d1})NR^{d2}R^{d3}$ and tetrasubstituted guanidino radicals of the formula $-NR^{d1}C(=NR^{d2})NR^{d3}R^{d4}$, wherein $R^d$ is as defined herein and $R^{d1}$, $R^{d2}$, $R^{d3}$ and $R^{d4}$ are, each independently, chosen from $R^d$ as defined herein.

The term "biguanidine" refers to an organic compound of the formula $NH_2C(=NH)NHC(=NH)NH_2$.

The term "biguanidino", alone or as part of another group, means a biguanidine radical group, such as, e.g., of the formula $-NHC(=NH)NHC(=NH)NH_2$ or $-N(C(=N)NH_2)_2$.

The term "diaminomethyleneamino", alone or as part of another group, means a guanidine group of the formula $-N=C(NH_2)_2$.

As used herein, the term "halo" or "halogen", alone or as part of another group, is generic for fluoro, chloro, bromo or iodo.

The term "haloalkyl", alone or as part of another group, means an alkyl radical as defined herein, wherein one or more alkyl hydrogens are replaced with a halogen, preferably chloro or fluoro atoms, more preferably fluoro atoms. Examples of such haloalkyl radicals include chloromethyl, 1-bromoethyl, fluoromethyl, difluoromethyl, trifluoromethyl, 1,1,1-trifluoroethyl and the like.

The term "perhaloalkyl", alone or as part of another group, means an alkyl radical as defined herein, wherein all alkyl hydrogens are replaced with a halogen, preferably chloro or fluoro atoms, more preferably fluoro atoms. Examples of such perhaloalkyl radicals include trichloromethyl ($-CCl_3$), trifluoromethyl ($-CF_3$), perchloroethyl ($-CCl_2CCl_3$), perfluoroethyl ($-CF_2CF_3$), perfluoropropyl, and the like.

The term "perhaloalkoxy", alone or as part of another group, means an alkoxy radical as defined herein, wherein all alkoxy hydrogens are replaced with a halogen, preferably chloro or fluoro atoms, more preferably fluoro atoms. Examples of such perhaloalkoxy radicals include trichloromethoxy ($-OCCl_3$), trifluoromethoxy ($-OCF_3$), perchloroethoxy ($-OCCl_2CCl_3$), perfluoroethoxy ($-OCF_2CF_3$), and the like.

The term "haloformyl", alone or as part of another group, means a formyl radical as defined herein, wherein the formyl hydrogen atom is replaced with a halogen as defined herein, preferably chloro or fluoro atoms, more preferably a fluoro atom, such as, e.g., chloroformyl ($-COCl$) and fluoroformyl ($-COF$).

The term "nitroso", alone or as part of another group, means a radical of the formula $-NO$.

The term "nitro", alone or as part of another group, means a radical of the formula $-NO_2$.

The term "azido", alone or as part of another group, means a radical of the formula $-N_3$.

The term "sulfeno", alone or as part of another group, means a radical of the formula $-SOH$.

The term "substituted sulfeno", alone or as part of another group, means a sulfeno radical as defined herein, wherein the hydrogen atom of the sulfeno radical is replaced by, as defined herein, $R^a$, preferably $R^e$ and more preferably $R^d$, such as, e.g., alkyl, aryl, aralkyl and the like. Examples of substituted sulfeno include methylsulfeno or $-SOCH_3$, ethylsulfeno or $-SOCH_2CH_3$, and the like.

The term "sulfino", alone or as part of another group, means a radical of the formula $-S(=O)OH$.

The term "substituted sulfino", alone or as part of another group, means a sulfino radical as defined herein, wherein the hydrogen atom of the sulfino radical is replaced by, as defined herein, $R^a$, preferably $R^e$ and more preferably $R^d$, such as, e.g., alkyl, aryl, aralkyl and the like. Examples of substituted sulfino include methylsulfino or $-S(=O)OCH_3$, ethylsulfeno or $-S(=O)OCH_2CH_3$, and the like.

The term "sulfo", alone or as part of another group, means a radical of the formula $-S(=O)_2OH$.

The term "substituted sulfo", alone or as part of another group, means a sulfo radical as defined herein, wherein the hydrogen atom of the sulfo radical is replaced by, as defined herein, $R^a$, preferably $R^e$ and more preferably $R^d$, such as, e.g., alkyl, aryl, aralkyl and the like. Examples of substituted sulfo include methylsulfo or $-S(=O)_2OCH_3$, ethylsulfeno or $-S(=O)_2OCH_2CH_3$, and the like.

Wherever an N-atom as indicated herein is substituted by two substituents, such as, e.g., in the radicals $-NR^{a1}R^{a2}$, $-NR^{e1}R^{e2}$, $-NR^{d1}R^{d2}$, $-NR'R"$, etc., this also encompasses radicals in which the two substituents, taken together with the N-atom, form a cyclic ring system, in particular Het$^1$.

As used herein, the term "alpha-amino acid" refers to an amino-substituted carboxylic acid in which an amino group, particularly a primary or a secondary amino group, and typically a primary amino group, is attached to the alpha-carbon atom which is directly attached to the carboxyl group specifying the amino-substituted carboxylic acid. As used herein, the term "amino acid" refers to all naturally occurring alpha-amino acids, in both their D and L stereoisomeric forms, their analogs and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine materials to form cystine. As used herein, the term "naturally-occurring amino acid" refers to all alpha-amino acids which normally occur in nature, in both their D and L stereoisomeric forms, irrespective of the manner in which they were prepared (e.g., isolation from a biological sample, synthetic process or microbiological process). As used herein, the term "L-amino acid" refers to an amino acid in its L-stereoisomeric form. As used herein, the term "D-amino acid" refers to an amino acid in its D-stereoisomeric form.

As used herein, the term "peptide" refers to a linear compound that consists of two or more amino acids as defined herein that are linked by means of a peptide bond. Specifically, the term encompasses peptides consisting of two or more naturally-occurring amino acids as defined herein. Specifically, the term also encompasses peptides consisting of only L-amino acids, or only of D-amino acids, or of a combination of L- and D-amino acids. In particular, the term encompasses peptides consisting of 2 to 10, more specifically 2 to 5, even more specifically 2 or 3 amino acids.

As used herein, the term "peptidyl", alone or as part of another group, denotes an acyl radical derived from a peptide as defined herein.

This invention also envisions the quaternization of the nitrogen atoms of the present compounds. A basic nitrogen can be quaternized with any agent known to those of ordinary skill in the art including, for instance, lower alkyl halides, dialkyl sulfates, long chain halides and aralkyl halides.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8th ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference. Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

It is clear to a person skilled in the art that the compounds of formula (I) contain at least one asymmetric center and thus may exist as different stereoisomeric forms.

This asymmetric center is indicated with a asterisk (*) in the figure below.

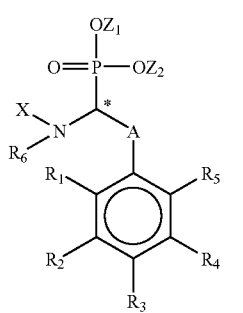

(I)

The absolute configuration of each asymmetric center that may be present in the compounds of formula (I) may be indicated by the stereochemical descriptors R and S, this R and S notation corresponding to the rules described in Pure Appl. Chem. 1976, 45, 11 30. The carbon atom marked with the asterisk (*) preferably has the R configuration.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues.

PREFERRED EMBODIMENTS OF THE COMPOUNDS

Hereinbelow, special groups of compounds of formula (I) are described with reference to preferred groups of substituents. It shall be appreciated that the invention also includes special groups of compounds defined by any combination of the preferred groups of two or more substituents as defined below.

A special group of compounds are those compounds of formula (I) wherein the said at least one of the substituents $R^1$, $R^2$, $R^3$, $R^4$ and $R^5$ is independently chosen from the group comprising or consisting of: amidino; substituted amidino, such as monosubstituted amidino, disubstituted amidino and trisubstituted amidino, preferably monosubstituted amidino or disubstituted amidino, more preferably monosubstituted amidino, wherein the substituents in the substituted amidino are, each independently, chosen from the group comprising or consisting of perhaloalkyl, alkyl, aryl, aralkyl, alkanoyl, aroyl, aralkanoyl, alkyloxycarbonyl and aralkyloxycarbonyl, optionally substituted with one or more substituents chosen from the group comprising or consisting of halogen, hydroxyl, oxo, alkyl, aryl and aralkyl; guanidino; substituted guanidino, such as monosubstituted guanidino, disubstituted guanidino, trisubstituted guanidino and tetrasubstituted guanidino, preferably monosubstituted guanidino or disubstituted guanidino, more preferably monosubstituted guanidino, wherein the substituents in the substituted guanidino are, each independently, chosen from the group comprising or consisting of perhaloalkyl, alkyl, aryl, aralkyl, alkanoyl, aroyl, aralkanoyl, alkyloxycarbonyl and aralkyloxycarbonyl, optionally substituted with one or more substituents chosen from the group comprising or consisting of halogen, hydroxyl, oxo, alkyl, aryl and aralkyl.

Also a special group of compounds are those compounds of formula (I) wherein the said at least one of the substituents $R^1$, $R^2$, $R^3$, $R^4$ and $R^5$ is independently chosen from the group comprising or consisting of: amidino and guanidino.

A yet another special group of compounds are those compounds of formula (I) wherein the said at least one of the substituents $R^1$, $R^2$, $R^3$, $R^4$ and $R^5$ is amidino.

Another special group of compounds are those compounds of formula (I) wherein the said at least one of the substituents $R^1$, $R^2$, $R^3$, $R^4$ and $R^5$ is guanidino.

Another special group of compounds are those compounds of formula (I) wherein at least $R^3$ is amidino.

Another special group of compounds are those compounds of formula (I) wherein $R^3$ is amidino.

Another special group of compounds are those compounds of formula (I) wherein at least $R^3$ is guanidino.

Another special group of compounds are those compounds of formula (I) wherein $R^3$ is guanidino.

Another special group of compounds are those compounds of formula (I) wherein A is chosen from the group comprising or consisting of a direct bond and $C_{1-6}$alkylene, more preferably A is chosen from the group comprising or consisting of a direct bond, methylene and ethylene, wherein the said $C_{1-6}$alkylene, methylene or ethylene is optionally substituted by one or more methyl or ethyl, and yet more preferably, A is methylene.

Another special group of compounds are those compounds of formula (I) wherein $R^6$ is chosen from the group comprising or consisting of hydrogen, alkyl and aralkyl, preferably $R^6$ is chosen from the group comprising or consisting of hydrogen, $C_{1-6}$alkyl and aryl$C_{1-6}$alkyl, more preferably $R^6$ is chosen from the group comprising or consisting of hydrogen and $C_{1-6}$alkyl, and even more preferably $R^6$ is hydrogen;

A further special group of compounds are those compounds of formula (I) wherein, with the proviso that X is not peptidyl, X is chosen from the group comprising or consisting of: hydrogen, alkyl, $C_{1-6}$alkyl, aryl, aralkyl, perhaloalkyl, formyl, alkanoyl, aroyl, aralkanoyl, alkoxyalkanoyl, oxoalkanoyl, aminoalkanoyl, aryloxyalkanoyl, alkoxycarbonyl, aryloxycarbonyl, aralkoxycarbonyl, alkoxythiocarbonyl, aryloxythiocarbonyl, aralkoxythiocarbonyl, (alkylthio)carbonyl, (arylthio)carbonyl, (aralkylthio)carbonyl, (alkylthio)thiocarbonyl, (arylthio)thiocarbonyl, (aralkylthio)thiocarbonyl, carbamoyl, alkylcarbamoyl, arylcarbamoyl, aralkylcarbamoyl, thiocarbamoyl, alkylthiocarbamoyl, arylthiocarbamoyl, aralkylthiocarbamoyl, alkylsulfinyl, arysulfinyl, aralkylsulfinyl, alkylsulfonyl, arysulfonyl, aralkylsulfonyl, aminosulfinyl and aminosulfonyl, wherein any of the above listed X groups is optionally substituted with one or more substituents independently chosen from the group comprising or consisting of: halogen, perhaloalkyl, nitro, cyano, alkyl, aryl, aralkyl, Het$^1$alkyl, Het$^2$alkyl, hydroxyl, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, Het$^1$carbonylamino, Het$^1$alkanoylamino, Het$^2$carbonylamino, Het$^2$alkanoylamino, sulfo and substituted sulfo, sulfonyl, aminosulfonyl, imino, —C(=NR')OH, —C(=NR')OR", —C(=NR')SH, —C(=NR')SR", oxo, primary amino, alkylamino, dialkylamino, arylamino, aralkylamino, Het$^1$amino, Het$^1$alkylamino, Het$^2$amino and Het$^2$alkylamino, —NR'C(=O)OR", —NR'C(O)NR"R''', —NR'C(S)NR"R''', —N(OH)C(=O)OR", —NR'C(=O)SR", —N(OH)C(=O)NR'R", —N(OH)C(S)NR'R", —NR'C(O)N(OH)R", —NR'C(S)N(OH)R", —NR'S(=O)$_2$R", —NHS(=O)$_2$NR'R", —NR'S(=O)$_2$NHR", and —P(=O)(OR)(OR"), wherein R", R" and R''' are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino;

Also a special group of compounds are those compounds of formula (I) wherein, with the proviso that X is not peptidyl, X is chosen from the group comprising or consisting of: hydrogen, $C_{1-6}$alkyl, aryl, aralkyl, perhaloalkyl, formyl, alkanoyl, aroyl, aralkanoyl, alkoxycarbonyl, aryloxycarbonyl, aralkoxycarbonyl, carbamoyl, alkylcarbamoyl, arylcarbamoyl, aralkylcarbamoyl, alkylsulfinyl, arysulfinyl, aralkylsulfinyl, alkylsulfonyl, arylsulfonyl, aralkylsulfonyl, aminosulfinyl and aminosulfonyl, optionally substituted with one or more substituents independently chosen from the group comprising or consisting of: halogen, perhaloalkyl, nitro, cyano, alkyl, aryl, aralkyl, Het$^1$alkyl, Het$^2$alkyl, hydroxyl, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, Het$^1$carbonylamino, Het$^1$alkanoylamino, Het$^2$carbonylamino, Het$^2$alkanoylamino, sulfo and substituted sulfo, sulfonyl, aminosulfonyl, imino, —C(=NR')OH, —C(=NR')OR", —C(=NR')SH, —C(=NR')SR", oxo, primary amino, alkylamino, dialkylamino, arylamino, aralkylamino, Het$^1$amino, Het$^1$alkylamino, Het$^2$amino and Het$^2$alkylamino, —NR'C(=O)OR", —NR'C(O)NR"R''', —NR'C(S)NR"R''', —N(OH)C(=O)OR", —NR'C(=O)SR", —N(OH)C(=O)NR'R", —N(OH)C(S)NR'R", —NR'C(O)N(OH)R", —NR'C(S)N(OH)R", —NR'S(=O)$_2$R", —NHS(=O)$_2$NR'R", —NR'S(=O)$_2$NHR", and —P(=O)(OR)(OR"), wherein R", R" and R''' are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino.

Another special group of compounds are those compounds of formula (I) wherein, with the proviso that X is not peptidyl, X is chosen from the group comprising or consisting of: hydrogen, $C_{1-6}$alkyl, aryl, aralkyl, perhaloalkyl, formyl, alkanoyl, aroyl, aralkanoyl, alkoxycarbonyl, aryloxycarbonyl, aralkoxycarbonyl, carbamoyl, alkylcarbamoyl, arylcarbamoyl, aralkylcarbamoyl, alkylsulfinyl, arysulfinyl, aralkylsulfinyl, alkylsulfonyl, arylsulfonyl, aralkylsulfonyl, aminosulfinyl and aminosulfonyl, optionally substituted with one or more substituents independently chosen from the group comprising or consisting of: halogen, perhaloalkyl, oxo, alkyl, aryl, aralkyl, alkoxy, aryloxy, aralkoxy, alkanoyl, aroyl, aralkanoyl, alkanoyloxy, aroyloxy, aralkanoyloxy, alkoxycarbonyl, aryloxycarbonyl, aralkoxycarbonyl, primary amino, alkylamino, dialkylamino, arylamino, and aralkylamino.

Another special group of compounds are those compounds of formula (I) wherein, with the proviso that X is not peptidyl, X is chosen from the group comprising or consisting of: hydrogen, $C_{1-6}$alkyl, aryl, aralkyl, perhaloalkyl, formyl, alkanoyl, aroyl, aralkanoyl, alkoxycarbonyl, aryloxycarbonyl, aralkoxycarbonyl, carbamoyl, alkylcarbamoyl, arylcarbamoyl, aralkylcarbamoyl, alkylsulfinyl, arysulfinyl, aralkylsulfinyl, alkylsulfonyl, arylsulfonyl, aralkylsulfonyl, aminosulfinyl and aminosulfonyl, optionally substituted with one or more substituents independently chosen from the group comprising or consisting of: halogen, perhaloalkyl, oxo, alkyl, aralkyl, alkoxy and aralkoxy.

Another special group of compounds are those compounds of formula (I) wherein X is chosen from the group comprising or consisting of: hydrogen, $C_{1-6}$alkyl, aryl, aralkyl, perhaloalkyl, formyl, alkanoyl, aroyl, aralkanoyl, alkoxycarbonyl, aryloxycarbonyl, aralkoxycarbonyl, carbamoyl, alkylcarbamoyl, arylcarbamoyl, aralkylcarbamoyl, alkylsulfinyl, arysulfinyl, aralkylsulfinyl, alkylsulfonyl, arylsulfonyl, aralkylsulfonyl, aminosulfinyl and aminosulfonyl.

A further special group of compounds are those compounds of formula (I) wherein $Z^1$ and $Z^2$ is, each independently, chosen from the group comprising or consisting of: alkyl, preferably $C_{1-6}$alkyl, aryl, aralkyl, preferably aryl$C_{1-6}$alkyl, and perhaloalkyl, wherein any of the above listed $Z^1$ and $Z^2$ groups is, each independently, optionally substituted with one or more substituents independently chosen from the group comprising or consisting of: halogen, perhaloalkyl, nitro, cyano, alkyl, aryl, aralkyl, Het¹alkyl, Het²alkyl, hydroxyl, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, Het¹carbonylamino, Het¹alkanoylamino, Het²carbonylamino, Het²alkanoylamino, sulfo and substituted sulfo, sulfonyl, aminosulfonyl, —C(=NR')OH, —C(=NR')OR", —C(=NR')SH, —C(=NR')SR", oxo, primary amino, alkylamino, dialkylamino, arylamino, aralkylamino, Het¹amino, Het¹alkylamino, Het²-amino and Het²alkylamino, —NR'C(=O)OR", —NR'C(O)NR"R'", —NR'C(S)NR"R'", —N(OH)C(=O)OR", —NR'C(=O)SR", —N(OH)C(=O)NR'R", —N(OH)C(S)NR'R", —NR'C(O)N(OH)R", —NR'C(S)N(OH)R", —NR'S(=O)₂R", —NHS(=O)₂NR'R", —NR'S(=O)₂NHR", and —P(=O)(OR')(OR"), wherein R", R' and R" are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino;

Another special group of compounds are those compounds of formula (I) wherein $Z^1$ and $Z^2$ is, each independently, chosen from the group comprising or consisting of: alkyl, preferably $C_{1-6}$alkyl, aryl, aralkyl, preferably aryl$C_{1-6}$alkyl, and perhaloalkyl, wherein any of the above listed $Z^1$ and $Z^2$ groups is, each independently, optionally substituted with one or more substituents independently chosen from the group comprising or consisting of: halogen, perhaloalkyl, oxo, alkyl, aryl, aralkyl, alkoxy, aryloxy, aralkoxy, alkanoyl, aroyl, aralkanoyl, alkanoyloxy, aroyloxy, aralkanoyloxy, alkoxycarbonyl, aryloxycarbonyl, aralkoxycarbonyl, primary amino, alkylamino, dialkylamino, arylamino, and aralkylamino.

Another special group of compounds are those compounds of formula (I) wherein $Z^1$ and $Z^2$ is, each independently, chosen from the group comprising or consisting of: alkyl, preferably $C_{1-6}$alkyl, aryl, aralkyl, preferably aryl$C_{1-6}$alkyl, and perhaloalkyl, wherein any of the above listed $Z^1$ and $Z^2$ groups is, each independently, optionally substituted with one or more substituents independently chosen from the group comprising or consisting of: halogen, perhaloalkyl, oxo, alkyl, aralkyl, alkoxy and aralkoxy.

Another special group of compounds are those compounds of formula (I) wherein $Z^1$ and $Z^2$ is, each independently, chosen from the group comprising or consisting of: alkyl, preferably $C_{1-6}$alkyl, aryl, aralkyl, preferably aryl$C_{1-6}$alkyl, and perhaloalkyl.

A further special group of compounds are those compounds of formula (I) wherein $Z^1$ and $Z^2$ is, each independently, chosen from the group comprising or consisting of: aryl, preferably phenyl or naphtyl, more preferably phenyl, wherein any of the above listed $Z^1$ and $Z^2$ groups is, each independently, optionally substituted with one or more substituents independently chosen from the group comprising or consisting of: halogen, perhaloalkyl, nitro, cyano, alkyl, aryl, aralkyl, Het¹alkyl, Het²alkyl, hydroxyl, alkoxy, aryloxy, aralkoxy, —OC(=NR')R", mercapto, alkylthio, arylthio, aralkylthio, —SC(=NR')R", formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, Het¹carbonylamino, Het¹alkanoylamino, Het²carbonylamino, Het²alkanoylamino, sulfo and substituted sulfo, sulfonyl, aminosulfonyl, —C(=NR')OH, —C(=NR')OR", —C(=NR')SH, —C(=NR')SR", primary amino, alkylamino, dialkylamino, arylamino, aralkylamino, Het¹amino, Het¹alkylamino, Het²-amino and Het²alkylamino, —NR'C(=O)OR", —NR'C(O)NR"R'", —NR'C(S)NR"R'", —N(OH)C(=O)OR", —NR'C(=O)SR", —N(OH)C(=O)NR'R", —N(OH)C(S)NR'R", —NR'C(O)N(OH)R", —NR'C(S)N(OH)R", —NR'S(=O)₂R", —NHS(=O)₂NR¹R", —NR'S(=O)₂NHR", and —P(=O)(OR')(OR"), wherein R", R" and R'" are, each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino;

A further special group of compounds are those compounds of formula (I) wherein $Z^1$ and $Z^2$ is, each independently, chosen from the group comprising or consisting of: aryl, preferably phenyl or naphtyl, more preferably phenyl, wherein any of the above listed $Z^1$ and $Z^2$ groups is, each independently, optionally substituted with one or more substituents independently chosen from the group comprising or consisting of: halogen, perhaloalkyl, alkyl, aryl, aralkyl, alkoxy, aryloxy, aralkoxy, alkanoyl, aroyl, aralkanoyl, alkanoyloxy, aroyloxy, aralkanoyloxy, alkoxycarbonyl, aryloxycarbonyl, aralkoxycarbonyl, primary amino, alkylamino, dialkylamino, arylamino, and aralkylamine, alkanoylamino, cycloalkylcarbonylamino, aroylamino, and aralkanoylamino.

Another special group of compounds are those compounds of formula (I) wherein $Z^1$ and $Z^2$ is, each independently, chosen from the group comprising or consisting of: aryl, preferably phenyl or naphtyl, more preferably phenyl, and aralkyl, wherein any of the above listed $Z^1$ and $Z^2$ groups is, each independently, optionally substituted with one or more substituents independently chosen from the group comprising or consisting of: halogen, alkyl, preferably $C_{1-6}$alkyl, perhaloalkyl, alkoxy, alkanoyl, alkanoyloxy, alkoxycarbonyl and alkanoylamino.

Another special group of compounds are those compounds of formula (I) wherein $Z^1$ and $Z^2$ is, each independently, chosen from the group comprising or consisting of aryl, preferably phenyl or naphtyl, more preferably phenyl.

A further special group of compounds are those compounds of formula (I) wherein $Z^1$ and $Z^2$ is, each independently, chosen from the group comprising or consisting of aryl, preferably phenyl or naphtyl, more preferably phenyl, wherein at least one, and preferably both, of the above listed $Z^1$ and $Z^2$ groups is, each independently, substituted with one or more substituents chosen from the group comprising or consisting of alkanoylamino, such as preferably acetylamino. If substituted phenol is released from this group of compounds in an organism, this would be biologically 'safe'.

A further special group of compounds are those compounds of formula (I) wherein at least one, and preferably both, of $Z^1$ and $Z^2$ is acetylaminophenyl, preferably p-acetylaminophenyl. If acetylaminophenol, e.g., p-acetylaminophenol, is released from this group of compounds in an organism, this would be biologically 'safe'.

A further special group of compounds are those compounds of formula (I) wherein the said remaining substituents of the substituents $R^1$, $R^2$, $R^3$, $R^4$ and $R^5$ are, each independently, chosen from the group comprising or consisting of: hydrogen, halogen, perhaloalkyl, alkyl, aralkyl, hydroxyl, alkoxy, aryloxy, aralkoxy, formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl, alkylcarbamoyl, arylcarbamoyl, aralkylcarbamoyl, and sulfonyl.

Another special group of compounds are those compounds of formula (I) wherein the said remaining substituents of the substituents $R^1$, $R^2$, $R^3$, $R^4$ and $R^5$ are, each independently, chosen from the group comprising or consisting of: hydrogen, halogen, perhaloalkyl, alkyl, alkoxy, alkanoyl, alkanoyloxy, alkoxycarbonyl.

Another special group of compounds are those compounds of formula (I) wherein the said remaining substituents of the substituents $R^1$, $R^2$, $R^3$, $R^4$ and $R^5$ are hydrogen.

Particularly preferred compounds according to the invention are compounds having the formula (I) as indicated above, or a pharmaceutically acceptable salt thereof, wherein $R^1$, $R^2$, $R^4$ and $R^5$ each are hydrogen, $R^3$ is guanidino or amidino, A is a direct bond, methylene or ethylene, $Z^1$ and $Z^2$ are, each independently, phenyl, p-acetylaminophenyl, hydroxyphenyl, methoxyphenyl, sulfonylaminophenyl, ureylphenyl, methoxycarbonylphenyl or alkylaminocarbonylphenyl, $R^6$ is hydrogen or methyl, and X is hydrogen, methoxycarbonyl, ethoxycarbonyl, methylcarbonyl, methylcarbamoyl, ethylcarbamoyl, benzylcarbamoyl, phenylmethoxycarbonyl, benzoyl, phenylsulfonyl, benzylsulfonyl, naphtylsulfonyl, (2,4,6-trimethyl)phenylsulfonyl, $-S(=O)_2CH_3$ or $-S(=O)_2H$.

Particularly preferred compounds according to the invention are compounds having the formula (I) as indicated above, or a pharmaceutically acceptable salt thereof, wherein $R^1$, $R^2$, $R^4$ and $R^5$ each are hydrogen, $R^3$ is guanidino, A is methylene, $Z^1$ and $Z^2$ are phenyl or $Z^1$ and $Z^2$ are p-acetylaminophenyl, $R^6$ is hydrogen, and X is hydrogen, methoxycarbonyl, ethoxycarbonyl, methylcarbonyl, methylcarbamoyl, ethylcarbamoyl, benzylcarbamoyl, phenylmethoxycarbonyl, benzylsulfonyl, or naphtylsulfonyl.

Exemplary particularly preferred compounds include compounds 7b {Diphenyl 1-(benzyloxycarbonylamino)-2-(4-guanidinophenyl)-ethanephosphonate}, 7c {Diphenyl 1-(benzoylamino)-2-(4-guanidinophenyl)-ethanephosphonate}, 7d {Diphenyl 1-(o toluenesulfonylamino)-2-(4-guanidinophenyl)-ethanephosphonate}, 7e {Diphenyl 1-(naphthalenesulfonylamino)-2-(4-guanidinophenyl)-ethanephosphonate}, 7f {Diphenyl 1-(2,3,6-triisopropylbenzenesulfonyl)amino-2-(4-guanidinophenyl)-ethanephosphonate}, 79 {Diphenyl 1-(methylsulfonylamino)-2-(4-guanidinophenyl)-ethanephosphonate}, 8a {Diphenyl 1-(N-benzyloxycarbonylamino)-1-(4-amidinophenyl)methanephosphonate}, 8b {Diphenyl 1-(N-benzyloxycarbonylamino)-2-(4-amidinophenyl)ethanephosphonate}, 8c {Diphenyl 1-(N-benzyloxycarbonylamino)-1-(4-amidinophenyl)propanephosphonate}, 9b {Di-(4-acetamidophenyl) 1-(benzyloxycarbonylamino)-2-[(4-guanidino)phenyl]ethanephosphonate} 9c {Di-(4-acetamidophenyl) 1-(methylsulfonylamino)-2-(4-guanidinophenyl)-ethanephosphonate}, 34d {Diphenyl 1-amino-2-(4-guanidinophenyl)ethylphosphonate}, 34e {Bis(4-acetamidophenyl) 1-amino-2-(4-guanidinophenyl)ethylphosphonate}, 35a {Methyl 1-(diphenoxyphosphoryl)-2-(4-guanidinophenyl)ethylcarbamate}, 35b {Methyl 1-(bis(4-acetamidophenoxy)phosphoryl)-2-(4-guanidino-phenyl)ethylcarbamate}, 35c {Ethyl 1-(diphenoxyphosphoryl)-2-(4-guanidinophenyl)ethylcarbamate}, 39a {Diphenyl 2-(4-guanidinophenyl)-1-(3-methylureido) ethylphosphonate}, 39b {Diphenyl 1-(3-benzylureido)-2-(4-guanidinophenyl)ethylphosphonate} and 41 {Diphenyl 1-acetamido-2-(4-guanidinophenyl)ethylphosphonate}. as described in the examples section.

Method of Preparation

In another aspect, the present invention relates to methods for preparing the compounds according to the invention. Exemplary methods are detailed in the examples section and a skilled person will be able to readily adapt the exemplary methods to prepare all compounds according to the invention.

Uses of the Compounds According to the Invention

An important feature attributed to the compounds according to the invention is their broad application possibility. The compounds according to the invention exhibit uPA inhibition activity.

Accordingly, in an aspect, the present invention provides a method for inhibiting the activity of urokinase plasminogen activator, comprising the step of adding to a composition comprising the urokinase plasminogen activator a compound according to the invention.

It is known that uPA plays role in various processes including the remodelling of tissue and cell migration, such as, by means of example, in angiogenesis and cell-migration, such as, e.g., in metastasis of cancer cells. It also known or contemplated that uPA plays role in the pathogenesis of various conditions, including but not limited to, wound healing, cancer, atherosclerosis, vascular restenosis, cardiac rupture, macular degeneration, diabetic retinopathy, hemorrhagic atherosclerosis and inflammatory conditions, such as rheumatoid arthritis and psoriasis. It is known that uPA inhibitors may be useful in modulating or treating such disorders (see, e.g., Rockway et al. Inhibitors of the proteolytic activity of urokinase type plasminogen activator. Curr Pharm Des. 2003; 9(19):1483-98).

Accordingly, the compounds of the present invention are useful in therapeutic treatment and modulation of the above processes and conditions.

Therefore, in an aspect, the invention relates to the compounds according to invention for use as a medicament. In another aspect, the invention provides use of the compounds according to the invention for the preparation of a medicament for treating a condition chosen from the group comprising or consisting of: cancer, tumour growth, tumour invasion, tumour metastasis, diabetic retinopathy, hemorrhagic atherosclerosis and inflammatory conditions, such as rheumatoid arthritis and psoriasis.

In another aspect, the invention provides use of the compounds according to the invention for the preparation of a medicament for treating conditions associated with cell migration. The term "conditions associated with cell migration" as used herein refers to, but is not limited to, any type of cancer or condition involving cell migration, including for example chronic inflammation and restenosis in cardiovascular disease. The compounds of the invention may be especially used in the treatment of cancers, in particular malignant cancers, such as but not limited to leukemia, non-small cell lung cancer, small cell lung cancer, CNS cancer, melanoma, ovarian cancer, renal cancer, prostate cancer, breast cancer, glioma, colon cancer, bladder cancer, sarcoma, pancreatic cancer, colorectal cancer, head and neck cancer, liver cancer and hematological cancer and lymphoma.

In addition, the compounds according to the invention may also be very suitable in the treatment of scar tissue and wounds. It is believed that most, if not all, of the compounds of the present invention can act as active ingredients in treating scar tissue and in promoting wound healing and tissue regeneration.

Further, the invention also provides for use of the compounds of the invention for inhibiting angiogenesis. Inhibition of angiogenesis is therapeutically useful to inhibit tumor growth.

Pharmaceutical Compositions Comprising the Compounds of the Invention

In another aspect, the present invention relates to a pharmaceutical composition comprising a pharmaceutically acceptable excipient and a therapeutic amount of a compound according to the invention.

The term "therapeutically effective amount" as used herein means that amount of active compound or component or pharmaceutical agent that elicits the biological or medicinal response in a tissue, system, animal or human that is being sought by a researcher, veterinarian, medical doctor or other clinician, which includes alleviation of the symptoms of the disease being treated.

The pharmaceutical composition can be prepared in a manner known per se to one of skill in the art. For this purpose, at least one compound having formula (I), one or more solid or liquid pharmaceutical excipients and, if desired, in combination with other pharmaceutical active compounds, are brought into a suitable administration form or dosage form which can then be used as a pharmaceutical in human medicine or veterinary medicine.

Particular forms of the pharmaceutical composition may be, for example, solutions, suspensions, emulsions, creams, tablets, capsules, nasal sprays, liposomes or micro-reservoirs, especially compositions in orally ingestible or sterile injectable form, for example, as sterile injectable aqueous or oleaginous suspensions or suppositories. The preferred form of composition contemplated is the dry solid form, which includes capsules, granules, tablets, pills, boluses and powders. The solid carrier may comprise one or more excipients, e.g. lactose, fillers, disintegrating agents, binders, e.g. cellulose, carboxymethylcellulose or starch or anti-stick agents, e.g. magnesium stearate, to prevent tablets from adhering to tabletting equipment. Tablets, pills and boluses may be formed so as to disintegrate rapidly or to provide slow release of the active ingredient.

In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkyloxycarbonylalkyl or carboxyalkyloxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-C D, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxy groups are etherified with different groups such as, for example, hydroxypropyl and hydroxyethyl. An interesting way of formulating the analogues in combination with a cyclodextrin or a derivative thereof has been described in EP-A-721,331. Although the formulations described therein are with antifungal active ingredients, they are equally interesting for formulating the analogues. Said formulations may also be rendered more palatable by adding pharmaceutically acceptable sweeteners and/or flavors.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered. The term "a solid dispersion" also comprises dispersions that are less homogenous throughout than solid solutions. Such dispersions are not chemically and physically uniform throughout or comprise more than one phase.

The water-soluble polymer is conveniently a polymer that has an apparent viscosity of 1 to 100 mPa·s when dissolved in a 2% aqueous solution at 20° C. solution. Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. Various techniques exist for preparing solid dispersions including melt-extrusion, spray-drying and solution-evaporation, melt-extrusion being preferred.

It may further be convenient to formulate the analogues in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Said beads comprise (a) a central, rounded or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

In an aspect, the invention provides for use of a pharmaceutical composition according to the invention in the treatment of a condition chosen from the group comprising or consisting of: cancer, tumour growth, tumour invasion, tumour metastasis, diabetic retinopathy, hemorrhagic atherosclerosis and inflammatory conditions, such as rheumatoid arthritis and psoriasis.

Methods of Treatment

As indicated above, due to their favourable properties the compounds according to the present invention are particularly useful in the treatment of individuals suffering from the conditions listed above. Therefore, in another aspect, the present invention also relates to a method of treating a condition chosen from the group comprising or consisting of: cancer, tumour growth, tumour invasion, tumour metastasis, diabetic retinopathy, hemorrhagic atherosclerosis and inflammatory conditions, such as rheumatoid arthritis and psoriasis, comprising administrating to an individual in need of such treatment a pharmaceutical composition according to the invention.

For these purposes, the pharmaceutical composition of the present invention may be administered orally, parenterally, i.e. including subcutaneous injections, intravenous, intramuscular, intrasternal injection or infusion techniques, by inhalation spray, or rectally, in dosage unit formulations containing conventional non-toxic pharmaceutically acceptable carriers, adjuvants and vehicles.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For example, the compounds of the invention are capable of very effectively inhibiting the growth or/and spreading of malignant tumors, for example tumor spreading of pancreatic carcinoma, tumor growth of breast carcinoma and also metastasizing of tumors. It is possible to use the uPA inhibitors, where appropriate, together with other anti-tumor agents or with other types of treatment, e.g. radiation or surgery. Furthermore, the inhibitors according to the invention are also effective in other uPA-associated disorders (e.g. in preventing formation of blisters in the case of the skin disorder pemphigus vulgaris).

Essentially, the primary modes of treatment of solid tumor cancers comprise surgery, radiation therapy and chemotherapy, separately and in combination. The compounds according to the invention are suitable for use in combination with these medicinal techniques. The compounds of the invention may be useful in increasing the sensitivity of tumor cells to radiation in radiotherapy and also in potentiating or enhancing damage to tumors by chemotherapeutic agents. The compounds and their pharmaceutically acceptable salts may also be useful for sensitising multidrug-resistant tumor cells. The compounds according to the invention are useful therapeutic compounds for administration in conjunction with other DNA-damaging cytotoxic drugs or radiation used in radiotherapy to potentiate their effect.

In another embodiment of the method of the invention, the administration may be performed with food, e.g., a high-fat meal. The term 'with food' means the consumption of a meal either during or no more than about one hour before or after administration of a pharmaceutical composition according to the invention.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

The oral administration of a pharmaceutical composition comprising a compound according to the invention, or a pharmaceutically acceptable salt or ester thereof, is suitably accomplished by uniformly and intimately blending together a suitable amount of the compound in the form of a powder, optionally also including a finely divided solid carrier, and encapsulating the blend in, for example, a hard gelatin capsule. The solid carrier can include one or more substances, which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Oral administration of a pharmaceutical composition comprising an compound according to the invention, or a pharmaceutically acceptable salt or ester thereof can also be accomplished by preparing capsules or tablets containing the desired amount of the compound, optionally blended with a solid carrier as described above. Compressed tablets containing the pharmaceutical composition of the invention can be prepared by uniformly and intimately mixing the active ingredient with a solid carrier such as described above to provide a mixture having the necessary compression properties, and then compacting the mixture in a suitable machine to the shape and size desired. Molded tablets maybe made by molding in a suitable machine, a mixture of powdered compound moistened with an inert liquid diluent.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the active analogue, if desired with the substances customary therefor such as solubilizers, emulsifiers or further auxiliaries, are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquidify and/or dissolve in the rectal cavity to release the drug.

The pharmaceutical compositions of this invention can be administered to humans in dosage ranges specific for each analogue comprised in said compositions. The compounds comprised in said composition can be administered together or separately.

It will be understood, however, that specific dose level and frequency of dosage for any particular patient may be varied and will depend upon a variety of factors including the activity of the specific analogue employed, the metabolic stability and length of action of that compound, the age, body weight, general health, sex, diet, mode and time of administration, rate of excretion, drug combination, the severity of the particular condition, and the host undergoing therapy.

The following examples are meant to illustrate the present invention. These examples are presented to exemplify the invention and are not to be considered as limiting the scope of the invention.

EXAMPLES

The practice of the present invention will employ, unless otherwise indicated, conventional techniques of synthetic organic chemistry, biological testing, and the like, which are within the skill of the art. Such techniques are explained fully in the literature.

Example 1

Non-Limiting Examples of Preferred Compounds According to the Invention Having General Formula (I) are Listed Hereunder in Table A

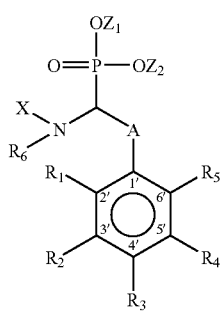

In the following table A, "H" denotes hydrogen; "GUA" denotes radical of the formula

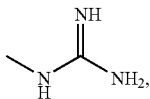

"metGUA" denotes radical of the formula

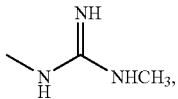

"et-GUA" denotes radical of the formula

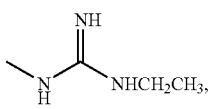

"AMI" denotes radical of the formula

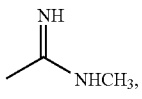

"metAMI" denotes radical of the formula

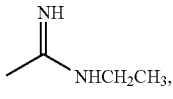

"etAMI" denotes radical of the formula

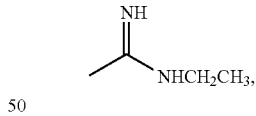

"PHE" denotes radical of the formula

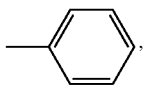

"PCM" denotes radical of the formula

"Boyl" denotes radical of the formula

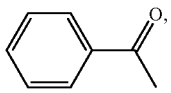

"Bsulf" denotes radical of the formula

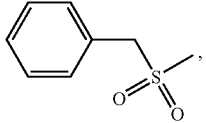

"Boxcarb" denotes radical of the formula

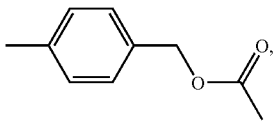

"Sulf" denotes radical of the formula

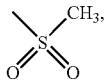

"methoxycarbonyl" denotes radical of the formula —C(=O)OCH$_3$, "ethoxycarbonyl" denotes radical of the formula —C(=O)OCH$_2$CH$_3$, "methylcarbonyl" denotes radical of the formula —C(=O)CH$_3$, "methylcarbamoyl" denotes radical of the formula —C(=O)NHCH$_3$, "ethylcarbamoyl" denotes radical of the formula —C(=O)NHCH$_2$CH$_3$, benzylcarbamoyl denotes radical of the formula

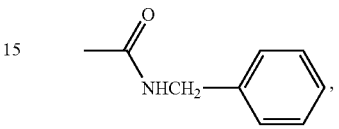

and "napthylsulfonyl" denotes radical of the formula

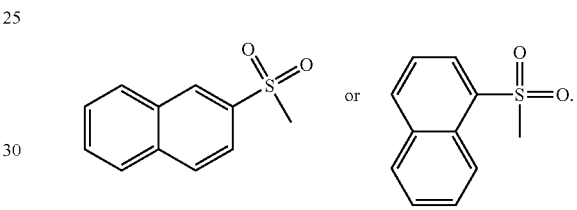

TABLE A

| $R^1$ | $R^2$ | $R^3$ | $R^4$ | $R^5$ | A | $R^6$ | X | $Z^1$ | $Z^2$ |
|---|---|---|---|---|---|---|---|---|---|
| H | H | GUA | H | H | —CH$_2$— | H | Boyl | PHE | PHE |
| H | H | metGUA | H | H | —CH$_2$— | H | Boyl | PHE | PHE |
| H | H | etGUA | H | H | —CH$_2$— | H | Boyl | PHE | PHE |
| H | H | AMI | H | H | —CH$_2$— | H | Boyl | PHE | PHE |
| H | H | metAMI | H | H | —CH$_2$— | H | Boyl | PHE | PHE |
| H | H | etAMI | H | H | —CH$_2$— | H | Boyl | PHE | PHE |
| H | H | GUA | H | H | —CH$_2$— | H | Boyl | PCM | PCM |
| H | H | metGUA | H | H | —CH$_2$— | H | Boyl | PCM | PCM |
| H | H | etGUA | H | H | —CH$_2$— | H | Boyl | PCM | PCM |
| H | H | AMI | H | H | —CH$_2$— | H | Boyl | PCM | PCM |
| H | H | metAMI | H | H | —CH$_2$— | H | Boyl | PCM | PCM |
| H | H | etAMI | H | H | —CH$_2$— | H | Boyl | PCM | PCM |
| H | H | GUA | H | H | —CH$_2$— | H | Bsulf | PHE | PHE |
| H | H | metGUA | H | H | —CH$_2$— | H | Bsulf | PHE | PHE |
| H | H | etGUA | H | H | —CH$_2$— | H | Bsulf | PHE | PHE |
| H | H | AMI | H | H | —CH$_2$— | H | Bsulf | PHE | PHE |
| H | H | metAMI | H | H | —CH$_2$— | H | Bsulf | PHE | PHE |
| H | H | etAMI | H | H | —CH$_2$— | H | Bsulf | PHE | PHE |
| H | H | GUA | H | H | —CH$_2$— | H | Bsulf | PCM | PCM |
| H | H | metGUA | H | H | —CH$_2$— | H | Bsulf | PCM | PCM |
| H | H | etGUA | H | H | —CH$_2$— | H | Bsulf | PCM | PCM |
| H | H | AMI | H | H | —CH$_2$— | H | Bsulf | PCM | PCM |
| H | H | metAMI | H | H | —CH$_2$— | H | Bsulf | PCM | PCM |
| H | H | etAMI | H | H | —CH$_2$— | H | Bsulf | PCM | PCM |
| H | H | GUA | H | H | —CH$_2$— | H | Boxcarb | PHE | PHE |
| H | H | metGUA | H | H | —CH$_2$— | H | Boxcarb | PHE | PHE |
| H | H | etGUA | H | H | —CH$_2$— | H | Boxcarb | PHE | PHE |
| H | H | AMI | H | H | —CH$_2$— | H | Boxcarb | PHE | PHE |
| H | H | metAMI | H | H | —CH$_2$— | H | Boxcarb | PHE | PHE |
| H | H | etAMI | H | H | —CH$_2$— | H | Boxcarb | PHE | PHE |
| H | H | GUA | H | H | —CH$_2$— | H | Boxcarb | PCM | PCM |
| H | H | metGUA | H | H | —CH$_2$— | H | Boxcarb | PCM | PCM |
| H | H | etGUA | H | H | —CH$_2$— | H | Boxcarb | PCM | PCM |
| H | H | AMI | H | H | —CH$_2$— | H | Boxcarb | PCM | PCM |
| H | H | metAMI | H | H | —CH$_2$— | H | Boxcarb | PCM | PCM |

TABLE A-continued

| R¹ | R² | R³ | R⁴ | R⁵ | A | R⁶ | X | Z¹ | Z² |
|---|---|---|---|---|---|---|---|---|---|
| H | H | etAMI | H | H | —CH₂— | H | Boxcarb | PCM | PCM |
| H | H | GUA | H | H | —CH₂— | H | Sulf | PHE | PHE |
| H | H | metGUA | H | H | —CH₂— | H | Sulf | PHE | PHE |
| H | H | etGUA | H | H | —CH₂— | H | Sulf | PHE | PHE |
| H | H | AMI | H | H | —CH₂— | H | Sulf | PHE | PHE |
| H | H | metAMI | H | H | —CH₂— | H | Sulf | PHE | PHE |
| H | H | etAMI | H | H | —CH₂— | H | Sulf | PHE | PHE |
| H | H | GUA | H | H | —CH₂— | H | Sulf | PCM | PCM |
| H | H | metGUA | H | H | —CH₂— | H | Sulf | PCM | PCM |
| H | H | etGUA | H | H | —CH₂— | H | Sulf | PCM | PCM |
| H | H | AMI | H | H | —CH₂— | H | Sulf | PCM | PCM |
| H | H | metAMI | H | H | —CH₂— | H | Sulf | PCM | PCM |
| H | H | etAMI | H | H | —CH₂— | H | Sulf | PCM | PCM |
| H | H | GUA | H | H | —CH₂— | H | H | PHE | PHE |
| H | H | GUA | H | H | —CH₂— | H | H | PCM | PCM |
| H | H | GUA | H | H | —CH₂— | H | methoxycarbonyl | PHE | PHE |
| H | H | GUA | H | H | —CH₂— | H | methoxycarbonyl | PCM | PCM |
| H | H | GUA | H | H | —CH₂— | H | ethoxycarbonyl | PHE | PHE |
| H | H | GUA | H | H | —CH₂— | H | ethoxycarbonyl | PCM | PCM |
| H | H | GUA | H | H | —CH₂— | H | methylcarbonyl | PHE | PHE |
| H | H | GUA | H | H | —CH₂— | H | methylcarbonyl | PCM | PCM |
| H | H | GUA | H | H | —CH₂— | H | methylcarbamoyl | PHE | PHE |
| H | H | GUA | H | H | —CH₂— | H | methylcarbamoyl | PCM | PCM |
| H | H | GUA | H | H | —CH₂— | H | ethylcarbamoyl | PHE | PHE |
| H | H | GUA | H | H | —CH₂— | H | ethylcarbamoyl | PCM | PCM |
| H | H | GUA | H | H | —CH₂— | H | benzylcarbamoyl | PHE | PHE |
| H | H | GUA | H | H | —CH₂— | H | benzylcarbamoyl | PCM | PCM |
| H | H | GUA | H | H | —CH₂— | H | napthylsulfonyl | PHE | PHE |
| H | H | GUA | H | H | —CH₂— | H | napthylsulfonyl | PCM | PCM |
| H | H | AMI | H | H | —CH₂— | H | H | PHE | PHE |
| H | H | AMI | H | H | —CH₂— | H | H | PCM | PCM |
| H | H | AMI | H | H | —CH₂— | H | methoxycarbonyl | PHE | PHE |
| H | H | AMI | H | H | —CH₂— | H | methoxycarbonyl | PCM | PCM |
| H | H | AMI | H | H | —CH₂— | H | ethoxycarbonyl | PHE | PHE |
| H | H | AMI | H | H | —CH₂— | H | ethoxycarbonyl | PCM | PCM |
| H | H | AMI | H | H | —CH₂— | H | methylcarbonyl | PHE | PHE |
| H | H | AMI | H | H | —CH₂— | H | methylcarbonyl | PCM | PCM |
| H | H | AMI | H | H | —CH₂— | H | methylcarbamoyl | PHE | PHE |
| H | H | AMI | H | H | —CH₂— | H | methylcarbamoyl | PCM | PCM |
| H | H | AMI | H | H | —CH₂— | H | ethylcarbamoyl | PHE | PHE |
| H | H | AMI | H | H | —CH₂— | H | ethylcarbamoyl | PCM | PCM |
| H | H | AMI | H | H | —CH₂— | H | benzylcarbamoyl | PHE | PHE |
| H | H | AMI | H | H | —CH₂— | H | benzylcarbamoyl | PCM | PCM |
| H | H | AMI | H | H | —CH₂— | H | napthylsulfonyl | PHE | PHE |
| H | H | AMI | H | H | —CH₂— | H | napthylsulfonyl | PCM | PCM |

Further non-limiting examples of preferred compounds according to the invention having general formula (I) are as those listed in Table A, wherein A is a direct bond. Yet further non-limiting examples of preferred compounds according to the invention having general formula (I) are as those listed in Table A, wherein A is —CH₂CH₂—.

Example 2

Further Non-Limiting Examples of Preferred Compounds According to the Invention Having General Formula (I) are Shown as Compounds 7b to 7g and 8a to 8c Below (the Designations R₁ and R₂ as Used in this Example 2 only apply to this Example 2)

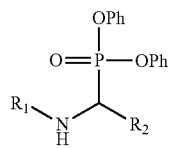

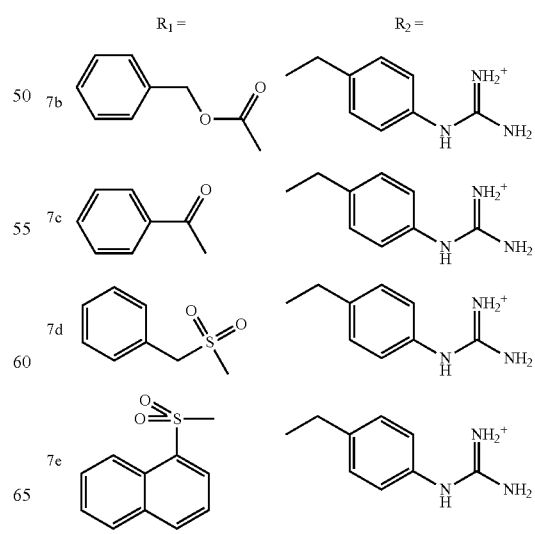

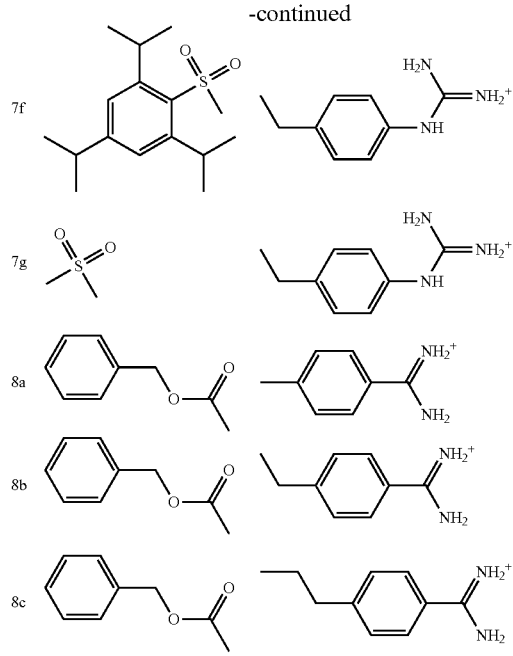

Example 3

Yet Further Non-Limiting Examples of Preferred Compounds According to the Invention Having General Formula (I) are Shown as Compounds 9b and 9c Below (the Designation Pcm as Used in this Example 3 Only Applies to this Example 3)

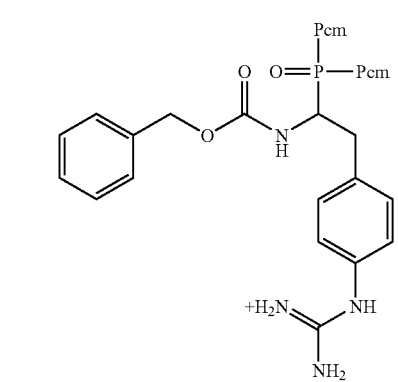

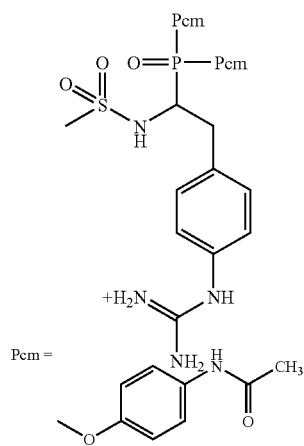

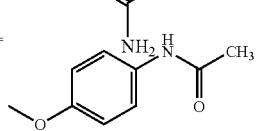

Example 4

Preparation of Compounds According to the Invention

Diphenylphosphonylated compounds according to the invention (as e.g. in example 2) were prepared according to Scheme 1, by a fast and convenient synthetic route, affording the opportunity to obtain large and diverse series of compounds. The aminophosphonate building block was prepared from tert-butylcarbamate protected 4-aminophenylacetaldehyde (12), prepared from the corresponding alcohol (11) with Dess-Martin periodinane (Dess, D. B. and Martin, J. C. Readily Accessible 12-I-5 Oxidant for the Conversion of Primary and Secondary Alcohols to Aldehydes and Ketones. J. Org. Chem., 1983, 48, 4155-4156). An amidoalkylation reaction with benzylcarbamate and triphenylphosphite using copper triflate as catalyst, afforded N-benzyloxycarbonyl protected diphenyl phosphonate 13 (Van der Veken, P.; El Sayed, I.; Joossens, J.; Stevens, C. V.; Augustyns, K. and Haemers, A.; Lewis Acid Catalyzed Synthesis of N-Protected Diphenyl 1-Aminoalkyl-Phosphonates. Synthesis, 2005, 4, 634-638). Acidolysis removed the tert-butyl carbamate protecting group. N,N'-bis(tert-butoxycarbonyl)-1-guanylpyrazole was used to introduce the protected guanidine group (Drake, B.; Patek, M.; Lebl, M., A Convenient Preparation of Monosubstituted N,N'-Di(Boc)-Protected Guanidines. Synthesis, 1994, 579-582). Compound 14 was subsequently deprotected under hydrogenolytic conditions. Small non-peptide guanidyl compounds (7) were made by coupling compound (15) with selected sulfonyl chlorides or acylchlorides in pyridine. The p-acetylaminophenyl phosphonates (as e.g. in example 3) were prepared following scheme 1 using tri-p-acetylaminophenylphosphite (Belyaev et al. A. Structure-Activity Relationship of Diaryl Phosphonate Esters as Potent Irreversible Dipeptidyl Peptidase IV Inhibitors. J. Med. Chem., 1999, 42, 1041-1052) (22).

Scheme 1:

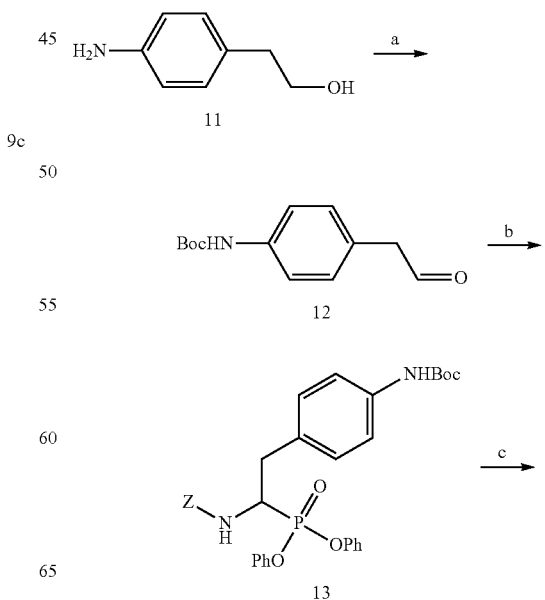

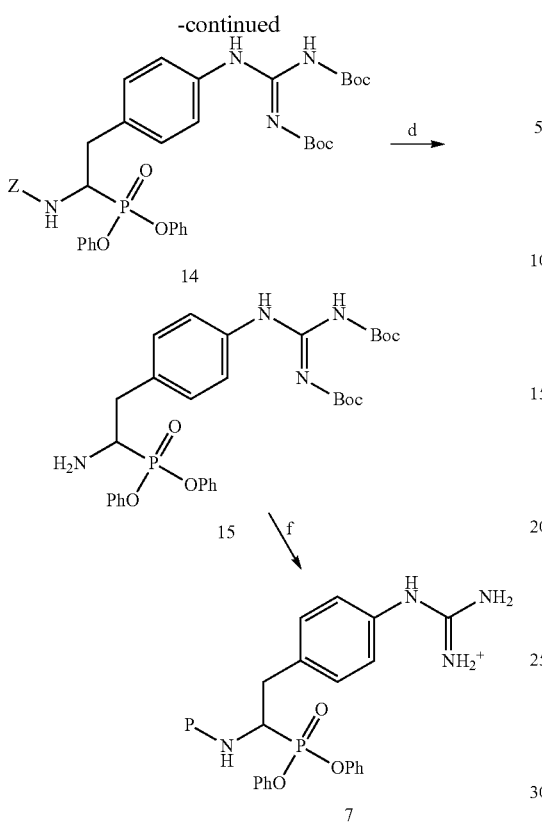

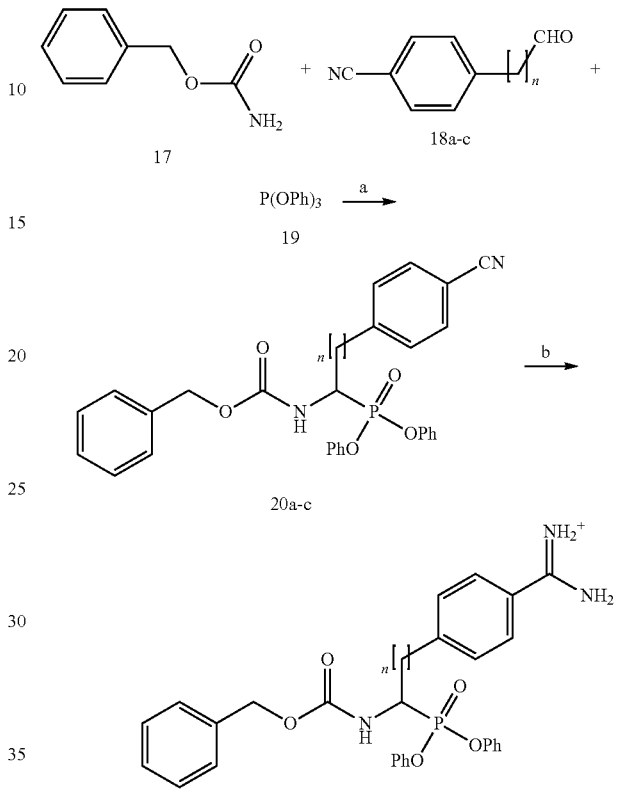

(a) (i) Di-tert-butyl dicarbonate, TEA, dioxane(ii) Dess-Martin oxidation;
(b) Benzyl carbamate, triphenyl phosphite, Cu(OTf)2, DCM; (c) (i) TFA; (ii) N,N'-bis(tert-butoxycarbonyl)-1-guanylpyrazole, MeCN; (d) H2, Pd/C; (f) (i) P—Cl, pyridine (ii) TFA P stands for diferent acyl, sulfonyl and carbamate groups

Example 5

Preparation of Further Compounds According to the Invention

Amidine compounds 8 were synthesised as described by Powers et al. (scheme 2), but we used the procedure with Cu(OTf)$_2$ to prepare the diphenyl phosphonate (20) (Jackson, S. D.; Fraser, S. A.; Ni, L.-M.; Kam, C.-M.; Winkler, U.; Johnson, D. A.; Froelich, C. J.; Hudig, D.; and Powers, J. C. Synthesis and Evaluation of Diphenyl Phosphonate Esters as Inhibitors of the Trypsin-like Granzymes A and K and Mast Cell Tryptase. J. Med. Chem., 1998, 41, 2289-2301). Z-(4-AmPhGly)$^P$(OPh)$_2$ was prepared by a Lewis acid catalyzed amidoalkylation reaction, starting with cyanobenzaldehyde (18a) to give Z-(4-CN-PhGly)$^P$(OPh)$_2$ (20a) which was converted to the amidine (8a) using a Pinner type reaction. The 4-amidinophenylalanine phosphonate diphenyl ester derivative Z-(4-AmPhe)$^P$(OPh)$_2$ was synthesised in the same way from 4-cyanophenylacetaldehyde. 4-Cyanophenylacetaldehyde (18b) was made from 4-cyanobenzaldehyde using a Darzen condensation (scheme 3). 4-(3-Oxo-propyl)-benzonitrile (18c) was synthesised from cyanobenzaldehyde: a Wittig olefination between 4-cyanobenzaldehyde and triphenylphosphoranylidene acetic acid ethyl ester followed by a reduction with NaBH$_4$ afforded 3-(4-cyanophenylpropanol) (21) (Baraldi, G. P.; Cacciari, B.; Romagnoli, R.; Spalluto, G.; Monopoli, A.; Ongini, E.; Varani, K. and Borea, P. A. 7-Substituted 5-Amino-2-(2-furyl)pyrazolo[4,3-e]-1,2,4-triazolo[1,5-c]pyrimidines as A2A Adenosine Receptor Antagonists: A study on the Importance of Modifications at The Side Chain on the Activity and Solubility. J. Med. Chem., 2002, 45, 115-126). This alcohol is oxidised with the Dess Martin reagent to aldehyde 18c.

Scheme 2:

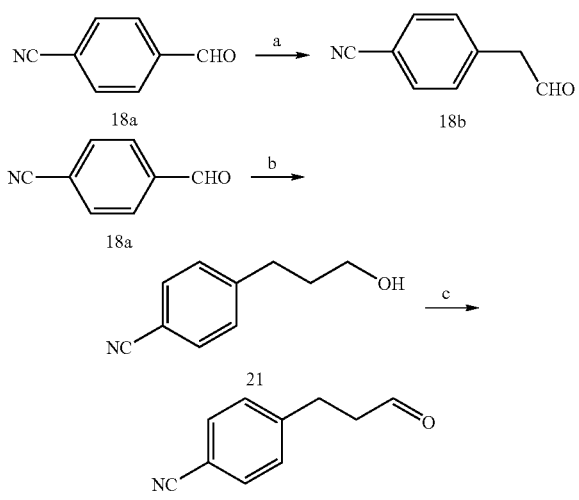

Scheme 3:

(a) (i) ClCH2O2Et, NaOEt (ii) NaOEt (iii) 2N HCl/toluene reflux, (b) (i) (Ph)3P=CHCO2Et (ii) NaBH4 (c) Dess Martin Oxidation

Example 6

Preparation of Compounds According to the Invention

The compounds 7b to 7g, 8a to 8c (as in example 2) and 9b and 9c (as in example 3) were prepared according to the above detailed schemes, using the procedures as described herein.

Reagents were obtained from Sigma-Aldrich or Acros. Characterisation of all compounds was done with 1H-NMR and mass spectrometry. $^1$H-NMR spectra were recorded on a 400 MHz Bruker Avance DRX-400 spectrometer. ES Mass spectra were obtained from an Esquire 3000plus iontrap mass spectrometer from Bruker Daltonics. Purity was verified using two diverse HPLC systems using respectively a mass and UV-detector. Water (A) and ACN (B), were used as eluents. LC-MS spectra were recorded on an Agilent 1100 Series HPLC system using a Alltech Prevail C18 column (2.1×50 mm, 3 μm) coupled with an Esquire 3000plus as MS detector and a 5-100% B, 20 min-gradient was used with a flow rate from 0.2 ml/min. 0.1% formic acid was added to solvent A and B. Reversed phase HPLC was run on a Gilson instrument equipped with an Ultrasphere ODS column (4.6×250 mm, 5 μm). A 10-100% B, 35 min gradient was used with a flow rate from 1 ml/min. 0.1% TFA was added to solvent A and B. 214 nm was used as wavelength. When necessary, the products were purified with flash chromatography on a Flashmaster II (Jones Chromatography) with a 30 min gradient of 0-50% EtOAc in hexane or 0-25% MeOH in EtOAc.

Boc-protection: To a solution of aminoalcohol or amino acid in 40 ml dioxane and 1 eq. triethylamine and 1 eq. di-tert-butyl dicarbonate (1.1 eq) were added and the mixture was stirred at room temperature for 1 h-8 h (reaction was followed by TLC). The solution was concentrated in vacuo and acidified with 2N HCl. The acidified aqueous layer was extracted 3 times with EtOAc. The organic solvent was evaporated and the obtained product was purified with flash chromatography.

Dess-Martin Oxidation: To a stirred suspension of alcohol (1 eq.) in DCM (80 ml) at −78° C., a solution of Dess-Martin periodane (1.5 eq from a 15 wt % solution) was added. The suspension was stirred for 3 h at room temperature. The resulting solution was poured into a vigorously stirred saturated NaHCO3 and Na2S203 solution (1:1 100 ml). The organic layer was separated and washed with brine and dried over $Na_2SO_4$. The crude product was obtained by removing the solvent in vacuo.

Amidoalkylation reaction: To a solution of crude aldehyde (1 eq.), triphenyl phosphite (1 eq.), and benzyl carbamate (1 eq.) in 50 ml DCM, 0.1 eq. Cu(OTf)$_2$ was added. The solution was stirred at room temperature for 4 h. DCM was removed in vacuo. The crude product was dissolved in MeOH and the solution kept at 4° C. until precipitation of diphenyl phosphonates was complete. Acetamidophenylphosphonates did not precipitate from MeOH and flash chromatography was necessary (EtOAC:MeOH) to isolate these compounds, for these compounds ACN is used as solvent for the amidoalkylation reaction.

Removal of Boc- and tert-butyl protecting groups: The protected peptide was dissolved in 50% TFA in DCM (2-5 ml). After stirring for 3 h at room temperature, the solvent was evaporated. The crude oil was washed with cold ether and a precipitate was formed.

Coupling with N,N'-bis(tert-butyloxycarbonyl)-1-guanidinopyrazole: A mixture of the phosphonate (1 eq.), N,N'-bis(tert-butyloxycarbonyl)-guanidinopyrazole (1 eq.) and TEA (3 eq.) in ACN (5 ml) was stirred at room temperature over night. For coupling with aromatic amines the mixture was stirred during 3 days. The solvent was evaporated and the residue dissolved in EtOAc. The organic layer was washed with 1 N HCl, saturated NaHCO$_3$ solution and brine. The organic layer was dried with $Na_2SO_4$. The solvent was evaporated to obtain the protected guanidine.

Removal of the Z-protecting group with hydrogenolysis: The Z protected peptide was dissolved in 20 ml MeOH. 10% Pd/C was added. After removing the oxygen with N$_2$, H$_2$ was bubbled through the solution. The solution was stirred for 8 h at room temperature. The solution was filtered over celite and the filtrate was evaporated.

The intermediates and products have the following characteristics.

4-(tert-Butyloxycarbonylamino)phenylacetaldehyde (intermediate No. 12 in scheme 1)

Yield: 58%
$^1$H NMR (CDCl$_3$, 400 MHz) δ 1.5 (s, 9H), 3.75 (d, 2H), 7.10 (d, 2H), 7.30 (m, 2H), 9.6 (t, 1H)
MS (ESI): m/z (M$^{+Na}$)258, (M$^{+MeOH+Na}$) 290

Diphenyl 1-Benzyloxycarbonylamino-2-(4-tert-butyloxycarbonylaminophenyl)-ethanephosphonate (intermediate No. 13 in scheme 1)

Crystallization from MeOH yielded 13 as a white solid: 30%
$^1$H NMR (CDCl$_3$) δ 1.5 (s, 9H), 3.0-3.5 (m, 2H), 4.7 (m, 1H), 5.1 (m, 2H), 5.2 (d, 1H), 6.5 (s, 1H) 7.1-7.4 (m, 19H)
MS (ESI) m/z (M$^{+Na}$) 625

Diphenyl 1-Benzyloxycarbonylamino-2-{4-[N,N'-bis(tert-butyloxycarbonyl)guanidino]phenyl}ethanephosphonate (intermediate No. 14 in scheme)

Yield 65%
$^1$H NMR (CDCl$_3$) δ 1.5 (d, 18H), 3.0-3.4 (m, 2H), 4.7 (m, 1H), 5.1 (m, 2H), 7.1-7.4 (m, 19H) MS (ESI) m/z (M$^{+Na}$) 745

Diphenyl 1-(benzyloxycarbonylamino)-2-(4-guanidinophenyl)-ethanephosphonate (7b)

Yield: 91%
$^1$H NMR (CD$_3$OD, 400 MHz): δ 3.0 (m, 1H), 3.4 (m, 1H), 4.7 (m, 1H), 5.1 (m, 2H), 5.8 (s, 1H), 7.0-7.4 (m, 19H)
HPLC: 214 nm: t$_r$ 21.1 min 98.5%
HPLC: 254 nm: t$_r$ 21.0 min 100.0%
LC/MS: t$_r$ 13.9 min. 100.0%
MS (ESI): m/z M$^{+1}$=545

Diphenyl 1-(benzoylamino)-2-{4-[N,N'-bis(tertbutyloxycarbonyl)guanidine]phenyl}ethanephosphonate (7c)(i)

Yield: 10%
$^1$H NMR (CDCl$_3$, 400 MHz): δ, 1.5 (18H, d), 3.2 (m, 1H), 3.4 (m, 1H), 3.4 (m, 1H), 5.4, (m, 1H), 7.1-7.5 (m, 19H), 7.6 (d, 2H), 10.3 (s, 1H), 11.5 (s, 1H)
MS (ESI): m/z M$^{+1}$=715

Diphenyl 1-(benzoylamino)-2-(4-guanidinophenyl)-ethanephosphonate (7c)

Yield: 80%
$^1$H NMR (CD$_3$OD, 400 MHz): δ 3.2 (m, 1H), 3.4 (m, 1H), 4.7 (m, 1H), 6.6 (m, 2H), 7.1 (m, 5H), 7.3-7.5 (m, 8H), 7.6 (m, 3H), 8.0 (d, 1H)
HPLC: 214 nm: t$_r$ 20.0 min 100.0%
HPLC: 254 nm: t$_r$ 21.0 min 100.0%
LC/MS: t$_r$ 13.3 min 91.2%
MS (ESI): m/z M$^{+1}$=515

Diphenyl 1-(α-toluenesulfonylamino)-2-{4-[N,N'-bis(tert-butyloxycarbonyl)guanidine]phenyl}ethanephosphonate (7d)(i)

Yield: 32%
$^1$H NMR (CDCl$_3$, 400 MHz): δ, 1.5 (18H, d), 3.1 (m, 2H), 3.4 (m, 1H), 3.8 (d, 1H), 4.0 (d, 1H), 4.6 (m, 1H), 5.1 (d, 1H), 7.1-7.3 (m, 17H), 7.6 (d, 2H), 10.3 (s, 1H), 11.5 (s, 1H)

Diphenyl 1-(o-toluenesulfonylamino)-2-(4-guanidinophenyl)-ethanephosphonate.TFA (7d)

Yield: 94%
$^1$H NMR (CD$_3$OD, 400 MHz): δ 3.1 (m, 1H), 3.5 (m, 1H), 4.1 (d, 1H), 4.2 (d, 1H), 4.6 (m, 1H), 7.2-7.5 (m, 19H)
HPLC: 214 nm: t$_r$ 20.2 min 94.1%
HPLC: 254 nm: t$_r$ 20.2 min 100.0%
LC/MS: t$_r$ 14.0 min. 100.0%
MS (ESI): m/z M$^{+1}$=565

Diphenyl 1-(N-naphthalenesulfonylamino)-2-{4-[N,N'-bis(tert-butyloxycarbonyl)guanidine]phenyl}ethanephosphonate (7e)(i)

Yield: 23%
$^1$H NMR (CDCl$_3$, 400 MHz): δ, 1.6 (18H, d), 3.0-3.2 (m, 2H), 4.5 (m, 1H), 6.0 (d, 1H), 6.6 (d, 2H), 6.9-7.6 (15H), 7.8 (d, 1H), 7.9 (d, 1H), 8.1 (d, 1H), 8.5 (d, 1H), 10.0 (s, 1H), 11.6 (s, 1H)

Diphenyl 1-(naphthalenesulfonylamino)-2-(4-guanidinophenyl)-ethanephosphonate.TFA (7e)

Yield: 93%
$^1$H NMR (CDCl$_3$, 400 MHz): δ 3.0 (m, 1H), 3.4 (m, 1H), 4.4 (m, 1H), 6.7 (d, 2H), 6.9 (d, 4H), 7.1-7.4 (11H), 7.6 (t, 1H), 7.7 (t, 1H) 7.9 (m, 1H), 8.1 (d, 1H)
HPLC: 214 nm: t$_r$ 20.6 min 96.3%
HPLC: 254 nm: t$_r$ 21.0 min 100.0%
LC/MS: t$_r$ 14.7 min. 100.0%
MS (ESI): m/z M$^{+1}$=601

Diphenyl 1-(N-2,3,6-tri-isopropylbenzenesulfonylamino)-2-{4-[N,N'-bis(tert-butyloxycarbonyl)guanidine]phenyl}ethanephosphonate (7f)(i)

Yield: 14%
$^1$H NMR (CDCl$_3$, 400 MHz): δ, 1.2-1.4 (m, 18H), 1.5 (d, 18H), 2.9-3.0 (m, 1H), 3.3-3.5 (m, 2H), 4.1 (m, 1H), 4.2 (m, 1H), 4.4 (m, 1H), 5.0 (d, 1H), 6.7 (d, 2H), 6.9 (d, 2H), 7.1-7.3 (m, 8H), 7.4 (d, 2H), 7.5 (d, 2H)

Diphenyl 1-(2,3,6-tri-isopropylbenzenesulfonyl)amino-2-(4-guanidinophenyl)-ethanephosphonate.TFA (7f)

Yield: 89%
$^1$H NMR (CD$_3$OD, 400 MHz): δ, 1.2-1.4 (m, 18H), 2.3 (m, 1H); 3.0-3.1 (m, 2H), 4.1-4.3 (3H), 7.0-7.6 (m, 16H)
HPLC: 214 nm: t$_r$ 26.9 min 100.0%
HPLC: 254 nm: t$_r$ 26.9 min 100.0%
LC/MS: t$_r$ 18.0 min. 99.0%
MS (ESI): m/z M$^{+1}$=677

Diphenyl 1-(methylsulfonylamino)-2-{4-[N,N'-bis(tert-butyloxycarbonyl)guanidine]phenyl}ethanephosphonate (7g) (i)

Yield: 18%
$^1$H NMR (CDCl$_3$, 400 MHz): δ, 1.5 (d, 18H), 2.5 (s, 3H), 3.0 (m, 1H), 3.5 (m, 1H), 4.5 (m, 1H), 5.6 (d, 1H), 7.1-7.6 (m, 14), 10.3 (s, 1H), 11.6 (s, 1H)

Diphenyl 1-(methylsulfonylamino)-2-(4-guanidinophenyl)-ethanephosphonate.TFA (7g)

Yield: 92%
$^1$H NMR (CD$_3$OD, 400 MHz): δ 3.1 (m, 1H), 3.5 (m, 1H), 4.5 (m, 1H), 7.2 (m, 8H), 7.4 (m, 4H), 7.45 (d, 2H)
HPLC: 214 nm: t$_r$ 18.2 min 98.0%
HPLC: 254 nm: t$_r$ 17.3 min 100.0%
LC/MS: t, min. 12.8 min 96.3%
MS (ESI): m/z M$^{+1}$=489 p-Cyanophenylacetaldehyde (18b)

Yield: 30%
$^1$H NMR (CDCl$_3$, 400 MHz): δ, (3.8, 2H), 7.3 (d, 2H), 7.6 (d, 2H), 9.8 (s, 1H)

Diphenyl 1-(N-benzyloxycarbonylamino)-1-(4 cyanophenyl)methanephosphonate (20a)

Yield: 70%

Diphenyl 1-(N-benzyloxycarbonylamino)-2-(4-cyanophenyl)ethanephosphonate (20b)

Yield 47%
$^1$H NMR (CDCl$_3$, 400 MHz): δ, 3.4-3.0 (m, 2H), 4.9 (m, 1H),), 5.1 (q, 2H), 6.9-7.5 (m, 19H)

Diphenyl 1-(N-benzyloxycarbonylamino)-1-(4-cyanophenyl)propanephosphonate (20c)

3-(4-cyanophenyl)propanol was oxidised with the dessmartin reagent to the aldehyde. The crude product was immediately dissolved in DCM without any further purification. The modified birum Oleksyszin reaction was used to prepare the diphenyl phosphonate. The obtained product was purified with flashchromatography.

21% yield starting from 3-(4-cyanophenyl)propanol
$^1$H NMR (CDCl$_3$, 400 MHz); δ, 2.1 (m, 1H), 2.35 (m, 1H), 2.8 (m, 1H), 2.9 (m, 1H), 4.5 (m, 1H), 5.1 (m, 2H), 5.7 (d, 1H), 7.1-7.4 (m, 16H), 7.5 (m, 3H)
MS (ESI): m/z M$^{+1}$=527

3-(p-Cyanophenyl)propanol (21)

4-cyanobenzaldehyde (5 g, 0.038 mol) and triphenylphosphoranylidene acetic acid ethyl ester (16 g, 0.045 mol) were dissolved in dry toluene (70 ml) and the solution was stirred at room temperature for 12 h. Then the solvent was removed under vacuum, and the residue was taken up with ether. The solid formed was removed by filtration and the organic phase was evaporated to give 3-(4-cyano-phenyl)-3-propenoic acid ethyl ester as a yellow oil. The compound was purified with flash chromatography (Hex/EtOAc). After evaporation of the desired fractions a white semi solid was obtained (6 g). The product was dissolved in ethanol and added dropwise to a suspension of sodium borohydride (11 g, 0.28 mol) in ethanol (100 ml) cooled at 0° C. The mixture was allowed to reach room temperature, and stirring was maintained for 18 h. 5 ml of acetone in 20 ml water was added dropwise to the mixture to destroy the remaining $NaBH_4$. The solvent was evaporated and water was added. This solution was three times extracted with EtOAc. The combined organic solutions were washed twice with 2N HCl and once with brine. The organic phase was dried and subsequent evaporation of the solvent a light yellow oil. 3 g, 47% yield.

MS (ESI): m/z $M^{+1}$=160

$^1$H NMR ($CDCl_3$, 400 MHz): δ, 1.90 (m, 2H), 2.75 (t, 2H), 3.65 (t, 2H), 7.28-7.32 (m, 2H), 7.53-7.59 (m, 2H).

Diphenyl 1-(N-benzyloxycarbonylamino)-1-(4-amidinophenyl)methanephosphonate (8a)

Yield: 14%
$^1$H NMR ($CD_3OD$, 400 MHz); δ2.0 (3H, s), 5.1 (q, 2H), 7.0 (m, 4H), 7.2-7.4 (m, 11H), 7.8 (s, 4H)
HPLC: 214 nm: $t_r$ 20.6 min. 100.0%
HPLC: 254 nm: $t_r$ 20.5 min. 100.0%
LC/MS: $t_r$ 13.9 min. 98.4%
MS (ESI): m/z $M^{+1}$=516

Diphenyl 1-(N-benzyloxycarbonylamino)-2-(4-amidinophenyl)ethanephosphonate (8b)

Yield: 48%
$^1$H NMR ($CD_3OD$, 400 MHz); δ2.0 (4H, s), 3.1 (m, 1H), 3.5 (m, 1H), 4.7 (m, 1H), 5.0 (q, 2H), 7.1-7.4 (m, 15H), 7.5 (d, 2H), 7.7 (d, 2H)
HPLC: 214 nm: $t_r$ 20.2 min. 90.3%
HPLC: 254 nm: $t_r$ 20.2 min. 91.3%
LC/MS: $t_r$ 13.6 min. 92.2%
MS (ESI): m/z $M^{+1}$=530

Diphenyl 1-(N-benzyloxycarbonylamino)-1-(4-amidinophenyl)propanephosphonate (8c)

Diphenyl 1-(N-(benzyloxycarbonyl)amino-1-(4 cyanophenyl)propanephosphonate was dissolved in dry chloroform:methanol (1:1). The mixture was cooled to 0° C. and saturated with dry HCl gas. The mixture was stirred for 3 days at 0° C. The solvent was evaporated and the cruded product was precipitated from dry ether. The product was dissolved in 4 eq of a 2M solution of amoniak in ethanol. The solution was stirred for 2 days at room temperature. Thes solvent was evaporated. The product was washed with EtOAc saturated with HCl. The product was precipitated from ether $^1$H NMR ($CD_3OD$, 400 MHz); δ 2.2 (m, 1H), 2.35 (m, 1H), 2.8 (m, 1H), 3.05 (m, 1H), 4.3 (m, 1H), 5.1 (q, 2H), 7.1-7.4 (m, 17H), 7.7 (d, 2H)
HPLC: 214 nm: $t_r$ 20.6 min. 92.0%
HPLC: 254 nm: $t_r$ 20.6 min. 93.0%
LC/MS: $t_r$ 14.7 min. 97.0%
MS (ESI): m/z $M^{+1}$=544

Tri-4-acetamidophenyl phosphite (22)

3 eq. of 4-acetamidophenol were dissolved in dry THF. Dry triethylamine (3 eq.) was added. This solution was cooled in an ice-bath and 1 eq. of $PCl_3$ was added dropwise. The mixture was brought to room temperature and stirred overnight. The solvent was filtered was evaporated. The crude product was purified with flash chromatography (MeOH in EtOAC, 0->20% in 40 min).

Yield 60%
$^1$H NMR ($CD_3OD$, 400 MHz): δ, 2.1 (s, 6H), 7.0 (m, 6H), 7.5 (m, 6H)
MS (ESI): m/z $M^{+Na}$=504

Di-(4-acetamidophenyl) 1-(benzyloxycarbonylamino)-2-(4-tert-butyloxycarbonylaminophenyl)ethanephosphonate (23)

Yield: 20%
$^1$H NMR ($CD_3OD$, 400 MHz): δ, 1.5 (s, 9H), 2.0, (s, 6H), 4.6, (m, 1H), 5.1 (m, 2H), 7.1-7.3 (m, 13H), 7.5 (m, 4H)
MS (ESI): m/z $M^{+Na}$=739

Di-(4-acetamidophenyl) 1-(benzyloxycarbonylamino)-2-[(4-guanidino)phenyl]ethanephosphonate.TFA (9b)

Yield: 95%
$^1$H NMR ($CD_3OD$, 400 MHz): δ 2.0, (s, 6H), 3.0 (m, 1H), 3.4 (m, 1H), 4.6, (m, 1H), 5.1 (m, 2H), 6.7-7.3 (m, 17H), 8.0 (d, 1H)
HPLC: 214 nm: $t_r$ 15.73 min 95.0%
HPLC: 254 nm: $t_r$ 15.72 min 94.2%
LC/MS: $t_r$ 12.1 min. 95.3%
MS (ESI): m/z $M^{+1}$=659

Di-(4-acetamidophenyl) 1-(methylsulfonylamino)-2-{4-[N,N'-bis(tert-butyloxycarbonyl)guanidino]phenyl}ethanephosphonate (9c)(i)

Yield: 18%
$^1$H NMR ($CDCl_3$, 400 MHz): δ, 1.5 (d, 18H), 2.0 (s, 3H), 2.1 (s, 3H), 2.2 (s, 3H), 2.9 (m, 1H), 3.3 (m, 1H), 4.3 (m, 1H), 7.1-7.6 (m, 12), 8.3 (s, 1H), 8.6 (s, 1H), 10.3 (s, 1H), 11.6 (s, 1H)
MS (ESI): m/z $M^{+1}$=803

Di-(4-acetamidophenyl) 1-(methylsulfonylamino)-2-(4-guanidinophenyl)-ethanephosphonate.TFA (9c)

Yield: 91%
$^1$H NMR ($CD_3OD$, 400 MHz): δ 2.1 (s, 6H), 2.7 (s, 3H), 3.1 (m, 1H), 3.5 (m, 1H), 4.5 (m, 1H), 7.1 (m, 4H), 7.2 (d, 2H), 7.45 (d, 2H), 7.6 (d, 4H)
HPLC: 214 nm: $t_r$ 12.2 min 93.2%
HPLC: 254 nm: $t_r$ 11.6 min 94.1%
LC/MS: t, min. 10.7 min 100.0%
MS (ESI): m/z $M^{+1}$=603

Example 7

Biochemical Evaluation

The small non-peptidic phosphonates according to the invention were evaluated for their ability to inhibit various trypsin-like serine proteases using the appropriate chromogenic substrates. The $IC_{50}$ values were calculated for uPA and five other trypsin-like serine proteases (Tables B and C). It was proven that these compounds were irreversible inhibitors for uPA. After diluting the inhibited enzyme with substrate solutions, no rise in activity of uPA was observed.

TABLE B

| | IC$_{50}$ (nM) | k$_{app}$ (M$^{-1}$·s$^{-1}$) | IC$_{50}$ (μM) or % inhibition at given concentration (μM) | | | | |
|---|---|---|---|---|---|---|---|
| | uPA | uPA | tPA | Plasmin | Thrombin | FXa | Trypsin |
| 7a | 840 ± 200 | 10 × 10$^1$ ± 6 × 10$^{1\dagger}$ | 44 ± 20 (50) | 30 ± 2 (35) | 0.78 ± 0.04 | 70% @ 250 | 0.22 ± 0.02 |
| 7b | 7 ± 2 | 42 × 10$^3$ ± 3 × 10$^3$ | 12.0 ± 0.8 (1700) | 3.0 ± 0.6 (300) | 2.4 ± 0.4 (300) | 100 ± 20 (11000) | 0.25 ± 0.04 (30) |
| 7c | 114 ± 11 | 24 × 10$^2$ ± 12 × 10$^{2\dagger}$ | 125 (1000) | 14 ± 1 (120) | 65% @ 125 | >250 | 0.57 ± 0.07 (5) |
| 7d | 7.7 ± 0.7 | 19 × 10$^3$ ± 1 × 10$^3$ | 7.3 ± 0.5 (1000) | 17 ± 2 (2000) | 11.9 ± 1.7 (1500) | 59% @ 62 | 0.17 ± 0.01 (20) |
| 7e | 26.5 ± 1.4 | 73 × 10$^2$ ± 4 × 10$^2$ | 44 ± 10 (1600) | 1.2 ± 0.1 (40) | 8.1 ± 0.8 (300) | 27 ± 2 (1000) | 0.28 ± 0.05 (10) |
| 7f | 260 ± 30 | 16 × 10$^2$ ± 1 × 10$^2$ | 16 ± 1 (60) | ~125 (500) | 60% @ 250 | 20 ± 2 (80) | 5.6 ± 0.04 (20) |
| 7g | 6.6 ± 0.8 | 14 × 10$^4$ ± 1 × 10$^4$ | 8 ± 2 (1000) | 11 ± 1 (1600) | ~125 (19000) | ~250 (40000) | 0.24 ± 0.04 (35) |
| 8a | 60000 ± 10000 | 43 × 10$^0$ ± 6 × 10$^0$ | 66 ± 7 (1) | 3.6 ± 0.4 | 0.288 ± 0.006 | 6.0 ± 0.2 | 0.42 ± 0.06 |
| 8b | 67 ± 25 | 20 × 10$^2$ ± 1 × 10$^{2\dagger}$ | 4 ± 2 (60) | 1.2 ± 0.1 (20) | 20 ± 2 (300) | 65% @ 250 | 0.97 ± 0.15 (10) |
| 8c | 900 ± 80 | 14 × 10$^1$ ± 1 × 10$^1$ | 68 ± 9 (70) | 6.2 ± 0.4 (7) | 17 ± 2 (20) | 13.7 ± 1.3 (15) | 3.5 ± 0.2 (4) |

TABLE C

| | IC$_{50}$ (nM) | k$_{app}$ (M$^{-1}$·s$^{-1}$) | IC$_{50}$ (μM) or % inhibition at given concentration (μM) | | | | |
|---|---|---|---|---|---|---|---|
| | uPA | uPA | tPA | Plasmin | Thrombin | FXa | Trypsin |
| 9b | 4.2 ± 0.9 | 80 × 10$^3$ ± 5 × 10$^{3\dagger}$ | 7 ± 1 (1700) | 0.9 ± 0.2 (200) | 0.39 ± 0.03 (90) | 100 ± 24 (23000) | 0.17 ± 0.02 (40) |
| 9c | 3.5 ± 0.5 | 21 × 10$^4$ ± 1 × 10$^4$ | 3.7 ± 0.4 (1000) | 2.0 ± 0.4 (550) | 2.35 ± 0.06 (700) | 55%@250 | 0.25 ± 0.02 (70) |

In the above tables B and C, figures between brackets describe the selectivity ratio.

Example 8

Further Non-Limiting Examples of Preferred Compounds According to the Invention having General Formula (i) are Shown as Compounds 34d, 34e, 35a, 35b, 35c, 39a, 39b and 41 Below

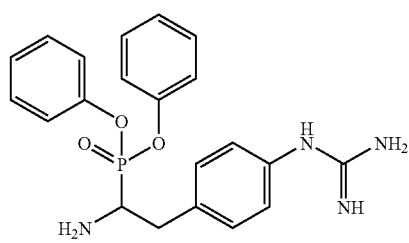

34d
diphenyl 1-amino-2-(4-guanidinophenyl)ethylphophonate

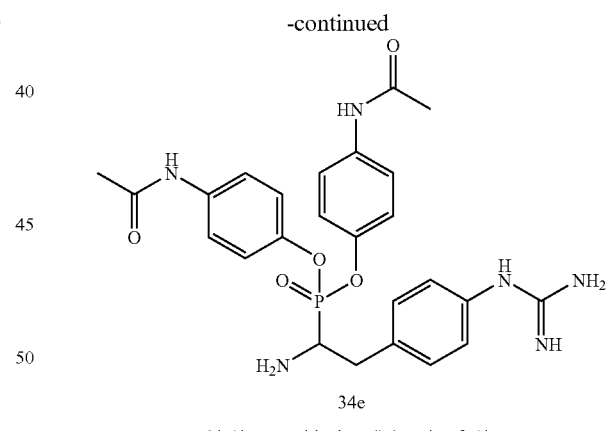

34e
bis(4-acetamidophenyl) 1-amino-2-(4-guanidinophenyl)ethylphosphonate

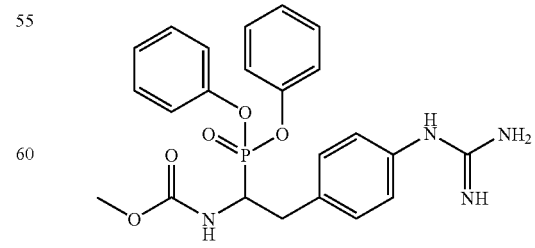

35a
methyl 1-(diphenoxyphosphonyl)-2-(4-guanidinophenyl)ethylcarbamate

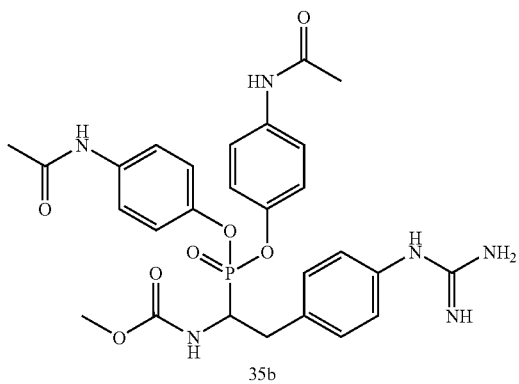

35b methyl 1-(bis(4-acetamidophenoxy)phosphonyl)-2-(4-guanidinophenyl)ethylcarbamate

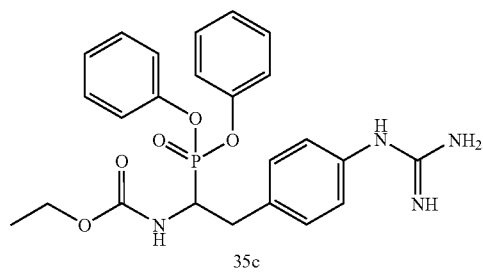

35c ethyl 1-(diphenoxyphosphonyl)-2-(4-guanidinophenyl)ethylcarbamate

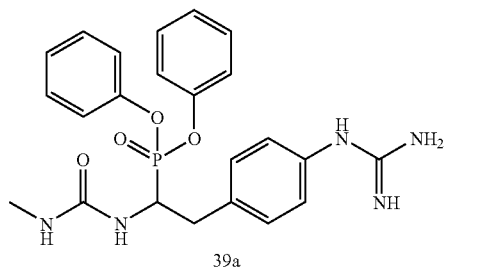

39a diphenyl 2-(4-guanidinophenyl)-1-(3-methylureido)ethylphosphonate

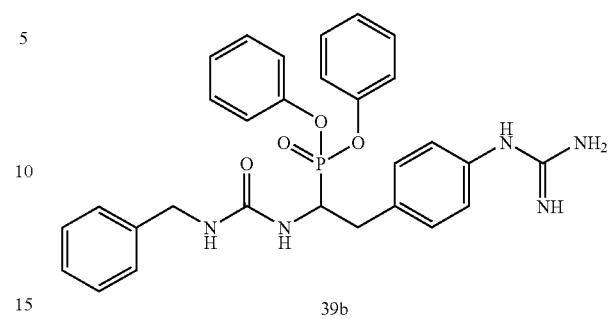

39b diphenyl 1-(3-benzylureido)-2-(4-guanidinophenyl)ethylphosphonate

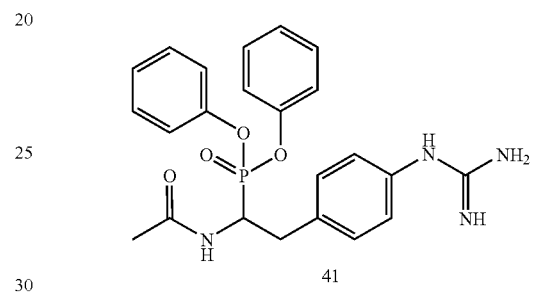

41 diphenyl 1-acetamido-2-(4-guanidinophenyl)ethylphosphonate

Example 9

Preparation of Compounds According to the Invention

The compounds 34d, 34e, 35a, 35b, 35c, 39a, 39b and 41 (as in example 8) were prepared using the procedures as described herein (the designations R", R' and R" as used in this example 9 only apply to this example 9; as used in this example 9, OPh=—OC$_6$H$_5$, i.e., phenoxy; Pcm=4-acetamidophenoxy).

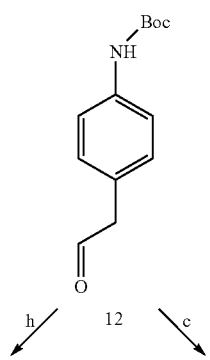

12

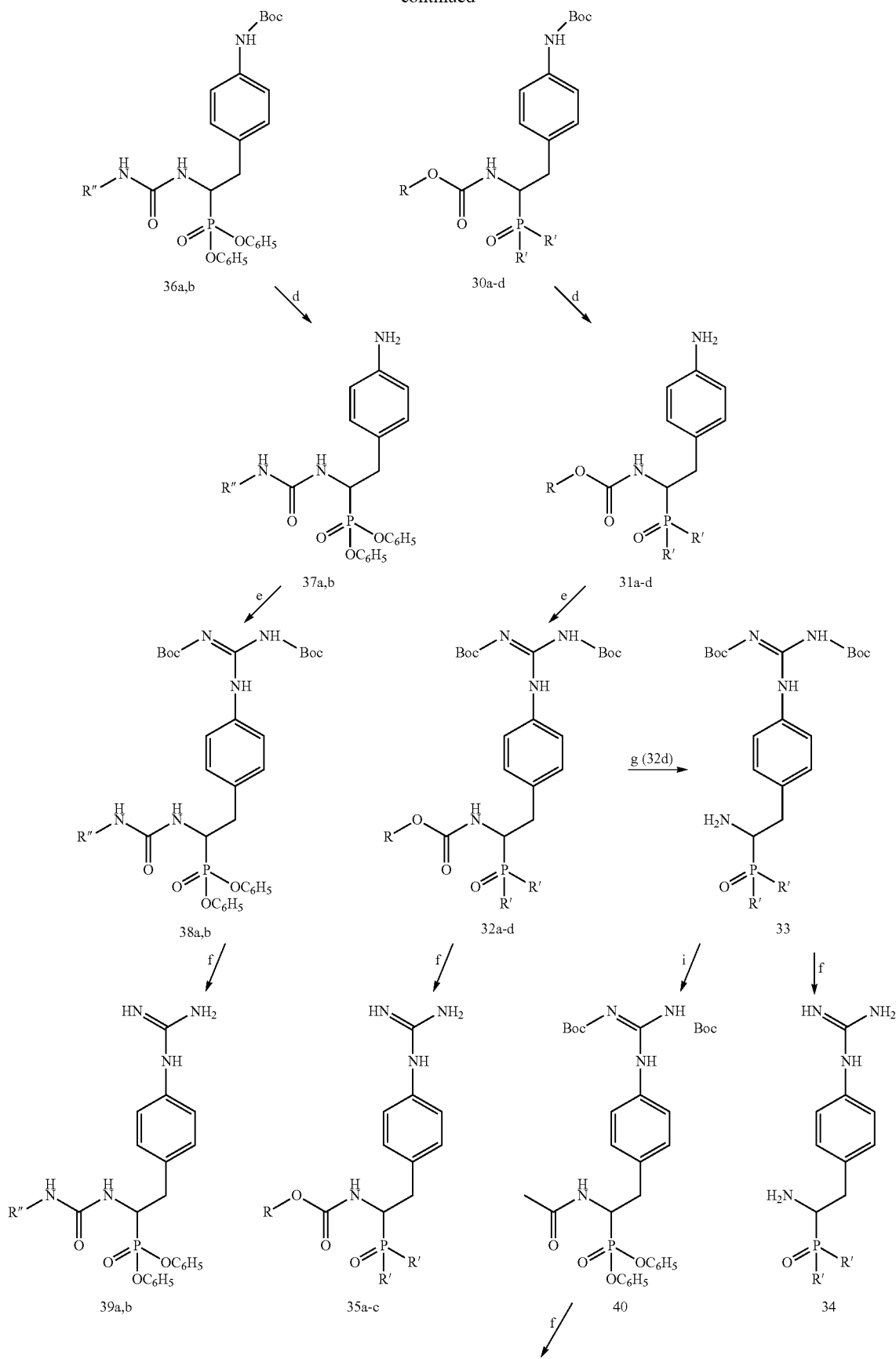

-continued

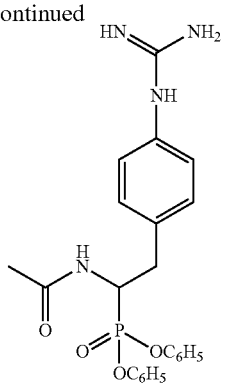

41

| | R | R' |
|---|---|---|
| a | Me | Oph |
| b | Me | Pcm |
| c | Et | Oph |
| d | Bn | Oph |

R" = —CH₃ (a), —CH₂Ph (b)

a) Boc₂O, TEA, dioxane; b) Dess-Martin, DCM; c) (PhO)₃P, ROCONH₂, Cu(OTf)₂, DCM;
d) TFA/DCM; e) N,N-bis(tert-butyloxycarbonyl-1-guanyl-pyrazole, TEA, CHCl₃; f) TFA/DCM;
g) 10% Pd/C, H2, MeOH; h) (PhO)₃P, RNHCONH₂, HClO₄, MeCN; i)Ac—Cl, DCM, Et₃N The following details the above reactions, preparation of intermediates and products and the characteristics thereof.

tert-Butyl 4-(2-oxoethyl)phenylcarbamate (12)

2-(4-Aminophenyl)ethanol (13.7 g, 0.1 mol) was dissolved in dioxane (120 ml). Triethylamine (10.1 g, 0.1 mol) was added followed by addition of Boc₂O (21.8 g, 0.1 mol). The reaction mixture was stirred overnight. After evaporation under vacuum, the residue was dissolved in ethylacetate and washed with HCl (2N) and brine. The organic layer was dried over Na₂SO₄ and evaporated. Purification by flash chromatography afforded the tert-butyl 4-(2-hydroxyethyl)phenylcarbamate as a white solid (19 g, 80 mmol, 80%). To a stirred solution of this alcohol (1 eq) in dichloromethane, a solution of Dess-Martin periodane (1.2 eq from 15% wt solution) was added. The suspension was stirred for 4 h at room temperature. The resulting solution was poured into a vigorously stirred saturated solution of NaHCO₃ and Na₂S₂O₃ (1:1, 100 ml). The organic layer was separated and washed with brine and dried over anhydrous Na₂SO₄. This crude aldehyde 12 was used directly for further reaction.

Amidoalkylation Reaction (Reaction c of the Above Scheme)

To a solution of crude aldehyde 12 (1 eq.), triphenyl phosphite (1 eq.) and carbamate derivative (1 eq.) in 50 ml dichloromethane, Cu(OTf)₂ (0.1 eq.) was added. The solution was stirred at room temperature overnight. After evaporation, the crude product was purified by chromatography to afford the pure phosphonates in 55-70% yield.

Amidoalkylation Reaction (Reaction h of the Above Scheme)

To a solution of crude aldehyde 12 (1 eq.), triphenyl phosphite (1 eq.) and urea derivative (1 eq.) in 50 ml MeCN, perchloric acid (0.15 eq.) was added. The solution was stirred at room temperature overnight. After evaporation the crude product was purified by chromatography (0-80% EtOAc in hexane) to afford the pure phosphonates in 25%-40% yield.

Removal of Tert-Butyloxycarbonyl Protecting Group (Reactions d and f of the Above Scheme)

The N-Boc protected phosphonates were dissolved in 50% trifluoroacetic acid in dichloromethane (2-5 ml). After stirring for 3 hr at room temperature the solvent was evaporated. The crude oil was washed with ether and the precipitate was isolated.

Reaction with N,N'-bis(tert-butyloxycarbonyl-1-guanylpyrazole (Reaction e of the Above Scheme)

A mixture of phosphonate (1 eq.), N,N'-bis(tert-butyloxycarbonyl-1-guanyl-pyrazole (1 eq.) and triethylamine (3 eq.) in chloroform (20 ml) was stirred at room temperature for 3 days. The solvent was evaporated and the residue was dissolved in ethylacetate and washed with 1 N HCl, saturated solution of NaHCO₃ and brine. The organic layer was dried over Na₂SO₄. The solvent was evaporated and the crude product was purified by chromatography (0-80% EtOAc in hexane) to obtain the protected guanidine.

Removal of Benzyloxycarbonyl Protecting Group (Reaction g of the Above Scheme)

The benzyloxycarbonyl-protected compound was dissolved in 20 ml MeOH and N₂ was bubbled through the solution. 10% Pd/C was added and H₂ was bubbled through the solution. The solution was stirred for 5 hr at room temperature. The solution was filtered off on a bed of celite and the filtrate was evaporated to afford the free amine.

Acetylation Reaction (Reaction i of the Above Scheme)

A suspension of the free amine (100 mg) and triethylamine (0.25 ml) in dichloromethane was cooled at −30° C. and acetyl chloride (0.012 ml) in dichloromethane was added dropwise. After 10 min the reaction was quenched by adding 1 ml of water and the organic layer was washed with saturated sodium bicarbonate solution. After drying on sodium sulfate, the solvent was evaporated and the product purified by chromatography; ethyl acetate/hexane (0-80) to afford 36 mg.

Methyl 1-(diphenoxyphosphoryl)-2-(4-(tert-butyloxycarbonylamino)phenyl)ethyl-carbamate (30a)

$^1$H-NMR (CDCl$_3$) δ 1.5 (s, 9H), 3.0-3.4 (m, 2H), 3.1 (s, 3H), 4.7 (m, 1H), 6.5 (s, 1H), 7.1-7.4 (m, 14H).

Methyl 1-(bis(4-acetamidophenoxy)phosphoryl)-2-(4-(tert-butyloxycarbonylamino)phenyl)ethylcarbamate (30b)

$^1$H-NMR (CDCl$_3$) δ 1.5 (s, 9H), 2.1 (2s, 6H), 2.8-3.3 (m, 2H), 3.3 (s, 3H), 4.5 (m, 1H), 6.8 (NH), 7.1-7.4 (m, 14H).

Ethyl 1-(diphenoxyphosphoryl)-2-(4-(tert-butyloxycarbonylamino)phenyl)ethyl-carbamate (30c)

$^1$H-NMR (CDCl$_3$) δ 1.3 (t, 3H), 1.5 (s, 9H), 3.0-3.4 (m, 2H), 4.1 (q, 2H), 4.7 (m, 1H), 5.1 (m, 1H), 6.5 (s, 1H), 7.1-7.6 (m, 12H).

Benzyl 1-(diphenoxyphosphoryl)-2-(4-(tert-butyloxycarbonylamino)phenyl)ethyl-carbamate (30d)

$^1$H-NMR (CDCl$_3$) δ 1.5 (s, 9H), 3.0-3.4 (m, 2H), 4.7 (m, 1H), 5.1 (s, 2H), 6.5 (s, 1H), 7.0-7.4 (m, 19H).

Benzyl 1-(bis(4-acetamidophenoxy)phosphoryl)-2-(4-(tert-butyloxycarbonylamino)phenyl)ethylcarbamate (30e)

$^1$H-NMR (CDCl$_3$) δ 1.5 (s, 9H), 2.1 (2s, 6H), 2.9-3.3 (m, 2H), 4.7 (m, 1H), 5.1 (s, 2H), 6.8 (NH), 7.0-7.6 (m, 17H).

Methyl 2-(4-aminophenyl)-1-(diphenoxyphosphoryl)ethylcarbamate (31a)

$^1$H-NMR (CDCl$_3$) δ 3.0-3.5 (m, 2H), 3.3 (s, 3H), 4.6 (m, 1H), 7.1-7.5 (m, 14H).

Methyl 1-(bis(4-acetamidophenoxy)phosphoryl)-2-(4-amino-phenyl)ethylcarbamate (31b)

$^1$H-NMR (CDCl$_3$) δ 2.1 (2s, 6H), 2.9-3.4 (m, 2H), 3.3 (s, 3H), 4.5 (m, 1H), 7.1-7.5 (m, 12H).

Ethyl 2-(4-aminophenyl)-1-(diphenoxyphosphoryl)ethylcarbamate (31c)

$^1$H-NMR (CDCl$_3$) δ 1.3 (s, 3H), 3.0-3.5 (m, 2H), 4.0 (q, 4H), 4.6 (m, 1H), 7.1-7.5 (m, 14H).

Benzyl 2-(4-aminophenyl)-1-(diphenoxyphosphoryl)ethylcarbamate (31d)

$^1$H-NMR (CDCl$_3$) δ 3.1-3.5 (m, 2H), 4.6 (m, 1H), 5.2 (s, 2H), 7.0-7.5 (m, 19H).

Benzyl 1-(bis(4-acetamidophenoxy)phosphoryl)-2-(4-amino-phenyl)ethylcarbamate (31e)

$^1$H-NMR (CDCl$_3$) δ 2.1 (2s, 6H), 3.0-3.4 (m, 2H), 4.6 (m, 1H), 5.2 (s, 2H), 7.0-7.6 (m, 17H).

Methyl 2-(4-(N,N'-bis(tert-butyloxycarbonyl)guanidino)phenyl)-1-(diphenoxy-phosphoryl)ethylcarbamate (32a)

$^1$H-NMR (CDCl$_3$) δ 1.5 (d, 18H), 3.0-3.4 (m, 2H), 3.5 (s, 3H), 4.7 (m, 1H), 7.1-7.6 (m, 14H).
HPLC: 214 nm: t$_r$ 17.25 min 99.14%
LC/MS: t$_r$ min. 20.8 min 98.9%
MS (ESI): m/z M+$^1$=691

Methyl 1-(bis(4-acetamidophenoxy)phosphoryl)-2-(4-N,N'-bis(tert-butyloxycarbonyl)guanidino)phenyl)ethylcarbamate (32b)

$^1$H-NMR (CDCl$_3$) δ 1.5 (d, 18H), 2.1 (2s, 6H) 3.0-3.4 (m, 2H), 3.4 (s, 3H), 4.7 (m, 1H), 6.7 (m, 1H), 7.1-7.6 (m, 12H).

Ethyl 2-(4-(N,N'-bis(tert-butyloxycarbonyl)guanidino)phenyl)-1-(diphenoxy-phosphoryl)ethylcarbamate (32c)

$^1$H-NMR (CDCl$_3$) δ 1.3 (t, 3H), 1.5 (d, 18H), 3.0-3.4 (m, 2H), 4.0 (q, 2H), 4.7 (m, 1H), 5.6 (m, 1H), 7.1-7.6 (m, 14H).
HPLC: 214 nm: t$_r$ 26.39 min 97.39%
HPLC: 254 nm: t$_r$ 26.30 min 100%
LC/MS: t, min. 20.9 min 91.3%
MS (ESI): m/z M$^{+Na}$=705

Benzyl 2-(4-(N,N'-bis(tert-butyloxycarbonyl)guanidino)phenyl)-1-(diphenoxy-phosphoryl)ethylcarbamate (32d)

$^1$H-NMR (CDCl$_3$) δ 1.5 (d, 18H), 3.0-3.4 (m, 2H), 4.7 (m, 1H), 5.0 (s, 2H), 5.9 (m, 1H), 7.0-7.4 (m, 19H).
HPLC: 214 nm: t$_r$ 28.97 min 96.07%
HPLC: 254 nm: t$_r$ 28.06 min 99.6%
MS (ESI): m/z M$^{+Na}$=881

Benzyl 1-(bis(4-acetamidophenoxy)phosphoryl)-2-(4-(N,N'-bis(tert-butyloxycarbonyl)guanidino)phenyl)ethylcarbamate (32e)

$^1$H-NMR (CDCl$_3$) δ 1.5 (d, 18H), 2.1 (2s, 6H), 2.8-3.3 (m, 2H), 4.7 (m, 1H), 5.1 (s, 2H), 7.0-7.6 (m, 17H).

Diphenyl 1-amino-2-(4-(N,N'-bis(tert-butyloxycarbonyl) guanidinophenyl)ethyl-phosphonate (33d)

$^1$H-NMR (CDCl$_3$) δ 1.5 (d, 18H), 2.8-3.4 (m, 2H), 3.7 (m, 1H), 7.0-7.4 (m, 14H).
HPLC: 214 nm: t$_r$ 7.17 min 90.54%
HPLC: 254 nm: t$_r$ 7.08 min 94.23%
LC/MS: t$_r$ min. 1.7 min 93.1%
MS (ESI): m/z M$^{+Na}$=633

Bis(4-acetamidophenyl) 1-amino-2-(4-N,N'-bis(tert-butyloxycarbonyl) guanidinophenyl)ethyl-phosphonate (33e)

$^1$H-NMR (CDCl$_3$) δ 1.5 (d, 18H), 2.1 (2s, 6H), 2.9-3.4 (m, 2H), 3.6 (m, 1H), 7.0-7.6 (m, 12H).
HPLC: 214 nm: t$_r$ 6.21 min 90.33%
HPLC: 254 nm: t$_r$ 6.17 min 93.26%

LC/MS: $t_r$ min. 1.3 min 91.6%
MS (ESI): m/z $M^{+Na}$=747

Diphenyl 1-amino-2-(4-guanidinophenyl)ethylphosphonate (34d)

$^1$H-NMR (CDCl$_3$) δ 3.0-3.4 (m, 2H), 4.7 (m, 1H), 7.0-7.4 (m, 14H).

Bis(4-acetamidophenyl) 1-amino-2-(4-guanidinophenyl)ethylphosphonate (34e)

$^1$H-NMR (CDCl$_3$) δ 2.1 (2s, 6H), 2.8-3.4 (m, 2H), 4.6 (m, 1H), 7.0-7.6 (m, 12H).

Methyl 1-(diphenoxyphosphoryl)-2-(4-guanidinophenyl)ethylcarbamate (35a)

$^1$H-NMR (CDCl$_3$) δ 2.9-3.4 (m, 2H), 4.5 (s, 3H), 4.7 (m, 1H), 7.0-7.5 (m, 14H).

Methyl 1-(bis(4-acetamidophenoxy)phosphoryl)-2-(4-guanidino-phenyl)ethylcarbamate (35b)

$^1$H-NMR (CDCl$_3$) δ2.1 (2s, 6H), 2.9-3.4 (m, 2H), 4.6 (s, 3H), 4.7 (m, 1H), 7.0-7.5 (m, 12H).
HPLC: 214 nm: $t_r$ 10.87 min 98.0%
LC/MS: $t_r$ min. 10.7 min 96.4%
MS (ESI): m/z $M^{+1}$=583

Ethyl 1-(diphenoxyphosphoryl)-2-(4-guanidinophenyl)ethylcarbamate (35c)

$^1$H-NMR (CDCl$_3$) δ 1.2 (t, 3H), 3.0-3.4 (m, 2H), 4.3 (q, 2H), 4.7 (m, 1H), 7.0-7.5 (m, 14H).

tert-Butyl 4-(2-(diphenoxyphosphoryl)-2-(3-methylureido)ethyl)phenylcarbamate (36a)

$^1$H-NMR (CDCl$_3$) δ 1.5 (s, 9H), 2.4-3.2 (m, 2H), 3.0 (s, 3H), 4.1 (m, 1H), 6.7 (m, 1H), 7.1-7.4 (m, 14H).

tert-Butyl 4-(2-(3-benzylureido)-2-(diphenoxyphosphoryl)ethyl)phenylcarbamate (36b)

$^1$H-NMR (CDCl$_3$) δ 1.5 (s, 9H), 2.4-3.2 (m, 2H), 4.1 (m, 1H), 4.3 (s, 2H), 6.7 (m, 1H), 7.0-7.4 (m, 19H).

Diphenyl 2-(4-aminophenyl)-1-(3-methylureido)ethylphosphonate (37a)

$^1$H-NMR (CDCl$_3$) δ 2.5-3.2 (m, 2H), 2.9 (s, 3H), 4.1 (m, 1H), 7.1-7.4 (m, 14H).

Diphenyl 2-(4-aminophenyl)-1-(3-benzylureido)ethylphosphonate (37b)

$^1$H-NMR (CDCl$_3$) δ2.6-3.3 (m, 2H), 4.2 (m, 1H), 4.4 (s, 2H), 6.7 (m, 1H), 7.0-7.4 (m, 19H).

2-(4-(N,N'-bis(tert-Butyloxycarbonyl)guanidino)phenyl)-1-(3-methylureido)-1-(diphenoxyphosphoryl)ethylcarbamate (38a)

$^1$H-NMR (CDCl$_3$) δ 1.5 (d, 18H), 2.4-3.2 (m, 2H), 3.1 (s, 3H), 4.3 (m, 1H), 7.1-7.4 (m, 14H).

2-(4-(N,N'-bis(tert-Butyloxycarbonyl)guanidino)phenyl)-1-(3-benzylureido)-1-(diphenoxyphosphoryl)ethylcarbamate (38b)

$^1$H-NMR (CDCl$_3$) δ 1.5 (d, 18H), 2.5-3.3 (m, 2H), 4.4 (m, 1H), 4.5 (s, 2H), 7.0-7.4 (m, 19H).

Diphenyl 2-(4-guanidinophenyl)-1-(3-methylureido)ethylphosphonate (39a)

$^1$H-NMR (CDCl$_3$) δ 2.5-3.2 (m, 2H), 3.0 (s, 3H), 4.4 (m, 1H), 7.1-7.5 (m, 14H).
HPLC: 214 nm: $t_r$ 9.23 min 93.4%
LC/MS: $t_r$ min. 8.9 min 96.4%
MS (ESI): m/z $M^{+1}$=468

Diphenyl 1-(3-benzylureido)-2-(4-guanidinophenyl)ethylphosphonate (39b)

$^1$H-NMR (CDCl$_3$) δ2.6-3.3 (m, 2H), 4.4 (m, 1H), 4.5 (s, 2H), 7.0-7.5 (m, 19H).
HPLC: 214 nm: $t_r$ 10.63 min 98.0%
LC/MS: t, min. 9.6 min 92.8%
MS (ESI): m/z M+$^1$=544

Diphenyl 1-acetamido-2-(4-(N,N'-bis(tert-butyloxycarbonyl)guanidino)phenyl)-ethylphosphonate (40)

$^1$H-NMR (CDCl$_3$) δ 1.5 (d, 18H), 1.7 (s, 3H), 3.0-3.4 (m, 2H), 5.1 (m, 1H), 5.9 (NH), 7.1-7.6 (m, 14H), 10.3 (NH), 11.6 (NH).
HPLC: 214 nm: $t_r$ 26.72 min 100%
HPLC: 254 nm: $t_r$ 26.69 min 100%
LC/MS: $t_r$ min. 20.5 min 100.0%
MS (ESI): m/z $M^{+Na}$=675

Diphenyl 1-acetamido-2-(4-guanidinophenyl)ethylphosphonate (41)

$^1$H-NMR (CDCl$_3$) δ 1.7 (s, 3H), 3.0-3.4 (m, 2H), 5.0 (m, 1H), 6.5 (NH), 7.0-7.5 (m, 14H), 10.0 (NH).
HPLC: 214 nm: $t_r$ 15.34 min 100%
HPLC: 254 nm: $t_r$ 15.30 min 100%
LC/MS: $t_r$ min. 12.2 min 100.0%
MS (ESI): m/z $M^{+1}$=453

Example 10

Biochemical Evaluation

The compounds of example 8 were evaluated for their ability to inhibit various trypsin-like serine proteases using the appropriate chromogenic substrates. The IC$_{50}$ values were calculated for uPA and five other trypsin-like serine proteases (Table D).

TABLE D

| | IC$_{50}$ (nM) | k$_{app}$ (M$^{-1}$·s$^{-1}$) | IC$_{50}$ (μM) or % inhibition at given concentration (μM)$^a$ | | | | |
|---|---|---|---|---|---|---|---|
| | uPA | uPA | tPA | Plasmin | Thrombin | FXa | Tryp |
| 34d | 1600 ± 130 | NA | 32% @ 250 | 31% @ 250 | 41% @ 250 | 11% @ 250 | NA |
| 34e | NA | NA | NA | NA | NA | NA | NA |
| 35a | 3.1 ± 0.5 | 62 × 10$^3$ ± 4 × 10$^3$ | 23 ± 6 (7419) | 12.8 ± 2 (4129) | 16.6 ± 2.3 (5355) | 57% @ 250 | NA |
| 35b | NA | NA | NA | NA | NA | NA | NA |
| 35c | 8.0 ± 3.0 | 40 × 10$^3$ ± 20 × 10$^3$ | 57 ± 14 (7125) | 16 ± 3 (2000) | 3.8 ± 0.2 (475) | 62% @ 250 | NA |
| 39a | 101000 ± 6800 | NA | 42% @ 250 | 15% @ 250 | 42% @ 250 | 27% @ 250 | NA |
| 39b | 43900 ± 3900 | NA | 50% @ 250 | 34% @ 250 | 46% @ 250 | 36% @ 250 | NA |
| 41 | 9.9 ± 0.8 | NA | 36.6 ± 2.2 (3697) | 57 ± 1.3 (5758) | 32.2 ± 1.4 (3253) | 37% @ 250 | NA |

In the above table D, figures between brackets describe the selectivity index (IC$_{50}$/IC$_{50}$ uPA).
NA = not available.

Example 11

Protocol Used for Biochemical Evaluation

These protocols detail the methods used for biochemical evaluation of the compounds of the invention in the above examples, in particular examples 7 and 10.

uPA Inhibition: In Vitro Evaluation

Enzymatic activity was measured at 37° C. in a Spectramax 340 (Molecular Devices) microtiter plate reader using the chromogenic substrate S-2444 (L-pyroGlu-Gly-L-Arg-p-NA.HCl), with a Km of 80 μM. The substrate was obtained from Chromogenix. The human enzyme was obtained from Sigma-Aldrich, the mouse uPA was obtained from Molecular Innovations.Inc (USA). The reaction was monitored at 405 nm, and the initial rate was determined between 0 and 0.25 absorbance units in 20 min. The reaction mixture contained 250 μM substrate and approximately 1 mU of enzyme in 145 μl of buffer in a final volume of 200 μl. A 50 mM Tris buffer, pH 8.8, was used. From each inhibitor concentration 5 μl was added, obtaining a final concentration from 0-250 μM in a total volume of 0.2 ml. Activity measurements were routinely performed in duplicate. The IC$_{50}$ value is defined as the concentration of inhibitor required to reduce the enzyme activity to 50% after a 15-min pre-incubation with the enzyme at 37° C. before addition of the substrate. IC$_{50}$ values were obtained by fitting the data with the 4 parameter logistics equation using Grafit 5.

$$v = (vrange)/(1+\exp(s*\ln(abs(I_0/IC_{50})))) + back$$

s: slope factor
back: background
v: rate
I$_0$: inhibitor concentration
range: the fitted uninhibited value minus the background.

The equation assumes that y falls with increasing x.

Inhibitor stock solutions were prepared in DMSO and stored at −20° C. Since the compounds described in this paper completely inactivate uPA following pseudo-first-order kinetics, the IC$_{50}$ value is inversely correlated with the second-order rate constant of inactivation. For a simple pseudo-first-order inactivation process, the activity after incubation with inhibitor (v$_i$) varies with the inhibitor concentration (i) as described in the following equation: $v_i = v_0 \cdot e^{-kit}$, where v$_0$ is the activity in absence of inhibitor, k is the second-order rate constant of inactivation, and t is the time.

The inactivation rate constant was determined from the time course of inhibition.

The inhibitor was mixed with the substrate (250 μM final concentration) and the buffer solution with the enzyme was added at the time zero. The inhibitor concentrations were chosen to obtain total inhibition of the enzyme within 20 min. The progress curves show the absorbance of p-nitroanilide produced as a function of time. Initially no inhibitor is bound to the enzyme and the tangent to the progress curve (dA/dt) is proportional to the concentration of the free enzyme. The concentration of free enzyme decreases over time due to the kinetics of inhibitor binding as described above. Progress curves were recorded in pseudo-first order conditions ([I]$_0$ >> [E]$_0$) and with less than 10% conversion of the substrate during the entire time course. In these conditions dA/dt decreases exponentially with time. The progress curves were fitted with the integrated rate equation to yield a value for kobs, a pseudo-first order rate constant.

$$A_t = v_0 \cdot [1-\exp(-k_{obs} \cdot t)]/k_{obs} + A_0.$$

A$_t$ = absorbance at time t
A$_O$ = absorbance at time zero
v$_0$ = uninhibited initial rate The apparent second order rate constant (k$_{app}$) was calculated from the slope of the linear part of the plot of k$_{obs}$ vs. the inhibitor concentration ([I]$_0$). In case of competition between the inhibitor and the substrate, k$_{app}$ is smaller than the "real" second order rate constant, k discussed above, because a certain fraction of the enzyme is present as an enzyme-substrate complex. k$_{app}$ depends upon the substrate concentration used in the experiment as described by Lambeir et al. 1996 (Biochim Biophys Acta 1290: 76-82).

Determination of the Selectivity for uPA

The IC$_{50}$ values for plasmin, tPA, thrombin and FXa were determined in the same way as for uPA. S-2288 (H-D-Ile-Pro-Arg-pNa.2HCl) for tPA (K$_m$: 1 mM), S-2366 (pyroGlu-Pro-Arg-pNA.HCl) for plasmin (K$_m$: 400 μM) and thrombin (K$_m$: 150 μM) and S-2772 (Boc-D-Arg-Gly-Arg-pNA.2HCl) for FXa (K$_m$: 1.5 mM) and BAPNA (Nα-benzoyl-DLArg-pNA.HCl) for trypsin (Km: 1 mM) were used as substrates. FX is activated with Russel's Viper Venom.

The mixture contained 580 μM substrate for thrombin and plasmin, 1.25 mM for tPA, 522 μM for FXa and 425 μM for trypsin. Approximately 5 mU of enzyme, and 145 μl of buffer. For tPA and thrombin Tris buffer, pH 8.3, for FXa, Tris buffer pH 8.3 with 2.5 mM CaCl$_2$, for plasmin Tris buffer pH 7.4, and for trypsin Tris buffer pH 8.2 was used. The selectivity index was calculated as (IC$_{50}$ Enzyme X)/IC$_{50}$ uPA, where X is tPA, thrombin, plasmin or FXa.

Determination of the Inhibition Type

In order to follow the dissociation of the inhibitor-enzyme complex, aliquots of enzyme were incubated without inhibitor and in the presence of a concentration of the inhibitor 50 times the $IC_{50}$, at 37° C. The enzyme concentration was 2.5 times higher than the concentration used for the $IC_{50}$ determinations. After 15 min the aliquots were diluted 50-fold into the substrate concentration and assay buffer used for the $IC_{50}$ determination. The dissociation of the enzyme-inhibitor complex was monitored by substrate hydrolysis by measuring the absorbance every 20 s.

The invention claimed is:

1. A compound having the formula (I)

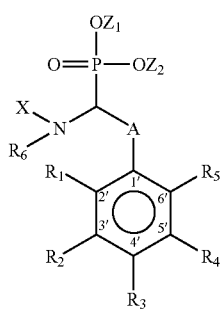

and stereoisomeric forms, racemic mixtures, prodrugs, pharmaceutically acceptable salts and N-oxides thereof,
wherein $R^3$ is guanidino, optionally substituted with ethyl or methyl;
wherein $R^1$, $R^2$, $R^4$ and $R^5$ are, each independently, chosen from the group consisting of hydrogen, halogen, perhaloalkyl, alkoxy, alkanoyl, alkanoyloxy, and alkoxycarbonyl;
wherein A is methylene or ethylene;
wherein $R^6$ is hydrogen or methyl;
wherein X is chosen from the group consisting of hydrogen, $C_{1-6}$alkyl, aryl, aralkyl, perhaloalkyl, formyl, alkanoyl, aroyl, aralkanoyl, alkoxycarbonyl, aryloxycarbonyl, aralkoxycarbonyl, carbamoyl, alkylcarbamoyl, arylcarbamoyl, aralkylcarbamoyl, alkylsulfinyl, arysulfinyl, aralkylsulfinyl, alkylsulfonyl, arylsulfonyl, aralkylsulfonyl, aminosulfinyl and aminosulfonyl, optionally substituted with one or more substituents independently chosen from the group comprising or consisting of: halogen, perhaloalkyl, nitro, cyano, alkyl, aryl, aralkyl, hydroxyl, alkoxy, aryloxy, aralkoxy, —OC(=NR∝)R″, mercapto, alkylthio, arylthio, aralkylthio, —SC(=NR')R″, formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl and substituted carbamoyl, alkylcarbamoyl, arylcarbamoyl, aralkyl carbamoyl, formylamino, alkanoylamino, cycloalkylcarbonylamino, aroylamino, aralkanoylamino, sulfo and substituted sulfo, sulfonyl, aminosulfonyl, imino, —C(=NR')OH, —C(=NR')OR″, —C(=NR')SH, —C(=NR')SR″, oxo, primary amino, alkylamino, dialkylamino, arylamino, aralkylamino, —NR'C(=O)OR″, —NR'C(O)NR″R‴, —NR'C(S)NR″R‴, —N(OH)C(=O)OR', —NR'C(=O)SR″, —N(OH)C(=O)NR'R″, —N(OH)C(S)NR'R″, —NR'C(O)N(OH)R″, —NR'C(S)N(OH)R″, —NR'S(=O)$_2$R″, —NHS(=O)$_2$NR'R″, —NR'S(=O)$_2$NHR″, and —P(=O)(OR')(OR″), wherein R', R″ and R‴ each independently, selected from the group comprising or consisting of hydrogen, hydroxyl, alkyl, aryl, aralkyl, optionally substituted with one or more substituents independently chosen from the group comprising or consisting of halogen, hydroxyl, oxo, alkoxy, aryloxy, aralkoxy, alkanoyl, oxoalkyl, carboxyl, alkyloxycarbonyl, cyano and amino;
wherein $Z^1$ and $Z^2$ is, each independently, chosen from the group consisting of aryl, wherein any $Z^1$ and $Z^2$ groups is, each independently, optionally substituted with one or more substituents independently chosen from the group comprising: halogen, perhaloalkyl, alkyl, aryl, aralkyl, alkoxy, aryloxy, aralkoxy, alkanoyl, aroyl, aralkanoyl, alkanoyloxy, aroyloxy, aralkanoyloxy, alkoxycarbonyl, aryloxycarbonyl, aralkoxycarbonyl, oxo, primary amino, alkylamino, dialkylamino, arylamino, and aralkylamine, alkanoylamino, cycloalkylcarbonylamino, aroylamino, and aralkanoylamino.

2. The compound according to claim 1 and stereoisomeric forms, racemic mixtures, prodrugs, pharmaceutically acceptable salts and N-oxides thereof, wherein A is chosen from $C_{1-6}$alkylene, wherein the said $C_{1-6}$alkylene is optionally substituted by one or more substituents independently chosen from the group consisiting of halogen, perhaloalkyl, nitro, cyano, alkyl, hydroxyl, alkanoyloxy, primary amino, secondary amino, and tertiary amino, wherein the substituents in the secondary and tertiary amino are, each independently, chosen from the group consisting of alkyl, aryl and aralkyl.

3. The compound according to claim 1 wherein A is methylene.

4. The compound according to claim 1 and stereoisomeric forms, racemic mixtures, prodrugs, pharmaceutically acceptable salts and N-oxides thereof, wherein X is chosen from the group consisting of: hydrogen, $C_{1-6}$alkyl, aryl, aralkyl, perhaloalkyl, formyl, alkanoyl, aroyl, aralkanoyl, alkoxycarbonyl, aryloxycarbonyl, aralkoxycarbonyl, carbamoyl, alkylcarbamoyl, arylcarbamoyl, aralkylcarbamoyl, alkylsulfinyl, arysulfinyl, aralkylsulfinyl, alkylsulfonyl, arylsulfonyl, aralkylsulfonyl, aminosulfinyl and aminosulfonyl.

5. The compound according to claim 1 and stereoisomeric forms, racemic mixtures, prodrugs, pharmaceutically acceptable salts and N-oxides thereof, wherein $Z^1$ and $Z^2$ are, each independently, chosen from the group consisting of phenyl, optionally substituted with one or more substituents independently chosen from the group consisting of halogen, alkyl, perhaloalkyl, alkoxy, alkanoyl, alkanoyloxy, alkoxycarbonyl and alkanoylamino.

6. The compound according to claim 1 and stereoisomeric forms, racemic mixtures, prodrugs, pharmaceutically acceptable salts and N-oxides thereof, wherein $R^1$, $R^2$, $R^4$ and $R^5$ are, each independently, chosen from the group comprising: hydrogen, halogen, perhaloalkyl, alkyl, aralkyl, hydroxyl, alkoxy, aryloxy, aralkoxy, formyl, alkanoyl, aroyl, aralkanoyl, formyloxy, alkanoyloxy, aroyloxy, aralkanoyloxy, carboxyl, alkoxycarbonyl, aryloxycarbonyl, aralkoxycarbonyl, carbamoyl, alkylcarbamoyl, arylcarbamoyl, aralkylcarbamoyl, and sulfonyl.

7. The compound according to claim 1 and stereoisomeric forms, racemic mixtures, prodrugs, pharmaceutically acceptable salts and N-oxides thereof,
wherein $R^3$ is guanidino; wherein $R^1$, $R^2$, $R^4$ and $R^5$ each are hydrogen; wherein A is methylene or ethylene; wherein $Z^1$ and $Z^2$ are, each independently, phenyl, p-acetylaminophenyl, hydroxyphenyl, methoxyphenyl, sulfonylaminophenyl, ureylphenyl, methoxycarbonylphenyl or alkylaminocarbonylphenyl; wherein $R^6$ is hydrogen or methyl; and wherein X is hydrogen, methoxycarbonyl, ethoxycarbonyl, methylcarbonyl, methylcarbamoyl, ethylcarbamoyl, benzylcarbamoyl, phenylmethoxycarbonyl, benzoyl, phenylsulfonyl, benzylsulfonyl, naphtylsulfonyl, (2,4,6-trimethyl)phenylsulfonyl, —S(=O)$_2$CH$_3$ or —S(=O)$_2$H.

8. The compound according to claim 1 and stereoisomeric forms, racemic mixtures, prodrugs, pharmaceutically acceptable salts and N-oxides thereof, wherein R$^3$ is guanidino; wherein R$^1$, R$^2$, R$^4$ and R$^5$ each are hydrogen; wherein A is methylene; wherein Z$^1$ and Z$^2$ are phenyl or Z$^1$ and Z$^2$ are p-acetylaminophenyl; wherein R$^6$ is hydrogen; and wherein X is hydrogen, methoxycarbonyl, ethoxycarbonyl, methylcarbonyl, methylcarbamoyl, ethylcarbamoyl, benzylcarbamoyl, phenylmethoxycarbonyl, benzoyl, phenylsulfonyl, benzylsulfonyl, naphtylsulfonyl, (2,4,6-trimethyl)phenylsulfonyl, —S(=O)$_2$CH$_3$ or —S(=O)$_2$H.

9. The compound according to claim 1 and stereoisomeric forms, racemic mixtures, prodrugs, pharmaceutically acceptable salts and N-oxides thereof, wherein R$^3$ is guanidino; wherein R$^1$, R$^2$, R$^4$ and R$^5$ each are hydrogen; wherein A is methylene; wherein Z$^1$ and Z$^2$ are phenyl or Z$^1$ and Z$^2$ are p-acetylaminophenyl; wherein R$^6$ is hydrogen; and wherein X is hydrogen, methoxycarbonyl, ethoxycarbonyl, methylcarbonyl, methylcarbamoyl, ethylcarbamoyl, benzylcarbamoyl, phenylmethoxycarbonyl, benzylsulfonyl or naphtylsulfonyl.

10. The compound according to claim 1 and stereoisomeric forms, racemic mixtures, prodrugs, pharmaceutically acceptable salts and N-oxides thereof,
wherein the compound is Diphenyl 1-(benzyloxycarbonylamino)-2-(4-guanidinophenyl)-ethanephosphonate, Diphenyl 1-(benzoylamino)-2-(4-guanidinophenyl)-ethanephosphonate, Diphenyl 1-(o-toluenesulfonylamino)-2-(4-guanidinophenyl)-ethanephosphonate, Diphenyl 1-(naphthalenesulfonylamino)-2-(4-guanidinophenyl)-ethanephosphonate, Diphenyl 1-(2,3,6-triisopropylbenzenesulfonyl)amino-2-(4-guanidinophenyl)-ethanephosphonate, Diphenyl 1-(methylsulfonylamino)-2-(4-guanidinophenyl)-ethanephosphonate, Di-(4-acetamidophenyl) 1-(benzyloxycarbonylamino)-2-[(4-guanidino)phenyl]ethanephosphonate, Di-(4-acetamidophenyl) 1-(methylsulfonylamino)-2-(4-guanidinophenyl)-ethanephosphonate, Diphenyl 1-amino-2-(4-guanidinophenyl)ethylphosphonate}, Bis(4-acetamidophenyl) 1-amino-2-(4-guanidinophenyl)ethylphosphonate, Methyl 1-(diphenoxyphosphoryl)-2-(4-guanidinophenyl)ethylcarbamate, Methyl 1-(bis(4-acetamidophenoxy)phosphoryl)-2-(4guanidino-phenyl)ethylcarbamate, Ethyl 1-(diphenoxyphosphoryl)-2-(4-guanidinophenyl)ethylcarbamate, Diphenyl 2-(4-guanidinophenyl)-1-(3-methylureido) ethylphosphonate, Diphenyl 1-(3-benzylureido)-2-(4-guanidinophenyl)ethylphosphonate or Diphenyl 1-acetamido-2-(4-guanidinophenyl)ethylphosphonate.

11. An in vitro method for inhibiting the activity of urokinase plasminogen activator, comprising the step of adding a compound according to claim 1.

12. A pharmaceutical composition comprising a pharmaceutically acceptable excipient and a therapeutically effective amount of a compound according to claim 1.

13. A method of treating tumour metastasis, comprising administering to an individual in need of such treatment a compound according to claim 1.

14. A method of treating tumour metastasis, comprising administering to an individual in need of such treatment a pharmaceutical composition according to claim 12.

* * * * *

UNITED STATES PATENT AND TRADEMARK OFFICE
CERTIFICATE OF CORRECTION

PATENT NO. : 8,003,627 B2
APPLICATION NO. : 12/090984
DATED : August 23, 2011
INVENTOR(S) : Augustyns et al.

Page 1 of 1

It is certified that error appears in the above-identified patent and that said Letters Patent is hereby corrected as shown below:

In the Claims:

Column 75, Lines 50-51, replace "–OC(=NRα)R''" with -- –OC(=NR')R" --.

Column 76, Line 1, replace "each independently," with -- are, each independently, --.

Signed and Sealed this
Fifteenth Day of October, 2013

Teresa Stanek Rea
*Deputy Director of the United States Patent and Trademark Office*